(12) United States Patent
Knight et al.

(10) Patent No.: US 9,907,482 B2
(45) Date of Patent: Mar. 6, 2018

(54) SYSTEMS AND METHODS TO GATHER AND ANALYZE ELECTROENCEPHALOGRAPHIC DATA

(71) Applicant: The Nielsen Company (US), LLC, New York, NY (US)

(72) Inventors: Robert T. Knight, Berkeley, CA (US); Ramachandran Gurumoorthy, Berkeley, CA (US); Yakob Badower, Frankfurt am Main (DE); A. K. Pradeep, Berkeley, CA (US)

(73) Assignee: THE NIELSEN COMPANY (US), LLC, New York, NY (US)

( * ) Notice: Subject to any disclaimer, the term of this patent is extended or adjusted under 35 U.S.C. 154(b) by 260 days.

(21) Appl. No.: 14/746,440

(22) Filed: Jun. 22, 2015

(65) Prior Publication Data

US 2015/0282730 A1    Oct. 8, 2015

Related U.S. Application Data

(63) Continuation of application No. 13/728,900, filed on Dec. 27, 2012, now Pat. No. 9,060,671.

(Continued)

(51) Int. Cl.
*A61B 5/0478* (2006.01)
*A61B 5/00* (2006.01)
(Continued)

(52) U.S. Cl.
CPC .............. *A61B 5/0478* (2013.01); *A61B 5/00* (2013.01); *A61B 5/0006* (2013.01);
(Continued)

(58) Field of Classification Search
CPC ........................... A61B 5/0476; A61B 5/0478
See application file for complete search history.

(56) References Cited

U.S. PATENT DOCUMENTS

| 2,409,033 A | 10/1946 | Garceau |
| 2,549,836 A | 4/1951 | McIntyre et al. |

(Continued)

FOREIGN PATENT DOCUMENTS

| CN | 1538823 | 10/2004 |
| DE | 102010005551 | 7/2011 |

(Continued)

OTHER PUBLICATIONS

Final Rejection, issued by the United States Patent and Trademark Office in connection with U.S. Patent Application No. 13730212, dated Dec. 3, 2015, 28 pages.

(Continued)

*Primary Examiner* — Lee S Cohen
(74) *Attorney, Agent, or Firm* — Hanley, Flight & Zimmerman, LLC

(57) ABSTRACT

Example devices are disclosed herein that include a first elongated band coupled to a first housing to be located on a first side of a head of a subject and a second housing to be located near a second side of the head of the subject, the first elongated band comprising a first set of electrodes. The example device also includes a second elongated band coupled to the first housing and to the second housing, the second elongated band comprising a second set of electrodes. In addition, the device includes a third elongated band coupled to the first housing and to the second housing, the third elongated band comprising a third set of electrodes.

20 Claims, 50 Drawing Sheets

Related U.S. Application Data

(60) Provisional application No. 61/684,640, filed on Aug. 17, 2012.

(51) Int. Cl.
  *A61B 5/04* (2006.01)
  *A61B 5/16* (2006.01)
  *A61B 5/0476* (2006.01)
  *A61B 5/048* (2006.01)

(52) U.S. Cl.
  CPC ........ *A61B 5/04012* (2013.01); *A61B 5/0476* (2013.01); *A61B 5/165* (2013.01); *A61B 5/6803* (2013.01); *A61B 5/6831* (2013.01); *A61B 5/7203* (2013.01); *A61B 5/048* (2013.01); *A61B 2562/0209* (2013.01); *A61B 2562/182* (2013.01)

(56) References Cited

U.S. PATENT DOCUMENTS

| | | |
|---|---|---|
| 3,490,439 A | 1/1970 | Rolston |
| 3,508,541 A | 4/1970 | Westbrook et al. |
| 3,572,322 A | 3/1971 | Wade |
| 3,735,753 A | 5/1973 | Pisarski |
| 3,880,144 A | 4/1975 | Coursin et al. |
| 3,901,215 A | 8/1975 | John |
| 3,998,213 A | 12/1976 | Price |
| 4,033,334 A | 7/1977 | Fletcher et al. |
| 4,075,657 A | 2/1978 | Weinblatt |
| 4,149,716 A | 4/1979 | Scudder |
| 4,201,224 A | 5/1980 | John |
| 4,213,463 A | 7/1980 | Osenkarski |
| 4,279,258 A | 7/1981 | John |
| 4,397,331 A | 8/1983 | Medlar |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,613,951 A | 9/1986 | Chu |
| 4,626,904 A | 12/1986 | Lurie |
| 4,632,122 A | 12/1986 | Johansson et al. |
| 4,640,290 A | 2/1987 | Sherwin |
| 4,683,892 A | 8/1987 | Johansson et al. |
| 4,695,879 A | 9/1987 | Weinblatt |
| 4,709,702 A | 12/1987 | Sherwin |
| 4,736,751 A | 4/1988 | Gevins et al. |
| 4,755,045 A | 7/1988 | Borah et al. |
| 4,770,180 A | 9/1988 | Schmidt et al. |
| 4,800,888 A | 1/1989 | Itil et al. |
| 4,802,484 A | 2/1989 | Friedman et al. |
| 4,846,190 A | 7/1989 | John |
| 4,865,038 A | 9/1989 | Rich et al. |
| 4,885,687 A | 12/1989 | Carey |
| 4,894,777 A | 1/1990 | Negishi et al. |
| 4,913,160 A | 4/1990 | John |
| 4,931,934 A | 6/1990 | Snyder |
| 4,936,306 A | 6/1990 | Doty |
| 4,955,388 A | 9/1990 | Silberstein |
| 4,967,038 A | 10/1990 | Gevins et al. |
| 4,974,602 A | 12/1990 | Abraham-Fuchs et al. |
| 4,987,903 A | 1/1991 | Keppel et al. |
| 5,003,986 A | 4/1991 | Finitzo et al. |
| 5,010,891 A | 4/1991 | Chamoun |
| 5,024,235 A | 6/1991 | Ayers |
| 5,038,782 A | 8/1991 | Gevins et al. |
| 5,052,401 A | 10/1991 | Sherwin |
| 5,083,571 A | 1/1992 | Prichep |
| RE34,015 E | 8/1992 | Duffy |
| 5,137,027 A | 8/1992 | Rosenfeld |
| 5,213,338 A | 5/1993 | Brotz |
| 5,226,177 A | 7/1993 | Nickerson |
| 5,243,517 A | 9/1993 | Schmidt et al. |
| 5,273,037 A | 12/1993 | Itil et al. |
| 5,291,888 A | 3/1994 | Tucker |
| 5,293,867 A | 3/1994 | Oommen |
| 5,295,491 A | 3/1994 | Gevins |
| 5,339,826 A | 8/1994 | Schmidt et al. |
| 5,345,934 A | 9/1994 | Highe et al. |
| 5,355,883 A | 10/1994 | Ascher |
| 5,357,957 A | 10/1994 | Itil et al. |
| 5,363,858 A | 11/1994 | Farwell |
| 5,392,788 A | 2/1995 | Hudspeth |
| 5,406,956 A | 4/1995 | Farwell |
| 5,406,957 A | 4/1995 | Tansey |
| 5,447,166 A | 9/1995 | Gevins |
| 5,450,855 A | 9/1995 | Rosenfeld |
| 5,452,718 A | 9/1995 | Clare et al. |
| 5,474,082 A | 12/1995 | Junker |
| 5,479,934 A | 1/1996 | Imran |
| 5,513,649 A | 5/1996 | Gevins et al. |
| 5,518,007 A | 5/1996 | Becker |
| 5,537,618 A | 7/1996 | Boulton et al. |
| 5,579,774 A | 12/1996 | Miller et al. |
| 5,601,090 A | 2/1997 | Musha |
| 5,617,855 A | 4/1997 | Waletzky et al. |
| 5,645,577 A | 7/1997 | Froberg et al. |
| 5,649,061 A | 7/1997 | Smyth |
| 5,655,534 A | 8/1997 | Ilmoniemi |
| 5,676,138 A | 10/1997 | Zawilinski |
| 5,692,906 A | 12/1997 | Corder |
| 5,697,369 A | 12/1997 | Long, Jr. et al. |
| 5,720,619 A | 2/1998 | Fisslinger |
| 5,724,987 A | 3/1998 | Gevins et al. |
| 5,729,205 A | 3/1998 | Kwon |
| 5,736,986 A | 4/1998 | Sever, Jr. |
| 5,740,035 A | 4/1998 | Cohen et al. |
| 5,740,812 A | 4/1998 | Cowan |
| 5,762,611 A | 6/1998 | Lewis et al. |
| 5,771,897 A | 6/1998 | Zufrin |
| 5,772,591 A | 6/1998 | Cram |
| 5,774,591 A | 6/1998 | Black et al. |
| 5,787,187 A | 7/1998 | Bouchard et al. |
| 5,788,648 A | 8/1998 | Nadel |
| 5,800,351 A | 9/1998 | Mann |
| 5,812,642 A | 9/1998 | Leroy |
| 5,817,029 A | 10/1998 | Gevins et al. |
| 5,848,399 A | 12/1998 | Burke |
| 5,868,670 A | 2/1999 | Randell |
| 5,945,863 A | 8/1999 | Coy |
| 5,954,642 A | 9/1999 | Johnson et al. |
| 5,961,332 A | 10/1999 | Joao |
| 5,983,129 A | 11/1999 | Cowan et al. |
| 5,983,214 A | 11/1999 | Lang et al. |
| 6,001,065 A | 12/1999 | DeVito |
| 6,002,957 A | 12/1999 | Finneran |
| 6,021,346 A | 2/2000 | Ryu et al. |
| 6,052,619 A | 4/2000 | John |
| 6,099,319 A | 8/2000 | Zaltman et al. |
| 6,120,440 A | 9/2000 | Goknar |
| 6,128,521 A | 10/2000 | Marro et al. |
| 6,154,669 A | 11/2000 | Hunter et al. |
| 6,155,927 A | 12/2000 | Levasseur et al. |
| 6,161,030 A | 12/2000 | Levendowski et al. |
| 6,170,018 B1 | 1/2001 | Voll et al. |
| 6,171,239 B1 | 1/2001 | Humphrey |
| 6,173,260 B1 | 1/2001 | Slaney |
| 6,175,753 B1 | 1/2001 | Menkes et al. |
| 6,228,038 B1 | 5/2001 | Claessens |
| 6,233,472 B1 | 5/2001 | Bennett et al. |
| 6,236,885 B1 | 5/2001 | Hunter et al. |
| 6,254,536 B1 | 7/2001 | DeVito |
| 6,259,889 B1 | 7/2001 | LaDue |
| 6,280,198 B1 | 8/2001 | Calhoun et al. |
| 6,286,005 B1 | 9/2001 | Cannon |
| 6,289,234 B1 | 9/2001 | Mueller |
| 6,292,688 B1 | 9/2001 | Patton |
| 6,301,493 B1 | 10/2001 | Marro et al. |
| 6,309,342 B1 | 10/2001 | Blazey et al. |
| 6,315,569 B1 | 11/2001 | Zaltman |
| 6,322,368 B1 | 11/2001 | Young et al. |
| 6,330,470 B1 | 12/2001 | Tucker et al. |
| 6,334,778 B1 | 1/2002 | Brown |

(56) References Cited

U.S. PATENT DOCUMENTS

| | | |
|---|---|---|
| 6,349,231 B1 | 2/2002 | Musha |
| 6,374,143 B1 | 4/2002 | Berrang et al. |
| 6,381,481 B1 | 4/2002 | Levendowski et al. |
| 6,398,643 B1 | 6/2002 | Knowles et al. |
| 6,422,999 B1 | 7/2002 | Hill |
| 6,425,764 B1 | 7/2002 | Lamson |
| 6,434,419 B1 | 8/2002 | Gevins et al. |
| 6,453,194 B1 | 9/2002 | Hill |
| 6,481,013 B1 | 11/2002 | Dinwiddie et al. |
| 6,487,444 B2 | 11/2002 | Mimura |
| 6,488,617 B1 | 12/2002 | Katz |
| 6,510,340 B1 | 1/2003 | Jordan |
| 6,520,905 B1 | 2/2003 | Surve et al. |
| 6,545,685 B1 | 4/2003 | Dorbie |
| 6,574,513 B1 | 6/2003 | Collura et al. |
| 6,575,902 B1 | 6/2003 | Burton |
| 6,577,329 B1 | 6/2003 | Flickner et al. |
| 6,585,521 B1 | 7/2003 | Obrador |
| 6,594,521 B2 | 7/2003 | Tucker |
| 6,598,006 B1 | 7/2003 | Honda et al. |
| 6,606,102 B1 | 8/2003 | Odom |
| 6,606,519 B2 | 8/2003 | Powell |
| 6,609,024 B1 | 8/2003 | Ryu et al. |
| 6,623,428 B2 | 9/2003 | Miller et al. |
| 6,626,676 B2 | 9/2003 | Freer |
| 6,648,822 B2 | 11/2003 | Hamamoto et al. |
| 6,652,283 B1 | 11/2003 | Van Schaack et al. |
| 6,654,626 B2 | 11/2003 | Devlin et al. |
| 6,656,116 B2 | 12/2003 | Kim et al. |
| 6,662,052 B1 | 12/2003 | Sarwal et al. |
| 6,665,560 B2 | 12/2003 | Becker et al. |
| 6,678,866 B1 | 1/2004 | Sugimoto et al. |
| 6,688,890 B2 | 2/2004 | von Buegner |
| 6,699,188 B2 | 3/2004 | Wessel |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopenathan et al. |
| 6,788,882 B1 | 9/2004 | Geer et al. |
| 6,792,304 B1 | 9/2004 | Silberstein |
| 6,839,682 B1 | 1/2005 | Blume |
| 6,842,877 B2 | 1/2005 | Robarts et al. |
| 6,904,408 B1 | 6/2005 | McCarthy et al. |
| 6,915,148 B2 | 7/2005 | Finneran et al. |
| 6,950,698 B2 | 9/2005 | Sarkela et al. |
| 6,958,710 B2 | 10/2005 | Zhang et al. |
| 6,961,601 B2 | 11/2005 | Matthews et al. |
| 6,973,342 B1 | 12/2005 | Swanson |
| 6,978,115 B2 | 12/2005 | Whitehurst et al. |
| 6,993,380 B1 | 1/2006 | Modarres |
| 7,035,685 B2 | 4/2006 | Ryu et al. |
| 7,050,753 B2 | 5/2006 | Knutson |
| 7,113,916 B1 | 9/2006 | Hill |
| 7,120,880 B1 | 10/2006 | Dryer et al. |
| 7,127,283 B2 | 10/2006 | Kageyama |
| 7,130,673 B2 | 10/2006 | Tolvanen-Laakso et al. |
| 7,150,715 B2 | 12/2006 | Collura et al. |
| 7,164,967 B2 | 1/2007 | Etienne-Cummings et al. |
| 7,173,437 B2 | 2/2007 | Hervieux et al. |
| 7,177,675 B2 | 2/2007 | Suffin et al. |
| 7,194,186 B1 | 3/2007 | Strub et al. |
| 7,222,071 B2 | 5/2007 | Neuhauser et al. |
| 7,272,982 B2 | 9/2007 | Neuhauser et al. |
| 7,286,871 B2 | 10/2007 | Cohen |
| 7,340,060 B2 | 3/2008 | Tomkins et al. |
| D565,735 S | 4/2008 | Washbon |
| 7,359,744 B2 | 4/2008 | Lee et al. |
| 7,383,728 B2 | 6/2008 | Noble et al. |
| 7,391,835 B1 | 6/2008 | Gross et al. |
| 7,408,460 B2 | 8/2008 | Crystal et al. |
| 7,420,464 B2 | 9/2008 | Fitzgerald et al. |
| 7,440,789 B2 | 10/2008 | Hannula et al. |
| 7,443,292 B2 | 10/2008 | Jensen et al. |
| 7,443,693 B2 | 10/2008 | Arnold et al. |
| 7,460,827 B2 | 12/2008 | Schuster et al. |
| 7,463,143 B2 | 12/2008 | Forr et al. |
| 7,463,144 B2 | 12/2008 | Crystal et al. |
| 7,471,978 B2 | 12/2008 | John et al. |
| 7,471,987 B2 | 12/2008 | Crystal et al. |
| 7,483,835 B2 | 1/2009 | Neuhauser et al. |
| 7,496,400 B2 | 2/2009 | Hoskonen et al. |
| 7,548,774 B2 | 6/2009 | Kurtz et al. |
| 7,551,952 B2 | 6/2009 | Gevins et al. |
| 7,592,908 B2 | 9/2009 | Zhang et al. |
| 7,614,066 B2 | 11/2009 | Urdang et al. |
| 7,623,823 B2 | 11/2009 | Zito et al. |
| 7,627,880 B2 | 12/2009 | Itakura |
| 7,636,456 B2 | 12/2009 | Collins et al. |
| 7,650,793 B2 | 1/2010 | Jensen et al. |
| 7,672,717 B1 | 3/2010 | Zikov et al. |
| 7,689,272 B2 | 3/2010 | Farwell |
| 7,697,979 B2 | 4/2010 | Martinerie et al. |
| 7,698,238 B2 | 4/2010 | Barletta et al. |
| 7,715,894 B2 | 5/2010 | Dunseath et al. |
| 7,716,697 B2 | 5/2010 | Moriwaka et al. |
| 7,720,351 B2 | 5/2010 | Levitan |
| 7,729,755 B2 | 6/2010 | Laken |
| 7,739,140 B2 | 6/2010 | Vinson et al. |
| 7,742,623 B1 | 6/2010 | Moon et al. |
| 7,751,878 B1 | 7/2010 | Merkle et al. |
| 7,805,009 B2 | 9/2010 | Everett et al. |
| 7,809,420 B2 | 10/2010 | Hannula et al. |
| 7,840,248 B2 | 11/2010 | Fuchs et al. |
| 7,840,250 B2 | 11/2010 | Tucker |
| 7,853,122 B2 | 12/2010 | Miura et al. |
| 7,865,394 B1 | 1/2011 | Calloway |
| 7,892,764 B2 | 2/2011 | Xiong et al. |
| 7,908,133 B2 | 3/2011 | Neuhauser |
| 7,917,366 B1 | 3/2011 | Levanon et al. |
| 7,942,816 B2 | 5/2011 | Satoh et al. |
| 7,946,974 B2 | 5/2011 | Lordereau |
| 7,962,315 B2 | 6/2011 | Jensen et al. |
| 7,988,557 B2 | 8/2011 | Soderland |
| 8,014,847 B2 | 9/2011 | Shastri et al. |
| 8,027,518 B2 | 9/2011 | Baker et al. |
| 8,055,722 B2 | 11/2011 | Hille |
| 8,069,125 B2 | 11/2011 | Jung et al. |
| 8,082,215 B2 | 12/2011 | Jung et al. |
| 8,086,563 B2 | 12/2011 | Jung et al. |
| 8,098,152 B2 | 1/2012 | Zhang et al. |
| 8,103,328 B2 | 1/2012 | Turner et al. |
| 8,112,141 B2 | 2/2012 | Wilson et al. |
| 8,135,606 B2 | 3/2012 | Dupree |
| 8,151,298 B2 | 4/2012 | Begeja et al. |
| 8,165,916 B2 | 4/2012 | Hoffberg et al. |
| 8,179,604 B1 | 5/2012 | Prada Gomez et al. |
| 8,209,224 B2 | 6/2012 | Pradeep et al. |
| 8,229,469 B2 | 7/2012 | Zhang et al. |
| 8,239,030 B1 | 8/2012 | Hagedorn et al. |
| 8,255,267 B2 | 8/2012 | Breiter |
| 8,270,814 B2 | 9/2012 | Pradeep et al. |
| 8,290,563 B2 | 10/2012 | Jin et al. |
| 8,300,526 B2 | 10/2012 | Saito et al. |
| 8,326,396 B2 | 12/2012 | Picht et al. |
| 8,327,395 B2 | 12/2012 | Lee |
| 8,332,883 B2 | 12/2012 | Lee |
| 8,335,715 B2 | 12/2012 | Pradeep et al. |
| 8,386,312 B2 | 2/2013 | Pradeep et al. |
| 8,386,313 B2 | 2/2013 | Pradeep et al. |
| 8,388,165 B2 | 3/2013 | Zhang |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,396,744 B2 | 3/2013 | Pradeep et al. |
| 8,442,429 B2 | 5/2013 | Hawit |
| 8,467,133 B2 | 6/2013 | Miller |
| 8,473,345 B2 | 6/2013 | Pradeep et al. |
| 8,477,425 B2 | 7/2013 | Border et al. |
| 8,484,081 B2 | 7/2013 | Pradeep et al. |
| 8,494,610 B2 | 7/2013 | Pradeep et al. |
| 8,494,905 B2 | 7/2013 | Pradeep et al. |
| 8,533,042 B2 | 9/2013 | Pradeep et al. |

(56) References Cited

U.S. PATENT DOCUMENTS

| | | |
|---|---|---|
| 8,548,554 B2 | 10/2013 | Popescu et al. |
| 8,548,852 B2 | 10/2013 | Pradeep et al. |
| 8,635,105 B2 | 1/2014 | Pradeep et al. |
| 8,655,428 B2 | 2/2014 | Pradeep et al. |
| 8,655,437 B2 | 2/2014 | Pradeep et al. |
| 2001/0016874 A1 | 8/2001 | Ono et al. |
| 2001/0020236 A1 | 9/2001 | Cannon |
| 2001/0029468 A1 | 10/2001 | Yamaguchi et al. |
| 2001/0056225 A1 | 12/2001 | DeVito |
| 2002/0065826 A1 | 5/2002 | Bell et al. |
| 2002/0072952 A1 | 6/2002 | Hamzey et al. |
| 2002/0077534 A1 | 6/2002 | DuRousseau |
| 2002/0107454 A1 | 8/2002 | Collura et al. |
| 2002/0143627 A1 | 10/2002 | Barsade et al. |
| 2002/0154833 A1 | 10/2002 | Koch et al. |
| 2002/0155878 A1 | 10/2002 | Led, Jr. et al. |
| 2002/0156842 A1 | 10/2002 | Signes et al. |
| 2002/0182574 A1 | 12/2002 | Freer |
| 2002/0188216 A1 | 12/2002 | Kayyali et al. |
| 2002/0188217 A1 | 12/2002 | Farwell |
| 2002/0193670 A1 | 12/2002 | Garfield et al. |
| 2003/0003433 A1 | 1/2003 | Carpenter et al. |
| 2003/0013981 A1 | 1/2003 | Gevins et al. |
| 2003/0036955 A1 | 2/2003 | Tanaka et al. |
| 2003/0055355 A1 | 3/2003 | Vieritio-Oja |
| 2003/0059750 A1 | 3/2003 | Bindler et al. |
| 2003/0063780 A1 | 4/2003 | Gutta et al. |
| 2003/0066071 A1 | 4/2003 | Gutta et al. |
| 2003/0067486 A1 | 4/2003 | Lee et al. |
| 2003/0073921 A1 | 4/2003 | Sohmer et al. |
| 2003/0076369 A1 | 4/2003 | Resner |
| 2003/0081834 A1 | 5/2003 | Philomin et al. |
| 2003/0093784 A1 | 5/2003 | Dimitrova et al. |
| 2003/0100998 A2 | 5/2003 | Brunner et al. |
| 2003/0104865 A1 | 6/2003 | Itkis et al. |
| 2003/0126593 A1 | 7/2003 | Mault |
| 2003/0153841 A1 | 8/2003 | Kilborn et al. |
| 2003/0165270 A1 | 9/2003 | Endrikhovski et al. |
| 2003/0177488 A1 | 9/2003 | Smith et al. |
| 2003/0233278 A1 | 12/2003 | Marshall |
| 2004/0005143 A1 | 1/2004 | Tsuru et al. |
| 2004/0013398 A1 | 1/2004 | Miura et al. |
| 2004/0015608 A1 | 1/2004 | Ellis et al. |
| 2004/0018476 A1 | 1/2004 | Ladue |
| 2004/0039268 A1 | 2/2004 | Barbour et al. |
| 2004/0044382 A1 | 3/2004 | Ibrahim |
| 2004/0072133 A1 | 4/2004 | Kullock et al. |
| 2004/0073129 A1 | 4/2004 | Caldwell et al. |
| 2004/0077934 A1 | 4/2004 | Massad |
| 2004/0088289 A1 | 5/2004 | Xu et al. |
| 2004/0092809 A1 | 5/2004 | DeCharms |
| 2004/0098298 A1 | 5/2004 | Yin |
| 2004/0111033 A1 | 6/2004 | Oung et al. |
| 2004/0138580 A1 | 7/2004 | Frei et al. |
| 2004/0138581 A1 | 7/2004 | Frei et al. |
| 2004/0161730 A1 | 8/2004 | Urman |
| 2004/0187167 A1 | 9/2004 | Maguire et al. |
| 2004/0193068 A1 | 9/2004 | Burton et al. |
| 2004/0208496 A1 | 10/2004 | Pilu |
| 2004/0210159 A1 | 10/2004 | Kibar et al. |
| 2004/0220483 A1 | 11/2004 | Yeo et al. |
| 2004/0236623 A1 | 11/2004 | Gopalakrishnan |
| 2004/0267141 A1 | 12/2004 | Amano et al. |
| 2005/0010087 A1 | 1/2005 | Banet |
| 2005/0010116 A1 | 1/2005 | Korhonen et al. |
| 2005/0010475 A1 | 1/2005 | Perkowski et al. |
| 2005/0043774 A1 | 2/2005 | Devlin et al. |
| 2005/0045189 A1 | 3/2005 | Jay |
| 2005/0066307 A1 | 3/2005 | Patel et al. |
| 2005/0071865 A1 | 3/2005 | Martins |
| 2005/0076359 A1 | 4/2005 | Pierson et al. |
| 2005/0079474 A1 | 4/2005 | Lowe |
| 2005/0096311 A1 | 5/2005 | Suffin et al. |
| 2005/0097594 A1 | 5/2005 | O'Donnell et al. |
| 2005/0107716 A1 | 5/2005 | Eaton et al. |
| 2005/0113656 A1 | 5/2005 | Chance |
| 2005/0120372 A1 | 6/2005 | Itakura |
| 2005/0143629 A1 | 6/2005 | Farwell |
| 2005/0154290 A1 | 7/2005 | Langleben |
| 2005/0165285 A1 | 7/2005 | Iliff |
| 2005/0172311 A1 | 8/2005 | Hjelt et al. |
| 2005/0177058 A1 | 8/2005 | Sobell |
| 2005/0197556 A1 | 9/2005 | Stoler |
| 2005/0197590 A1 | 9/2005 | Osorio et al. |
| 2005/0203798 A1 | 9/2005 | Jensen et al. |
| 2005/0215916 A1 | 9/2005 | Fadem et al. |
| 2005/0223237 A1 | 10/2005 | Barletta et al. |
| 2005/0227233 A1 | 10/2005 | Buxton et al. |
| 2005/0240956 A1 | 10/2005 | Smith et al. |
| 2005/0272017 A1 | 12/2005 | Neuhauser et al. |
| 2005/0273017 A1 | 12/2005 | Gordon |
| 2005/0273802 A1 | 12/2005 | Crystal et al. |
| 2005/0288954 A1 | 12/2005 | McCarthy et al. |
| 2005/0289582 A1 | 12/2005 | Tavares et al. |
| 2006/0003732 A1 | 1/2006 | Neuhauser et al. |
| 2006/0010470 A1 | 1/2006 | Kurosaki et al. |
| 2006/0035707 A1 | 2/2006 | Nguyen et al. |
| 2006/0053110 A1 | 3/2006 | McDonald et al. |
| 2006/0064037 A1 | 3/2006 | Shalon et al. |
| 2006/0093998 A1 | 5/2006 | Vertegaal |
| 2006/0094970 A1 | 5/2006 | Drew |
| 2006/0111044 A1 | 5/2006 | Keller |
| 2006/0111621 A1 | 5/2006 | Coppi et al. |
| 2006/0111644 A1 | 5/2006 | Guttag et al. |
| 2006/0129458 A1 | 6/2006 | Maggio |
| 2006/0143647 A1 | 6/2006 | Bill |
| 2006/0167376 A1 | 7/2006 | Viirre et al. |
| 2006/0168613 A1 | 7/2006 | Wood et al. |
| 2006/0168630 A1 | 7/2006 | Davies |
| 2006/0173510 A1 | 8/2006 | Besio et al. |
| 2006/0189900 A1 | 8/2006 | Flaherty |
| 2006/0217598 A1 | 9/2006 | Miyajima et al. |
| 2006/0256133 A1 | 11/2006 | Rosenberg |
| 2006/0257834 A1 | 11/2006 | Lee et al. |
| 2006/0258926 A1 | 11/2006 | Ali et al. |
| 2006/0259360 A1 | 11/2006 | Flinn et al. |
| 2006/0265022 A1 | 11/2006 | John et al. |
| 2006/0277102 A1 | 12/2006 | Agliozzo |
| 2006/0293608 A1 | 12/2006 | Rothman et al. |
| 2006/0293921 A1 | 12/2006 | McCarthy et al. |
| 2007/0031798 A1 | 2/2007 | Gottfried |
| 2007/0048707 A1 | 3/2007 | Caamano et al. |
| 2007/0053513 A1 | 3/2007 | Hoffberg |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066874 A1 | 3/2007 | Cook |
| 2007/0066914 A1 | 3/2007 | Le et al. |
| 2007/0066915 A1 | 3/2007 | Frei et al. |
| 2007/0066916 A1 | 3/2007 | Lemos |
| 2007/0067007 A1 | 3/2007 | Schulman et al. |
| 2007/0067305 A1 | 3/2007 | Ives |
| 2007/0078706 A1 | 4/2007 | Datta et al. |
| 2007/0079331 A1 | 4/2007 | Datta et al. |
| 2007/0101360 A1 | 5/2007 | Gutta et al. |
| 2007/0106170 A1 | 5/2007 | Dunseath, Jr. et al. |
| 2007/0116037 A1 | 5/2007 | Moore |
| 2007/0135727 A1 | 6/2007 | Virtanen et al. |
| 2007/0135728 A1 | 6/2007 | Snyder et al. |
| 2007/0168461 A1 | 7/2007 | Moore |
| 2007/0173733 A1 | 7/2007 | Le et al. |
| 2007/0179396 A1 | 8/2007 | Le et al. |
| 2007/0184420 A1 | 8/2007 | Mathan et al. |
| 2007/0225585 A1 | 9/2007 | Washbon et al. |
| 2007/0225674 A1 | 9/2007 | Molnar et al. |
| 2007/0226760 A1 | 9/2007 | Neuhauser et al. |
| 2007/0235716 A1 | 10/2007 | Delic et al. |
| 2007/0238945 A1 | 10/2007 | Delic et al. |
| 2007/0249952 A1 | 10/2007 | Rubin et al. |
| 2007/0250846 A1 | 10/2007 | Swix et al. |
| 2007/0255127 A1 | 11/2007 | Mintz et al. |
| 2007/0265507 A1 | 11/2007 | de Lemos |
| 2007/0294132 A1 | 12/2007 | Zhang et al. |
| 2007/0294705 A1 | 12/2007 | Gopalakrishnan |

(56) References Cited

U.S. PATENT DOCUMENTS

| | | |
|---|---|---|
| 2007/0294706 A1 | 12/2007 | Neuhauser et al. |
| 2008/0001600 A1 | 1/2008 | deCharms |
| 2008/0010110 A1 | 1/2008 | Neuhauser et al. |
| 2008/0027345 A1 | 1/2008 | Kumada et al. |
| 2008/0039737 A1 | 2/2008 | Breiter et al. |
| 2008/0040740 A1 | 2/2008 | Plotnick et al. |
| 2008/0059997 A1 | 3/2008 | Plotnick et al. |
| 2008/0065468 A1 | 3/2008 | Berg et al. |
| 2008/0065721 A1 | 3/2008 | Cragun |
| 2008/0081961 A1 | 4/2008 | Westbrook et al. |
| 2008/0082019 A1 | 4/2008 | Ludving et al. |
| 2008/0082020 A1 | 4/2008 | Collura |
| 2008/0086356 A1 | 4/2008 | Glassman et al. |
| 2008/0091512 A1 | 4/2008 | Marci et al. |
| 2008/0097854 A1 | 4/2008 | Young |
| 2008/0109840 A1 | 5/2008 | Walter et al. |
| 2008/0125110 A1 | 5/2008 | Ritter |
| 2008/0127978 A1 | 6/2008 | Rubin et al. |
| 2008/0144882 A1 | 6/2008 | Leinbach et al. |
| 2008/0147488 A1 | 6/2008 | Tunick et al. |
| 2008/0152300 A1 | 6/2008 | Knee et al. |
| 2008/0159365 A1 | 7/2008 | Dubocanin et al. |
| 2008/0162182 A1 | 7/2008 | Cazares et al. |
| 2008/0177197 A1 | 7/2008 | Lee et al. |
| 2008/0201731 A1 | 8/2008 | Howcraft |
| 2008/0204273 A1 | 8/2008 | Crystal et al. |
| 2008/0208072 A1 | 8/2008 | Fadem et al. |
| 2008/0211768 A1 | 9/2008 | Breen et al. |
| 2008/0214902 A1 | 9/2008 | Lee et al. |
| 2008/0218472 A1 | 9/2008 | Breen et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0228077 A1 | 9/2008 | Wilk et al. |
| 2008/0255949 A1 | 10/2008 | Genco et al. |
| 2008/0295126 A1 | 11/2008 | Lee et al. |
| 2008/0306398 A1 | 12/2008 | Uchiyama et al. |
| 2008/0312523 A1 | 12/2008 | Dunseath |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0025024 A1 | 1/2009 | Beser et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030762 A1 | 1/2009 | Lee et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0037575 A1 | 2/2009 | Crystal et al. |
| 2009/0060240 A1 | 3/2009 | Coughlan et al. |
| 2009/0062629 A1 | 3/2009 | Pradeep et al. |
| 2009/0062679 A1 | 3/2009 | Tan et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0069652 A1 | 3/2009 | Lee et al. |
| 2009/0070798 A1 | 3/2009 | Lee et al. |
| 2009/0082643 A1 | 3/2009 | Pradeep et al. |
| 2009/0082689 A1 | 3/2009 | Guttag et al. |
| 2009/0083129 A1 | 3/2009 | Pradeep et al. |
| 2009/0088610 A1 | 4/2009 | Lee et al. |
| 2009/0089830 A1 | 4/2009 | Chandratillake et al. |
| 2009/0094286 A1 | 4/2009 | Lee et al. |
| 2009/0094627 A1 | 4/2009 | Lee et al. |
| 2009/0094628 A1 | 4/2009 | Lee et al. |
| 2009/0094629 A1 | 4/2009 | Lee et al. |
| 2009/0097689 A1 | 4/2009 | Prest et al. |
| 2009/0105576 A1 | 4/2009 | Do et al. |
| 2009/0112077 A1 | 4/2009 | Nguyen et al. |
| 2009/0112281 A1 | 4/2009 | Miyazawa et al. |
| 2009/0119154 A1 | 5/2009 | Jung et al. |
| 2009/0131764 A1 | 5/2009 | Lee et al. |
| 2009/0133047 A1 | 5/2009 | Lee et al. |
| 2009/0150919 A1 | 6/2009 | Lee et al. |
| 2009/0156925 A1 | 6/2009 | Jin et al. |
| 2009/0158308 A1 | 6/2009 | Weitzenfeld et al. |
| 2009/0163777 A1 | 6/2009 | Jung |
| 2009/0195392 A1 | 8/2009 | Zalewski |
| 2009/0214060 A1 | 8/2009 | Chuang et al. |
| 2009/0222330 A1 | 9/2009 | Leinbach |
| 2009/0248484 A1 | 10/2009 | Surendran et al. |
| 2009/0248496 A1 | 10/2009 | Hueter et al. |
| 2009/0253996 A1 | 10/2009 | Lee et al. |
| 2009/0259137 A1 | 10/2009 | Delic et al. |
| 2009/0271122 A1 | 10/2009 | Hyde et al. |
| 2009/0292587 A1 | 11/2009 | Fitzgerald |
| 2009/0295738 A1 | 12/2009 | Chiang |
| 2009/0318773 A1 | 12/2009 | Jung et al. |
| 2009/0318826 A1 | 12/2009 | Green et al. |
| 2009/0327068 A1 | 12/2009 | Pradeep et al. |
| 2009/0328089 A1 | 12/2009 | Pradeep et al. |
| 2010/0004977 A1 | 1/2010 | Marci et al. |
| 2010/0022821 A1 | 1/2010 | Dubi et al. |
| 2010/0041962 A1 | 2/2010 | Causevic et al. |
| 2010/0042012 A1 | 2/2010 | Alhussiny |
| 2010/0060300 A1 | 3/2010 | Muller et al. |
| 2010/0075532 A1 | 3/2010 | Copp-Howland et al. |
| 2010/0076333 A9 | 3/2010 | Burton et al. |
| 2010/0125190 A1 | 5/2010 | Fadem |
| 2010/0125219 A1 | 5/2010 | Harris et al. |
| 2010/0145176 A1 | 6/2010 | Himes |
| 2010/0145215 A1 | 6/2010 | Pradeep et al. |
| 2010/0145217 A1 | 6/2010 | Otto et al. |
| 2010/0180029 A1 | 7/2010 | Fourman |
| 2010/0183279 A1 | 7/2010 | Pradeep et al. |
| 2010/0186031 A1 | 7/2010 | Pradeep et al. |
| 2010/0186032 A1 | 7/2010 | Pradeep et al. |
| 2010/0198042 A1 | 8/2010 | Popescu et al. |
| 2010/0214318 A1 | 8/2010 | Pradeep et al. |
| 2010/0215289 A1 | 8/2010 | Pradeep et al. |
| 2010/0218208 A1 | 8/2010 | Holden |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0250458 A1 | 9/2010 | Ho |
| 2010/0257052 A1 | 10/2010 | Zito et al. |
| 2010/0268540 A1 | 10/2010 | Arshi et al. |
| 2010/0268573 A1 | 10/2010 | Jain et al. |
| 2010/0269127 A1 | 10/2010 | Krug |
| 2010/0274152 A1 | 10/2010 | McPeck et al. |
| 2010/0274153 A1 | 10/2010 | Tucker et al. |
| 2010/0306120 A1 | 12/2010 | Ciptawilangga |
| 2010/0317988 A1 | 12/2010 | Terada et al. |
| 2010/0325660 A1 | 12/2010 | Holden |
| 2010/0331661 A1 | 12/2010 | Nakagawa |
| 2011/0004089 A1 | 1/2011 | Chou |
| 2011/0015503 A1 | 1/2011 | Joffe et al. |
| 2011/0040202 A1 | 2/2011 | Luo et al. |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047121 A1 | 2/2011 | Pradeep et al. |
| 2011/0059422 A1 | 3/2011 | Masaoka |
| 2011/0085700 A1 | 4/2011 | Lee |
| 2011/0098593 A1 | 4/2011 | Low et al. |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0131274 A1 | 6/2011 | Hille |
| 2011/0144519 A1 | 6/2011 | Causevic |
| 2011/0151728 A1 | 6/2011 | Astola |
| 2011/0153391 A1 | 6/2011 | Tenbrock |
| 2011/0161163 A1 | 6/2011 | Carlson et al. |
| 2011/0161790 A1 | 6/2011 | Junior et al. |

(56) References Cited

U.S. PATENT DOCUMENTS

| | | |
|---|---|---|
| 2011/0191142 A1 | 8/2011 | Huang |
| 2011/0208515 A1 | 8/2011 | Neuhauser |
| 2011/0224569 A1 | 9/2011 | Isenhart et al. |
| 2011/0224570 A1 | 9/2011 | Causevic |
| 2011/0237923 A1 | 9/2011 | Picht et al. |
| 2011/0237971 A1 | 9/2011 | Pradeep et al. |
| 2011/0248729 A2 | 10/2011 | Mueller et al. |
| 2011/0257502 A1 | 10/2011 | Lee |
| 2011/0257937 A1 | 10/2011 | Lee |
| 2011/0270620 A1 | 11/2011 | Pradeep et al. |
| 2011/0276504 A1 | 11/2011 | Pradeep et al. |
| 2011/0282231 A1 | 11/2011 | Pradeep et al. |
| 2011/0282232 A1 | 11/2011 | Pradeep et al. |
| 2011/0282749 A1 | 11/2011 | Pradeep et al. |
| 2011/0298706 A1 | 12/2011 | Mann |
| 2011/0301431 A1 | 12/2011 | Greicius |
| 2011/0319975 A1 | 12/2011 | Ho et al. |
| 2012/0003862 A1 | 1/2012 | Newman et al. |
| 2012/0004899 A1 | 1/2012 | Arshi |
| 2012/0022391 A1 | 1/2012 | Leuthardt |
| 2012/0036004 A1 | 2/2012 | Pradeep et al. |
| 2012/0036005 A1 | 2/2012 | Pradeep et al. |
| 2012/0054018 A1 | 3/2012 | Pradeep et al. |
| 2012/0072289 A1 | 3/2012 | Pradeep et al. |
| 2012/0096363 A1 | 4/2012 | Barnes et al. |
| 2012/0108995 A1 | 5/2012 | Pradeep et al. |
| 2012/0114305 A1 | 5/2012 | Holden |
| 2012/0130800 A1 | 5/2012 | Pradeep et al. |
| 2012/0143020 A1 | 6/2012 | Bordoley et al. |
| 2012/0173701 A1 | 7/2012 | Tenbrock |
| 2012/0203363 A1 | 8/2012 | McKenna et al. |
| 2012/0203559 A1 | 8/2012 | McKenna et al. |
| 2012/0239407 A1 | 9/2012 | Jain et al. |
| 2012/0245978 A1 | 9/2012 | Crystal et al. |
| 2012/0249797 A1 | 10/2012 | Haddick et al. |
| 2013/0024272 A1 | 1/2013 | Pradeep et al. |
| 2013/0060125 A1 | 3/2013 | Zeman |
| 2013/0166373 A1 | 6/2013 | Pradeep et al. |
| 2013/0185140 A1 | 7/2013 | Pradeep et al. |
| 2013/0185141 A1 | 7/2013 | Pradeep et al. |
| 2013/0185142 A1 | 7/2013 | Pradeep et al. |
| 2013/0185144 A1 | 7/2013 | Pradeep et al. |
| 2013/0185145 A1 | 7/2013 | Pradeep et al. |
| 2013/0311132 A1 | 11/2013 | Tobita |
| 2013/0332259 A1 | 12/2013 | Pradeep et al. |

FOREIGN PATENT DOCUMENTS

| | | |
|---|---|---|
| EP | 1052582 | 11/2000 |
| EP | 1389012 | 2/2004 |
| EP | 1607842 | 12/2005 |
| FR | 2627975 | 9/1989 |
| GB | 1374658 | 11/1974 |
| GB | 2221759 | 2/1990 |
| JP | 05-293172 | 11/1993 |
| JP | 07-329657 | 12/1995 |
| JP | 2002-000577 | 1/2002 |
| JP | 2002-056500 | 2/2002 |
| JP | 2002-344904 | 11/2002 |
| JP | 2003-016095 | 1/2003 |
| JP | 2003-111106 | 4/2003 |
| JP | 2003-178078 | 6/2003 |
| JP | 2003-522580 | 7/2003 |
| JP | 2005-160805 | 12/2003 |
| JP | 2005261076 | 9/2005 |
| JP | 2005-084770 | 3/2006 |
| JP | 2006-305334 | 3/2006 |
| JP | 2006-323547 | 11/2006 |
| KR | 10-2000-0072489 | 12/2000 |
| KR | 10-2001-0104579 | 11/2001 |
| KR | 20120129870 | 11/2012 |
| WO | 95-018565 | 7/1995 |
| WO | 1997-017774 | 5/1997 |
| WO | 1997-040745 | 11/1997 |
| WO | 1997-041673 | 11/1997 |
| WO | 00/17824 | 3/2000 |
| WO | 01/97070 | 12/2001 |
| WO | 02-100241 | 12/2002 |
| WO | 02-102238 | 12/2002 |
| WO | 02100267 | 12/2002 |
| WO | 2004-034881 | 4/2004 |
| WO | 2004-049225 | 6/2004 |
| WO | 2004/100765 | 11/2004 |
| WO | 2006/005767 | 1/2006 |
| WO | 2007/019584 | 2/2007 |
| WO | 2008-077178 | 7/2008 |
| WO | 2008-109694 | 9/2008 |
| WO | 2008-109699 | 9/2008 |
| WO | 2008-121651 | 10/2008 |
| WO | 2008-141340 | 10/2008 |
| WO | 2008-137579 | 11/2008 |
| WO | 2008-137581 | 11/2008 |
| WO | 2008-154410 | 12/2008 |
| WO | 2009-018374 | 2/2009 |
| WO | 2009-052833 | 4/2009 |
| WO | 2011-055291 | 5/2011 |
| WO | 2011-056679 | 5/2011 |

OTHER PUBLICATIONS

Notification to Grant Patent Right for Invention, issued by the State Intellectual Property Office of the P.R. China, in connection with Chinese Patent Application No. 201310471815.3, dated Feb. 5, 2016, 2 pages.

Communication Pursuant to Article 94(3) EPC, issued by the European Patent Office in connection with European Patent Application No. 13004052.0, dated Feb. 17, 2016, 6 pages.

Aaker et al., "Warmth in Advertising: Measurement, Impact, and Sequence Effects," Journal of Consumer Research, vol. 12, No. 4, pp. 365-381, Mar. 1986, 18 pages.

Adamic et al., "The political blogosphere and the 2004 U.S. election: Divided they blog," Proceedings WWW-2005 2nd Annual Workshop on the Weblogging Ecosystem, 2005, Chiba, Japan, 16 pages.

Adar et al., "Implicit structure and the dynamics of blogspace," Proceedings WWW-2004 Workshop on the Weblogging Ecosystem, 2004, New York, NY, 8 pages.

Akam, et al., "Oscillations and Filtering Networks Support Flexible Routing of Information," Neuron, vol. 67, pp. 308-320, Elsevier, Jul. 29, 2010, 13 pages.

Aliod et al., "A Real World Implementation of Answer Extraction," Department of Computer Science, University of Zurich, Winterthurerstr. 190, CH-8057 Zurich, Switzerland, 1998, 6 pages.

Allen et al., "A Method of Removing Imaging Artifact from Continuous EEG Recorded during Functional MRI," Neuroimage, vol. 12, 230-239, Aug. 2000, 12 pages.

Ambler, "Salience and Choice: Neural Correlates of Shopping Decisions," Psychology & Marketing, vol. 21, No. 4, p. 247-261, Wiley Periodicals, Inc., doi: 10.1002/mar20004, Apr. 2004, 16 pages.

Ambler et al., "Ads on the Brain; A Neuro-Imaging Comparison of Cognitive and Affective Advertising Stimuli," London Business School, Centre for Marketing Working Paper, No. 00-902, Mar. 2000, 23 pages.

Badre, et al. "Frontal Cortex and the Discovery of Abstract Action Rules," Neuron, vol. 66, pp. 315-326, Elsevier, Apr. 29, 2010, 12 pages.

Bagozzi et al., "The Role of Emotions in Marketing," Journal of the Academy of Marketing Science, vol. 27, No. 2, pp. 184-206, Academy of Marketing Science, 1999, 23 pages.

Barcelo, et al., "Prefrontal modulation of visual processing in humans," Nature Neuroscience, vol. 3, No. 4, Nature America, http//neurosci.nature.com, Apr. 2000, 5 pages.

Barreto et al., "Physiologic Instrumentation for Real-time Monitoring of Affective State of Computer Users," WSEAS International Conference on Instrumentation, Measurement, Control, Circuits and Systems (IMCAAS), 2004, 6 pages.

(56) References Cited

OTHER PUBLICATIONS

Beaver, John D., et al., "Individual Differences in Reward Drive Predict Neural Responses to Images of Food", J. of Neuroscience, (May 10, 2006), 5160-5166, 7 pages.

Belch et al., "Psychophysiological and Cognitive Responses to Sex in Advertising," Advances in Consumer Research, vol. 9, pp. 424-427, 1982, 6 pages.

Bimler et al., "Categorical perception of facial expressions of emotion: Evidence from multidimensional scaling," Cognition and Emotion, vol. 15(5), pp. 633-658 Sep. 2001, 26 pages.

Bishop, Mike, "Arrow Question/Answering Systems," Language Computer Corporation, 1999, 3 pages.

Bizrate, archived version of www.bizrate.com, Jan. 1999, 22 pages.

Blakeslee, "If You Have a 'Buy Button' in Your Brain, What Pushes It?" The New York Times, www.nytimes.com, Oct. 19, 2004, 3 pages.

Blum, "Empirical Support for Winnow and Weighted-Majority Algorithms: Results on a Calendar Scheduling Domain," in Machine Learning, vol. 26, Kluwer Academic Publishers, Boston, USA, 1997, 19 pages.

Bournellis, Cynthia, "Tracking the hits on Web Sites," Communications International: vol. 22, Issue 9, London, Sep. 1995, 3 pages.

Braeutigam, "Neuroeconomics-From neural systems to economic behavior," Brain Research Bulletin, vol. 67, pp. 355-360, Elsevier, 2005, 6 pages.

Buschman, et al., "Top-Down versus Bottom-Up Control of Attention in the Prefrontal and posterior Parietal Cortices," Science, vol. 315, www.sciencemag.org/cgi/content/full/315/5820/1860, American Association for the Advancement of Science, 2007, 4 pages.

Buschman, et al., "Serial, Covert Shifts of Attention during Visual Search Are Reflected by the Frontal Eye Fields and Correlated with Population Oscillations," Neuron, vol. 63, pp. 386-396, Elsevier, Aug. 13, 2009, 11 pages.

Canolty, et al., "High Gamma Power Is Phase-Locked to Theta Oscillations in Human Neocortex," Science, vol. 313, www.sciencemag.org, Sep. 15, 2006, 3 pages.

Chaum et al., "A Secure and Privacy-Protecting Protocol for Transmitting Personal Information Between Organizations," A.M. Odlyzko (Ed.): Advances in Cryptology, CRYPTO '86, LNCS 263, 1987, 51 pages.

Chaum, David L., "Untraceable Electronic Mail, Return Addresses and Digital Pseudonyms," Communication of the ACM, vol. 24, No. 2, 1981, 5 pages.

Carter, R., "Mapping the Mind," 1998, University of California Press, Berkeley, 3 pages.

Cheng, et al. "Gender Differences in the Mu Rhythm of the Human Mirror-Neuron System," PLos ONE, vol. 3, Issue 5, www.plosone.org, May 2008, 7 pages.

Clarke, Adam R. et al., "Eeg Analysis of Children with Attention-Deficit/Hyperactivity Disorder and Comorbid Reading Disabilities," Journal of Learning Disabilities, vol. 35, No. 3, May-Jun. 2002, 10 pages.

Clemons, "Resonance Marketing in the Age of the Truly Informed Consumer: Creating Profits through Differentiation and Delight," Wharton Information Strategy & Economics Blog 2, available at http://opim.wharton.upenn.edu/-clemons/blogs/resonanceblog.pdf, Mar. 28, 2007, 8 pages.

Clifford, "Billboards That Look Back," The New York Times, NYTimes.com, available at http://www.nytimes.com/2008/05/31/business/media/31billboard.html, May 31, 2008, 4 pages.

Coan et al., "Voluntary Facial Expression and Hemispheric Asymmetry Over the Frontal Cortex," Psycophysiology (Nov. 2001), 912-924, 14 pages.

Cohen, William W., "Data Integration using similarity joins and a word-based information representation language," ACM Transactions on Information Systems, vol. 18, No. 3, Jul. 2000, 34 pages.

Cohn et al., "Active Learning with Statistical Models," Journal of Artificial Intelligence Research 4, AI Access Foundation and Morgan Kaufmann Publishers, USA, 1996, 17 pages.

Crawford et al., "Self-generated happy and sad emotions in low and highly hypnotizable persons during waking and hypnosis: laterality and regional EEG activity differences," International Journal of Psychophysiology, vol. 24, pp. 239-266, Dec. 1996, 28 pages.

Dagan et al., "Mistake-Driven Learning in Text Categorization," in EMNLP '97, 2nd Conference on Empirical Methods in Natural Language Processing, 1997, 9 pages.

Davidson, et al., "The functional neuroanatomy of emotion and affective style," TRENDS in Cognitive Sciences, vol. 3, No. 1, Jan. 1999, 11 pages.

de Gelder et al., "Categorical Perception of Facial Expressions: Categories and their Internal Structure," Cognition and Emotion, vol. 11(1), pp. 1-23 1997, 23 pages.

D'Esposito, "From cognitive to neural models of working memory," Phil. Trans. R. Soc. B, doi: 10.1098/rstb.2007.2086, Mar. 30, 2007, 12 pages.

Delahaye group, "Delahaye Group to Offer Nets Bench: High Level Web-Site Qualitative Analysis and Reporting; NetBench Builds on Systems provided by I/PRO and Internet Media Services," 1995 Business Wire, Inc., May 31, 1995, 3 pages.

Desmet, "Measuring Emotions: Development to Products," to be published in Funology: From and Application of an Instrument to Measure Emotional Responses Usability to Enjoyment, pp. 111-123, Kluwer Academic Publishers, (Blythe et al., eds., 2004), 13 pages.

Dialogic, www.dialogic.com as archived on May 12, 2000, 34 pages.

Dien, et al., "Application of Repeated Measures ANOVA to High-Dens Dataset: A Review and Tutorial," in Event-Related Potentials: A Methods Handbook pp. 57-82, (Todd C. Handy, ed., 2005), 14 pages.

Dillon et al., "Marketing research in a Marketing Environment," Times Mirror/Mosby College, USA, 1987, 5 pages.

Duchowski, "A Breadth-First Survey of Eye-tracking Applications," Beahavior Research Methods, Instruments, and Computers (Nov. 2002), 455-470, 16 pages.

Edgar, et al., "Digital Filters in ERP Research," in Event-Related Potentials: A Methods Handbook pp. 85-113, (Todd C. Handy, ed., 2005), 15 pages.

EEG Protocols, "Protocols for EEG Recording," retrieved from the Internet on Aug. 23, 2011, http://www.q-metrix.com/EEGrecordingProtocols.pdf, Nov. 13, 2007, 3 pages.

Egner et al., "EEG Signature and Phenomenology of Alpha/theta Neurofeedback Training Versus Mock Feedback," Applied Psychophysiology and Biofeedback, vol. 27, No. 4, Dec. 2002, 10 pages.

El-Bab, M., "Congnative event related potentials during a learning task," Doctoral Dissertation, Faculty of Medicine, University of Southamption, 2001, 25 pages.

Engel et al., "Dynamic Predictions: Oscillations and Synchrony in Top-down Processing," Nature Reviews: Neuroscience, vol. 2, pp. 704-716, Macmillian Magazines Ltd., Oct. 2001, 13 pages.

Ewatch, eWatch's archived web site retrieved from [URL: http://web.archive.org/web/19980522190526/wwww.ewatch.com] on Sep. 8, 2004, archived May 22, 1998, 50 pages.

Farber, Dave, "IP: eWatch and Cybersleuth," retrieved from [URL: http://www.interesting-people.org/archives/interesting-people/200006/msg00090.html] Jun. 29, 2000, 4 pages.

Filler, "MR Neurography and Diffusion Tensor Imaging: Origins, History & Clinical Impact of the first 50,000 Cases With an Assortment of Efficacy and Utility in a Prospective 5,000 Patent Study Group," Institute for Nerve Medicine, Nov. 7, 2008, 56 pages.

Flinker, A. et al, "Sub-centimeter language organization in the human temporal lobe," Brain and Language, Elsevier Inc., (2010), doi.org/10.1016/j.bandl.2010.09.009, 7 pages.

Fogelson, et al., "Prefrontal cortex is critical for contextual processing: evidence from brain lesions," Brain: A Journal of Neurology, vol. 132, pp. 3002-3010, doi:10.1093/brain/awp230, Aug. 27, 2009, 9 pages.

Freund et al., "Selective Sampling Using the Query by Committee Algorithm," Machine Learning 28 Kluwer Academic Publishers, The Netherlands, 1997, 36 pages.

(56) References Cited

OTHER PUBLICATIONS

Friedman, et al., "Event-Related Potential (ERP) Studies of Memory Encoding and Retrieval: A Selective Review," Microscopy Research and Technique 51:6-26, Wiley-Less, Inc., 2000, 23 pages.
Fries, "A mechanism for cognitive dynamics: neuronal coherence," Trends in Cognitive Sciences, vol. 9, No. 10, pp. 474-480, Elsevier B.V. www.sciencedirect.com, Oct. 2005, 7 pages.
Fuster, "Cortex and Memory: Emergence of a New Paradigm," Journal of Cognitive Neuroscience, vol. 21, No. 11, pp. 2047-2072, Massachusetts Institute of Technology, Nov. 2009, 26 pages.
Gaillard, "Problems and Paradigms in ERP Research," Biological Psychology, Elsevier Science Publisher B.V., 1988, 10 pages.
Gargiulo et al., "A Mobile EEG System With Dry Electrodes," (Nov. 2008), 4 pages.
Gazzaley et al., "Top-down Enhancement and Suppression of Magnitude and Speed of Neural Activity," Journal of Cognitive Neuroscience, vol. No. 3, pp. 507-517, Massachusetts Institute of Technology, 2005, 11 pages.
Gevins et al., "High resolution EEG mapping of cortical activation related to a working memory," Cereb Cprtex. 7, 1997, 12 pages.
Glance et al., "Analyzing online disussion for marketing intelligence," Proceedings WWW-2005 2nd Annual Workshop on the Weblogging Ecosystem, Chiba, Japan, 2005, 2 pages.
Glance et al., "Deriving marketing intelligence from online discussion," 11th ACM SIGKDD International Conference on Knowledge Discovery and Data Mining, Chicago, IL, Aug. 21-24, 2005, 10 pages.
Grefensette et al., "Validating the Coverage of Lexical Resources for Affect Analysis and Automatically Classifying New Words along Semantic Axes," Chapter X, Mar. 3, 2004, 16 pages.
Griss et al., "Characterization of micromachined spiked biopotential electrodes", Biomedical Engineering, IEEE Transactions Jun. 2002, 8 pages.
Haq, "This Is Your Brain on Advertising," BusinessWeek, Market Research, Oct. 8, 2007, 4 pages.
Harabagiu, Sanda M., "An Intelligent System for Question Answering," University of Southern California; Modlovan, Dan, Southern Methodist University, 1996, 5 pages.
Harabagiu, Sanda M., "Experiments with Open-Domain Textual Question Answering," Department of Computer Science and Engineering at Southern Methodist Universtity, 2000, 7 pages.
Harabagiu, Sanda M., "Mining Textual Answers with Knowledge-Based Indicators," Department of Computer Science and Engineering at Southern Methodist University, 2000, 5 pages.
Harland, C.J. et al., "Remote detection of human electroencephalograms using ultrahigh input impedance electrical potential sensors," Applied Physics Letters., vol. 81, No. 17, Oct. 21, 2002, 3 pages.
Harmony et al., "Specific EEG frequencies signal general common congnative processes as well as specific tasks processes in man," International Journal of Psycophysiology, 53, 2004, 10 pages.
Hartikainen et al., Manuscript Draft of "Emotionally arousing stimuli compete with attention to left hemispace," NeuroReport, Sep. 8, 2007, 26 pages.
Hazlett, et al., "Emotional Response to Television Commercials: Facial EMG vs. Self-Report," Journal of Advertising Research, Apr. 1999, 17 pages.
Heo et al., "Wait! Why is it Not Moving? Attractive and Distractive Ocular Responses to Web Ads," Paper presented to AEJMC, (Aug. 2001) Washington, DC, available at http://www.psu.edu/dept/medialab/researchpage/newabstracts/wait.html, 3 pages.
Herrmann, et at, "Mechanisms of human attention: event-related potentials and oscillations," Neuroscience and Biobehavioral Reviews, pp. 465-476, Elsevier Science Ltd., www.elsveriev.com/locate/neubiorev, 2001, 12 pages.
Hopf, et al., "Neural Sources of Focused Attention in Visual Search," Cerebral Cortex, 10:1233-1241, Oxford University Press, Dec. 2000, 9 pages.
Housley et al., "Internet X.509 Public Key Infrastructure Certificate and CRL Profile," Network Working Group Request for Comments: 2459, Jan. 1999, 121 pages.
Hughes, et al., "Conventional and Quantatative Electroencephalography in Psychiatry," Journal of Neuropsychiatry and Clinical Neurosciences, vol. 11(2), 1999, 19 pages.
Joachims, Thorsten, "Text Categorization with Support Vector Machines: Learning with Many Relevant Features," in Machine Learning: ECML-98, Tenth European Conference on Machine Learning, 1998, 7 pages.
Jung et al., "Analysis and Visualization of Single-Trial Event-Related Potentials," Human Brain Mapping vol. 14, 166-185 2001, 20 pages.
Kahn et al., "Categorizing Web Documents using Competitive Learning: An ingrediant of a Personal Adaptive Agent," IEEE 1997, 4 pages.
Katz, Boris, "From Sentence Processing to Information Access on the World Wide Web," MIT Artificial Intelligence Laboratory, Feb. 27, 1997, 20 pages.
Kay et al., "Identifying natural images from human brain activity," Nature, vol. 452, pp. 352-356, Nature Publishing Group, Mar. 20, 2008, 5 pages.
Keren, et al., "Saccadic spike potentials in gamma-band EEG: Characterization, detection and suppression," NeuroImage, http://dx.doi:10.1016/j.neuroimage.2009.10.057, Oct. 2009, 16 pages.
Kishiyama, et al., "Novelty Enhancements in Memory Are Dependent on Lateral Prefrontal Cortex," The Journal of Neuroscience, pp. 8114-8118, Society for Neuroscience Jun. 24, 2009, 5 pages.
Kishiyama, et al., "Socioeconomic Disparities Affect Prefrontal Function in Children," Journal of Cognitive Neuroscience pp. 1106-1115, Massachusetts Institute of Technology, 2008, 10 pages.
Kleppner, "Advertising Procedure," 6th edition, 1977, Prentice-Hall, Inc., Englewood Cliffs, NJ, p. 492, 3 pages.
Klimesch, "EEG alpha and theta oscillations reflect cognitive and memory performance a review and analysis," Brain Research Reviews, vol. 29, 169-195, 1999, 27 pages.
Klimesch, et al. "Episodic and semantic memory: an analysis in the EEG theta and alpha band," Electroencephalography Clinical Neurophysiology, 1994, 14 pages.
Kotler, "Marketing Management," PrenticeHall International Inc., Upper Saddle River, NJ, 1997, 10 pages.
Knight, "Contribution of human hippocampal region to novelty detection," Nature, vol. 383, www.nature.com, Sep. 19, 1996, 4 pages.
Knight, "Consciousness Unchained: Ethical Issues and the Vegetative and minimally Conscious State," The American Journal of Bioethics, 8:9, 1-2, http://dx.doi.org/10.1080/15265160802414524, Sep. 1, 2008), 3 pages.
Knight, et al., "Prefrontal cortex regulates inhibition and excitation in distributed neural networks," Acta Psychologica vol. 101, pp. 159-178, Elsevier 1999, 20 pages.
Knight, "Decreased Response to Novel Stimuli after Prefrontal Lesions in Man," Electroencephalography and Clinical Neurophysiology, vol. 59, pp. 9-20, Elsevier Scientific Publishers Ireland, Ltd., 1984, 12 pages.
Krakow et al., "Methodology: EEG-correlated fMRI," Functional Imaging in the Epilepsies, Lippincott Williams & Wilkins, 2000, 17 pages.
Krugman, "Brain Wave Measures of Media Involvement," Journal of Advertising Research vol. 11, Feb. 3-9, 1971, 7 pages.
Lachaux et al., "Measuring Phase Synchrony in Brain Signals," Human Brain Mapping 8, 1999, 194-208, 15 pages.
Lee et al., "What is 'neuromarketing'? A discussion and agenda for future research," International Journal of Psychophysiology, vol. 63, pp. 199-204, Elsevier 2006, 6 pages.
Lekakos, "Personalized Advertising Services Through Hybrid Recommendation Methods: The Case of Digital Interactive Television," Department of Informatics, Cyprus University, 2004, 11 pages.
Lenz et al., "Question answering with Textual CBR," Department of Computer Science, Humboldt University Berlin, D-10099 Berlin, 1998, 12 pages.
Lewis et al., "Market Researchers make Increasing use of Brain Imaging," ACNR, vol. 5, No. 3, pp. 36-37, Jul./Aug. 2005, 2 pages.

(56) References Cited

OTHER PUBLICATIONS

Littlestone, Nick, "Learning Quickly When Irrelevant Attributes Abound: A New Linear-threshold Algorithm," in Machine Learning, vol. 2, Kluwer Academic Publishers, Boston, MA, 1988, 34 pages.
Luck, et al., "The speed of visual attention in schizophrenia: Electrophysiological and behavioral evidence," Schizophrenia Research, pp. 174-195, Elsevier B.V. www.sciencedirect.com, 2006, 22 pages.
Lui et al., "Marketing Strategies in Virtual Worlds," The Data Base for Advances in Information Systems, vol. 38, No. 4, pp. 77-80, Nov. 2007, 4 pages.
Makeig, et al., "Mining event-related brain dynamics," TRENDS in Cognitive Sciences, vol. 8, No. 5, May 2004, www.sciencedirect.com, 7 pages.
Makeig, et al., "Dynamic Brain Sources of Visual Evoked Responses," Science, vol. 295, www.sciencemag.org, Jan. 25, 2002, 5 pages.
Marlow, "Audience, structure and authority in the weblog community," International Communication Association Conference, MIT Media Laboratory, New Orleans, LA 2004, 9 pages.
The Mathworks, Inc., "MATLAB Data Analysis: Version 7," p. 4-19 2005, 3 pages.
McCallum et al., "Text Classification by Bootstrapping with the Keywords, EM and Shrinkage," Just Research and Carnegie Mellon University, Pittsburgh, PA, circa 1999, 7 pages.
McLachlan et al., "The EM Algorithm and Extensions," John Wiley & Sons, Inc., New York, NY, 1997, 302 pages.
Meriam-Webster Online Dictionary definition for "tangible," available at http://www.meriam-webster.com/dictionary/tangible, 1 page.
Meriam Webster Online Dictionary, Definition of Virtual Reality, available at http://www.meriam-webster.com/dictionary/virtual%20reality, 2 page.
Miltner, et al., "Coherence of gamma-band EEG activity as a basis for associative learning," Nature, vol. 397, www.nature.com, Feb. 4, 1999, 3 pages.
Mizuhara et al., A long range cortical network emerging with theta oscillation in mental task, Neuroreport 15 (8), 2004, 11 pages.
Moldovan et al., "LASSO: A Tool for Surfing the Answer Net," Department of Computer Science and Engineering at Southern Methodist University, 1999, 9 pages.
Mosby's Dictionary of Medicine, Nursing, & Health Professions, 2009, Mosby, Inc., Definition of Alpha Wave, 1 page.
Mosby's Dictionary of Medicine, Nursing, & Health Professions, 2009, Mosby, Inc., Definition of Beta Wave, 1 page.
Nakashima et al., "Information Filtering for the Newspaper," IEEE 1997, 4 pages.
Nanno et al., "Automatic collection and monitoring of Japanese Weblogs," Proceedings WWW-2004 Workshop on the weblogging Ecosystem, 2004, New York, NY, 7 pages.
Netcurrent, NetCurrent's web site, http://web.archive.org/web/20000622024845/www.netcurrents.com, retrieved on Jan. 17, 2005, archived on Jun. 22, 2000 and Sep. 18, 2000, 17 pages.
Neurofocus—Neuroscientific Analysis for Audience Engagement, accessed on Jan. 8, 2010 at http://web.archive.org/web/20080621114525/www.neurofocus.com /BrandImage.htm, 2008, 2 pages.
Newell et al., "Categorical perception of familiar objects," Cognition, vol. 85, Issue 2, pp. 113-143 Sep. 2002, 31 pages.
Nielsen, "Neuroinformatics in Functional Neuroimaging," Informatics and Mathematical Modeling, Technical University of Denmark, Aug. 30, 2002, 241 pages.
Oberman et al., "EEG evidence for minor neuron activity during the observation of human and robot actionsAug. 29, 2012 Toward an analysis of the human qualities of interactive robots," Neurocomputing 70, 2007 2194-2203, 10 pages.
Osborne, "Embedded Watermarking for image Verification in Telemedicine," Thesis submitted for the degree of Doctor of Philosophy, Engineering and Electronic Engineering, University of Adelaide, 2005, 219 pages.
Padgett et al., "Categorical Perception in Facial Emotion Classification," In Proceedings of the 18th Annual Conference of the Cognitive Science Society, pp. 249-253, 1996, 5 pages.
Page et al., "Cognitive Neuroscience, Marketing and Research," Congress 2006—Foresight—The Predictive Power of Research Conference Papers, ESOMAR Publications, Sep. 17, 2006, 25 pages.
Palley, et al., "Validating neural correlates of familiarity," TRENDS in Cognitive Sciences, vol. 11, No. 6, www.sciencedirect.com, May 2, 2007, 8 pages.
Palva et al., "Phase Synchrony Among Neuronal Oscillations in the Human Cortex," Journal of Neuroscience 25 2005, 3962-3972, 11 pages.
Pang et al., "Thumbs up? Sentiment Classification using Machine Learning Techniques," in Proceedings of EMNLP 2002, 8 pages.
Picton, et al., "Guidelines for using human event-related potentials to study cognition: Recording standards and publication criteria," Psychophysiology, pp. 127-152, Society for Psychophysiological Research, 2000, 26 pages.
Reguly, "Caveat Emptor Rules on the Internet," The Globe and Mail (Canada): Report on Business Column, Apr. 10, 1999, 2 pages.
Reinartz, "Customer Lifetime Value Analysis: An Integrated Empirical Framework for Measurement and Explanation," dissertation, University of Houston, Faculty of College of Business Administration, Apr. 1999, 68 pages.
Rizzolatti et al., "The Mirror-Neuron System," Annu. Rev. Neurosci., vol. 27, pp. 169-192, Mar. 5, 2004, 30 pages.
Rothschild et al., "Predicting Memory for Components of TV Commercials from EEG," Journal of Consumer Research (Mar. 1990), p. 472-478, 8 pages.
Ruchkin et al., "Modality-specific processing streams in verbal working memory: evidence from spatio-temporal patterns of brain activity," Cognitive Brain Research, vol. 6, pp. 95-113, Elsevier, 1997, 19 pages.
Rugg, et al., "Event-related potentials and recognition memory," TRENDS in Cognitive Sciences, vol. 11, No. 6, www.sciencedirect.com, May 3, 2007, 7 pages.
Rugg, et al., "The ERP and cognitive psychology: conceptual issues," Sep. 1996, 7 pages.
"User monitoring," Sapien Systems, available at http://web.archive.org/web/20030818043339/http:/www.sapiensystems.com/eyetracking.html, Aug. 18, 2003, 1 page.
Sammler, "Music and emotion: Electrophysiological correlates of the processing of pleasant and unpleasant music," Psychophysiology, vol. 44, Blackwell Publishing Inc., 2007, 12 pages.
Schmidt et al., "Frontal brain electrical activity (EEG) distinguishes valence and intensity of musical emotions," Cognition and Emotion, vol. 15 (4), Psychology Press Ltd, 2001, 14 pages.
Selden, G., "Machines that Read Minds," Science Digest, Oct. 1981, 9 pages.
Shandlen, Michael N. et al., "A Computational Analysis of the Relationship between Neuronal and Behavioral Responses to Visual Motion", The Journal of Neuroscience, (Feb. 15, 1996) 1486-1510, 25 pages.
Simon-Thomas, et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology 2005, 12 pages.
Soderland et al., "Customer Satisfaction and Links to Customer Profitability: An Empirical Examination of the Association Between Attitudes and Behavior," SSE/EFI Working Paper Series in Business Administration, Jan. 1999, 22 pages.
Spencer, "Averaging, Detection, and Classification of Single-Trial ERPs," in Event-Related Potentials: A Methods Handbook, pp. 209-227, (Todd C. Handy, ed., 2005), 10 pages.
Arousal in Sport, in Encyclopedia of Applied Psychology, vol. 1, p. 159, retrieved from Google Books, (Spielberger, ed., Elsevier Academic Press, 2004), 1 page.
Srinivasan, "High-Resolution EEG: Theory and Practice," in Event-Related Potentials: A Methods Handbook, pp. 167-188, (Todd C. Handy, ed., 2005), 12 pages.

(56) References Cited

OTHER PUBLICATIONS

Sullivan et al., "A brain-machine interface using dry-contact, low-noise EEG sensors," In Proceedings of the 2008 IEEE International Symposium on Circuits and Systems, May 18, 2008, 4 pages.

Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, Mar. 2007, 5 pages.

Swick, et al., "Contributions of Prefrontal Cortex to Recognition Memory: Electrophysiological and Behavioral Evidence," Neuropsychology, vol. 13, No. 2, pp. 155-170, American Psychological Association, Inc. 1999, 16 pages.

Taheri, et al., "A dry electrode for EEG recording," Electroencephalography and clinical Neurophysiology, pp. 376-383, Elsevier Science Ireland Ltd., 1994, 8 pages.

Talsma, et al., "Methods for the Estimation and Removal of Artifacts and Overlap in ERP Waveforms," in Event-Related Potentials: A Methods Handbook, pp. 115-148, (Todd C. Handy, ed., 2005), 22 pages.

Tapert, Susan F., et al., "Neural Response to Alcohol Stimuli in Adolescents With Alcohol Use Disorder", Arch Gen Psychiatry (Jul. 2003), 727-735, 9 pages.

"Technology Platform: SmartShirt + Eye-Tracking," Innerscope Research, Mar. 2007, 1 page.

Thomas, "International Marketing," International Textbook Company, Scranton, PA 1971, 3 pages.

Trigaux, Robert, "Cyberwar Erupts Over Free Speech Across Florida, Nation," Knight-Ridder Tribune Business News, May 29, 2000, 4 pages.

Tull et al., "Marketing Research Measurement and Method," MacMillan Publishing Company, New York, NY, 1984, 9 pages.

Vogel, et al., "Electrophysiological Evidence for a Postperceptual Locus of Suppression During the Attentional Blink," Journal of Experimental Psychology: Human Perception and Performance, vol. 24, No. 6, pp. 1656-1674, 1998, 19 pages.

Voorhees, Ellen M., "The TREC-8 Question Answering Track Report," National Institute of Standards and Technology, 1999, 6 pages.

Voytek, et al., "Prefrontal cortex and basal ganglia contributions to visual working memory," PNAS Early Edition, www.pnas.org/cgi/doi/10.1073/pnas.1007277107, 2010, 6 pages.

Voytek, et al., "Hemicraniectomy: A New Model for Human Electrophysiology with High Spatio-temporal Resolution," Journal of Cognitive Neuroscience, vol. 22, No. 11, pp. 2491-2502, Massachusetts Institute of Technology, Nov. 2009, 12 pages.

Wang, "Neurophysiological and Computational Principles of Cortical Rhythms in Cognition," Physiol Rev 90: pp. 1195-1268, American Physiological Society, www.prv.org, (2010), 75 pages.

Wiebe et al., "Identifying Collocations for Recognizing Opinions," in proceedings of ACL/EACL '01 Workshop on Collocation, Toulouse, France, Apr. 9, 2001, 9 pages.

Willis et al., "Discover Your Child's Learning Style: Children Learn in Unique Ways—Here's the Key to Every Child's Learning Success," Prime Publishing, 1999, 22 pages.

Anonymous, "Functional magnetic resonance imaging," retrieved online from Wikipedia, the Free Encyclopedia on Aug. 23, 2011, at http://en.wikipedia.org/w/index.php?title=Functional_magnetic_resonance_imaging&oldid=319601772, Oct. 13, 2009, 8 pages.

William, "Brain Signals to Control Movement of Computer Cursor," Blog article: Brain Signals to Control Movement of Computer Cursor, Artificial Intelligence, retrieved from the Internet on Aug. 17, 2011, http://whatisartificialintelligence.com/899/brain-signals-to-control-movement-of-computer-cursod, Feb. 17, 2010, 3 pages.

Wise, A., "The High Performance Mind, Mastering Brainwaves for Insight, Healing and Creativity," G.P. Putnam's Son, New York, 1996, pp. 13-15; 20-22; 143-156, 11 pages.

Wise, A., "The High Performance Mind, Mastering Brainwaves for Insight, Healing and Creativity," G.P. Putnam's Son, New York, 1996, pp. 156-158; 165-170; 186-187, 15 pages.

Woldorf, "Distortion of ERP averages due to overlap from temporally adjacent ERPs: Analysis and correction," Psychophysiology, Society for Psychophysiological Research, Cambridge University Press, 1993, 22 pages.

Woodman, et al., "Serial Deployment of Attention During Visual Search," Journal of Experimental Psychology: Human Perception and Performance, vol. 29, No. 1, pp. 121-138, American Physiological Association(2003, 18 pages.

Word of Mouth Research Case Study, "The Trans Fat Issue, Analysis of online consumer conversation to understand how the Oreo lawsuit impacted word-of-mouth on trans fats," Aug. 16, 2004, 35 pages.

Yamaguchi, et al., "Rapid-Prefrontal-Hippocampal Habituation to Novel Events," The Journal of Neuroscience, pp. 5356-5363, Society for Neuroscience, (Apr. 29, 2004), 8 pages.

Yang, "An Evaluation of Statistical Approaches to Text Categorization," Information Retrieval 1 (1/2) Apr. 10, 1999, 12 pages.

Yap et al., "TIMER: Tensor Image Morphing for Elastic Registration," NeuroImage, vol. 47, May 3, 2009, 15 pages.

Yuval-Greenberg, et al., "Transient Induced Gamma-Bands Response in EEG as a Manifestation of Miniature Saccades," Neuron, vol. 58, pp. 429-441, Elsevier Inc. May 8, 2008, 13 pages.

Zagat, www.zagat.com, archived on Apr. 29, 1999, 33 pages.

Zagat, www.zagat.com, archived version of p. 34, Feb. 1999, 1 page.

Zhang, P., "Will You Use Animation on Your Web Pages?" Doing Business on the Internet: Opportunities and Pitfalls, C. Romm and F. Sudweeks (eds.), Spring-Verlag, 1999, 17 pages.

Ziegenfuss, "Neuromarketing: Advertising Ethical & Medical Technology," The Brownstone Journal, vol. XII, Boston University, pp. 69-73, May 2005, 9 pages.

Zyga, "A Baseball Cap That Can Read Your Mind," PhysOrg.com, located at www.physorg.com/news130152277.html, May 16, 2008, 11 pages.

Merriam-Webster Online Dictionary, Definition for "Resonance," available at http://www.merriam-webster.com/dictionary/resonance, 4 pages.

Enghoff, Sigurd, Thesis: "Moving ICA and Time-Frequency Analysis in Event-Related EEG Studies of Selective Attention," Technical University of Denmark, Dec. 1999, 54 pages.

Extended European Search Report, issued by the European Patent Office in connection with European Patent Application No. 13004052.0, dated Dec. 19, 2013, 9 pages.

Junghoffer M. et al.,"Statistical Control of Artifacts in Dense Array EEG/MEG Studies," Psychophysiology, vol. 37, No. 4, Society for Psychophysiological Research, Jul. 1, 2000, 10 pages.

Nolan H . et al., "FASTER: Fully Automated Statistical Thresholding for EEG Artifact Rejection," Journal of Neuroscience Methods, vol. 192, No. 1, Elsevier Science Publisher, Sep. 30, 2010, 12 pages.

Notification of Reason(s) for Rejection, English version issued by the Japanese Intellectual Property Office in connection with Japanese Patent Application No. P2013-169723, dated Jul. 1, 2014, 4 pages.

International Search Report and Written Opinion, issued by the International Searching Authority in connection with corresponding International patent application No. PCT/US2014/020255, dated May 23, 2014, 15 pages.

Notification of the First Office Action, issued by the State Intellectual Property Office of the P.R. China, in connection with Chinese Patent Application No. 201310471815.3, dated Feb. 9, 2015, 22 pages.

Office Action, issued by the United States Patent and Trademark Office in connection with U.S. Appl. No. 13/728,900, dated Jun. 25, 2014, 5 pages.

Office Action issued by the United States Patent and Trademark Office in connection with U.S. Appl. No. 13/728,900 dated Aug. 8, 2014, 4 pages.

Office Action issued by the United States Patent and Trademark Office in connection with U.S. Appl. No. 13/728,900 dated Oct. 9, 2014, 5 pages.

Notice of Allowance and Fee(s) Due, issued by the United States Patent and Trademark Office in connection with U.S. Appl. No. 13/728,900 dated Feb. 5, 2015, 5 pages.

(56) References Cited

OTHER PUBLICATIONS

Restriction and/or Election Requirement issued by the United States Patent and Trademark Office in connection with U.S. Appl. No. 13/728,913 dated Jun. 25, 2014, 7 pages.
Office Action issued by the United States Patent and Trademark Office in connection with U.S. Appl. No. 13/728,913 dated Aug. 7, 2014, 5 pages.
Notice of Allowance and Fee(s) Due, issued by the United States Patent and Trademark Office in connection with U.S. Appl. No. 13/728,913, dated Nov. 19, 2014, 7 pages.
Corrected Notice of Allowability, issued by the United States Patent and Trademark Office in connection with U.S. Appl. No. 13/728,913, dated Feb. 25, 2015, 2015, 2 pages.
Office Action issued by the United States Patent and Trademark Office in connection with U.S. Appl. No. 13/730,212 dated Apr. 23, 2015, 15 pages.
Office Action issued by the United States Patent and Trademark Office in connection with U.S. Appl. No. 14/610,473 dated May 4, 2015, 7 pages.
Notice of Allowance and Fee(s) Due, issued by the United States Patent and Trademark Office in connection with U.S. Appl. No. 14/610,473, dated Aug. 14, 2015, 7 pages.
Notification of the Second Office Action, issued by the State Intellectual Property Office of the P.R. China, in connection with Chinese Patent Application No. 201310471815.3, dated Aug. 31, 2015, 11 pages.
United States Patent and Trademark Office, "Non-Final Office Action," issued in connection with U.S. Appl. No. 15/044,488, dated Jul. 31, 2017, 63 pages.

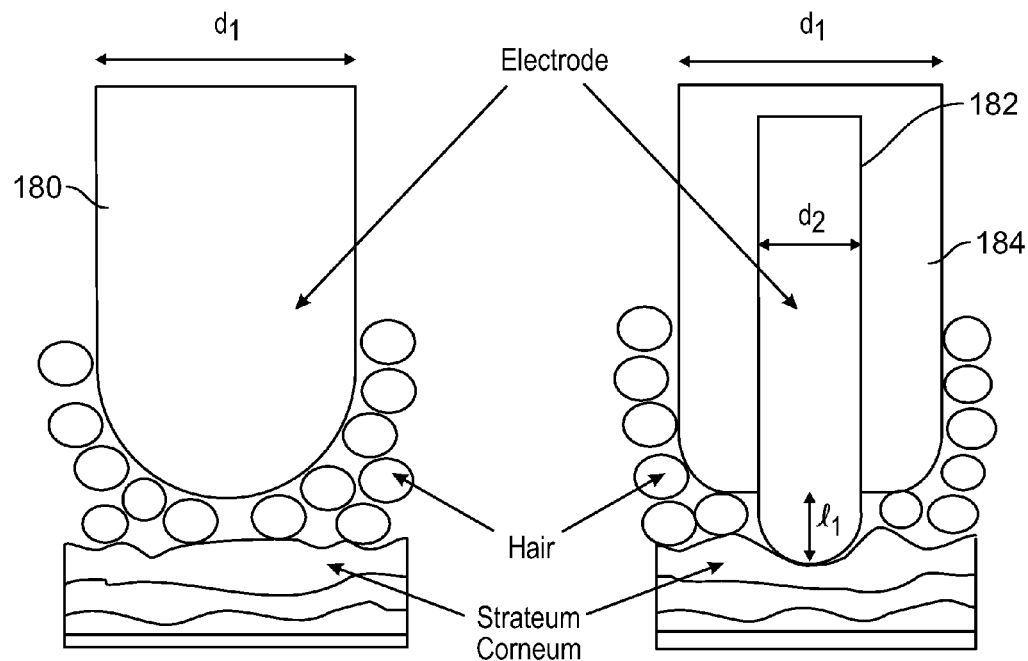
FIG. 13A
FIG. 13B
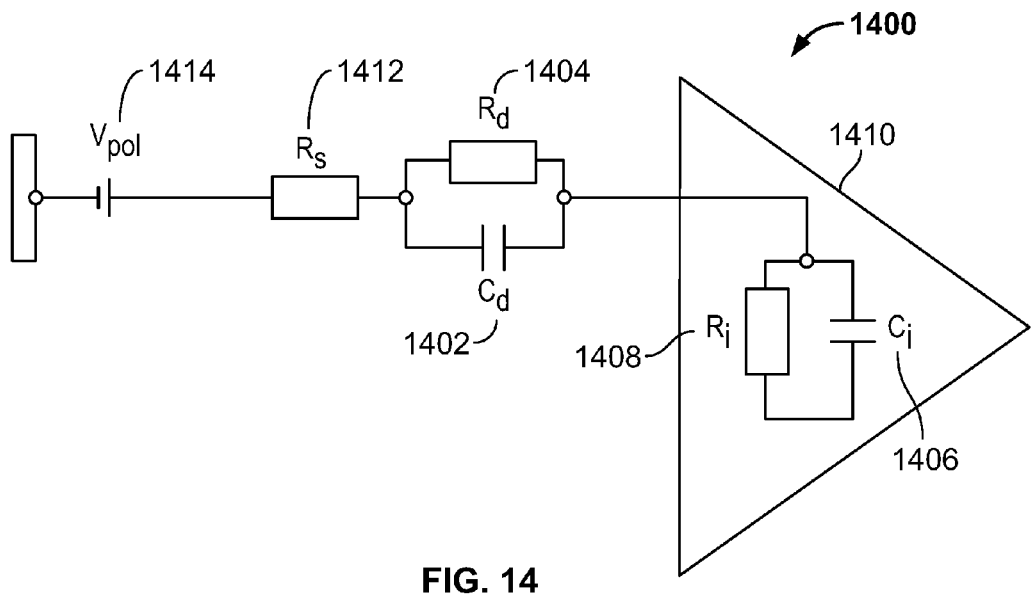
FIG. 14

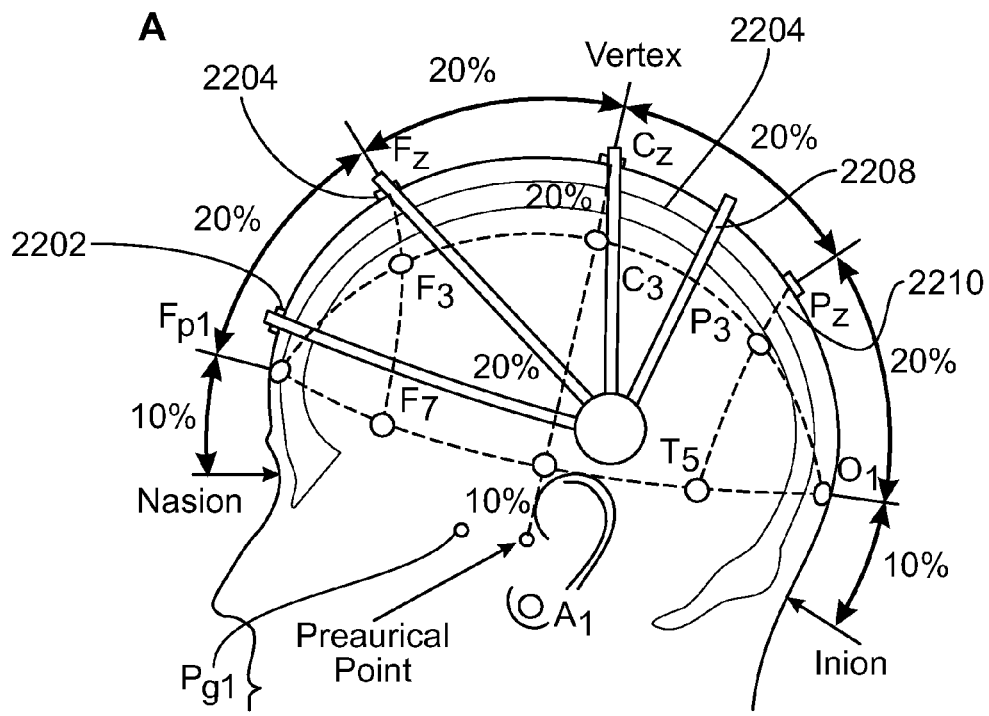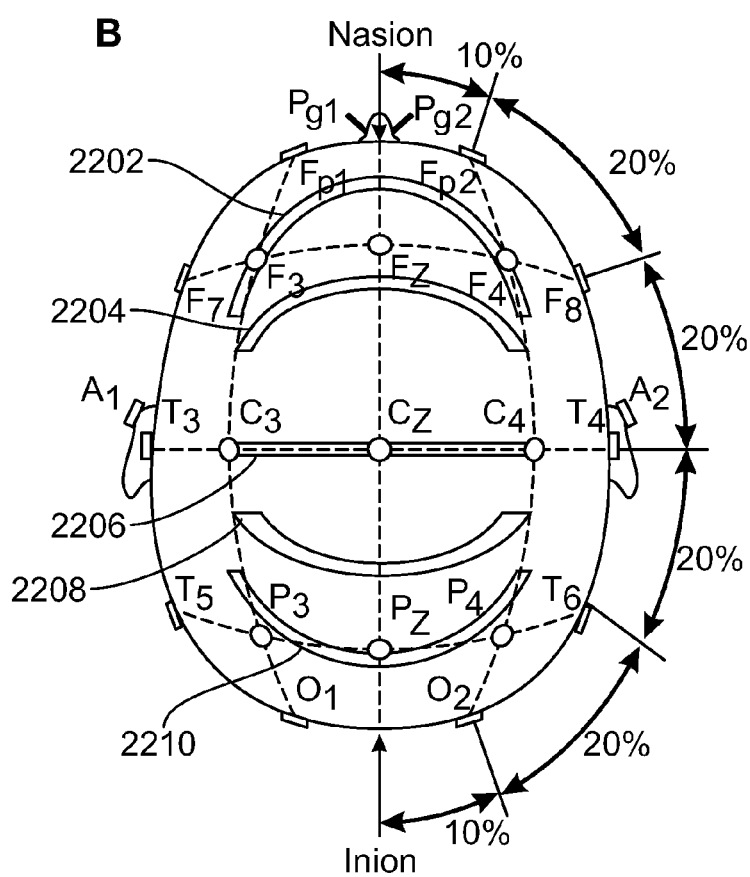
FIG. 22J

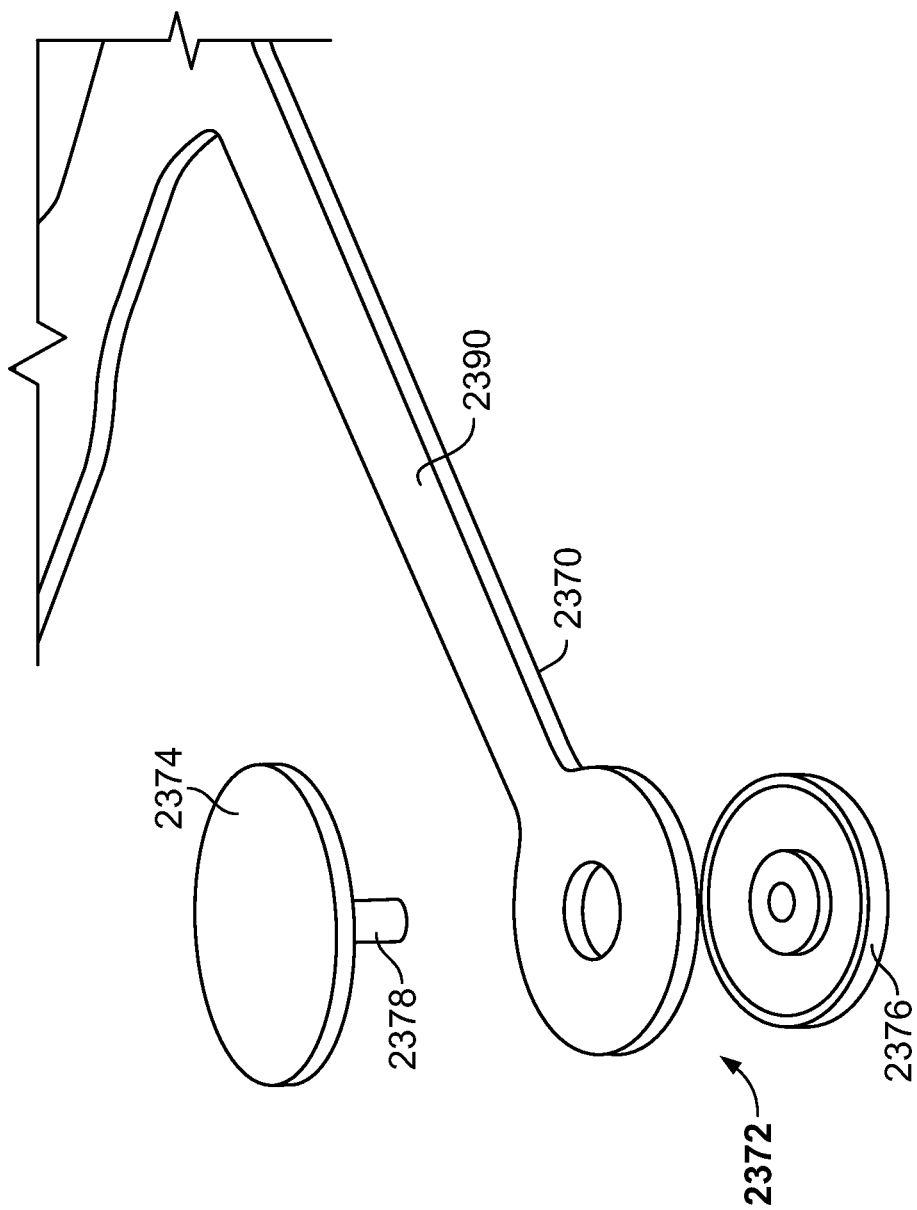

SYSTEMS AND METHODS TO GATHER AND ANALYZE ELECTROENCEPHALOGRAPHIC DATA

CROSS-REFERENCE TO RELATED APPLICATIONS

This patent arises from a continuation of U.S. application Ser. No. 13/728,900 (now U.S. Pat. No. 9,060,671), titled "SYSTEMS AND METHODS TO GATHER AND ANALYZE ELECTROENCEPHALOGRPHIC DATA," filed Dec. 27, 2012, which claims priority to U.S. Provisional Application No. 61/684,640 titled "SYSTEMS AND METHODS TO GATHER AND ANALYZE ELECTROENCEPHALOGRPHIC DATA," filed Aug. 17, 2012. U.S. application Ser. No. 13/728,900 and U.S. Provisional Application No. 61/684,640 are hereby incorporated by this reference in their entireties.

FIELD OF THE DISCLOSURE

The present disclosure relates generally to neurological and physiological monitoring, and, more particularly, to systems and methods to gather and analyze electroencephalographic data.

BACKGROUND

Electroencephalography (EEG) involves measuring and recording electrical activity resulting from thousands of simultaneous neural processes associated with different portions of the brain. EEG data is typically measured using a plurality of electrodes placed on the scalp of a user to measure voltage fluctuations resulting from this electrical activity within the neurons of the brain. Subcranial EEG can measure electrical activity with high accuracy. Although bone and dermal layers of a human head tend to weaken transmission of a wide range of frequencies, surface EEG also provides useful electrophysiological information.

BRIEF DESCRIPTION OF THE DRAWINGS

FIG. 13A is a cross-sectional view of an example electrode in contact with a scalp of a user.

FIG. 13B is a cross-section view of an alternative example electrode in contact with a scalp of a user.

FIG. 14 is a circuit diagram for an example electrode.

FIGS. 22A-22J are perspectives views of a user's head and example areas for electrode contact.

FIGS. 32A-32D are exploded views of an example electrode connector used in the example headset of FIG. 23.

DETAILED DESCRIPTION

Figure 1:
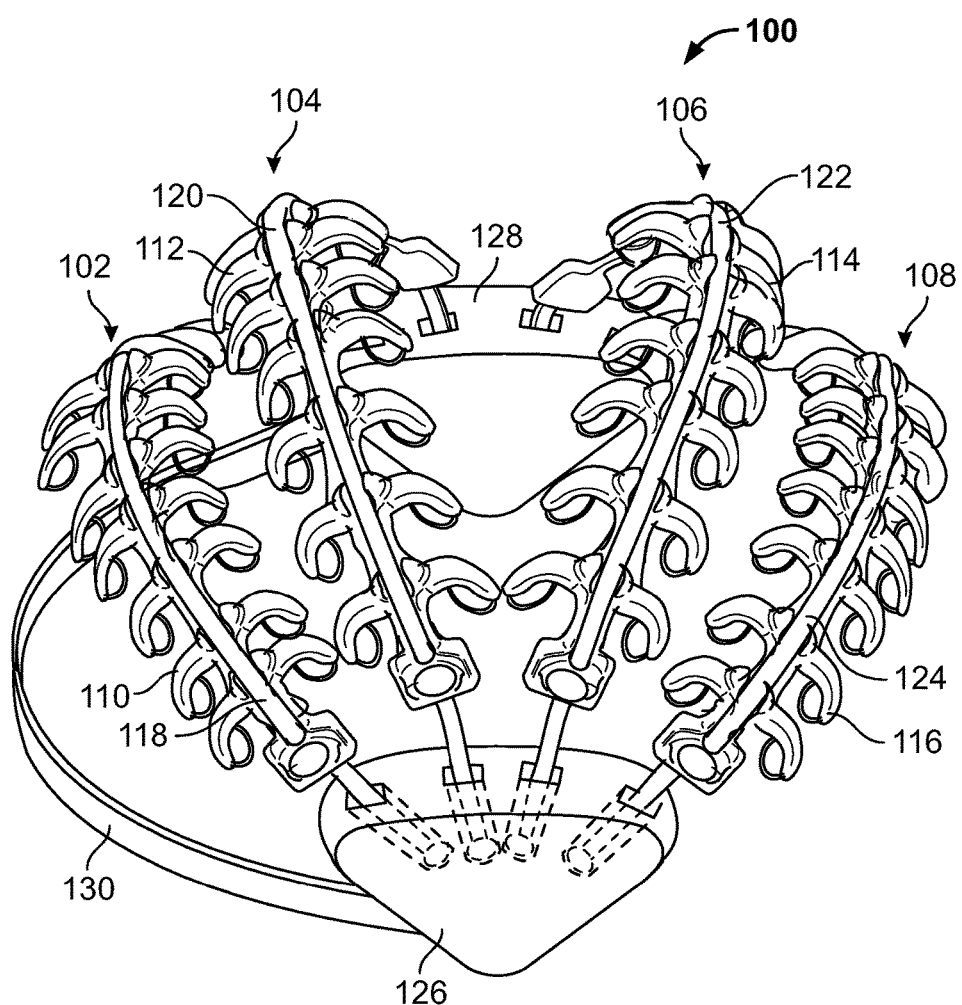
FIG. 1 illustrates a perspective view of an example headset having a plurality of adjustable bands in accordance with the teachings of this disclosure.
Figure 2:
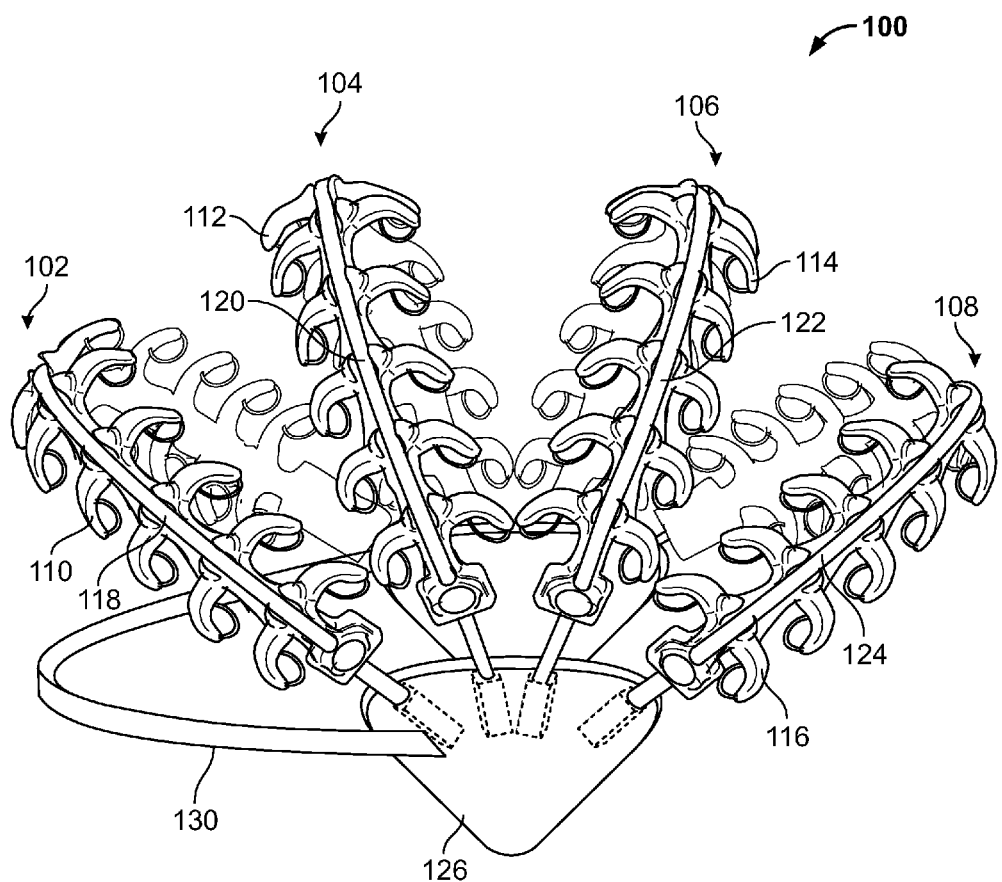
FIG. 2 is a right side view of the headset of FIG. 1.
Figure 3:
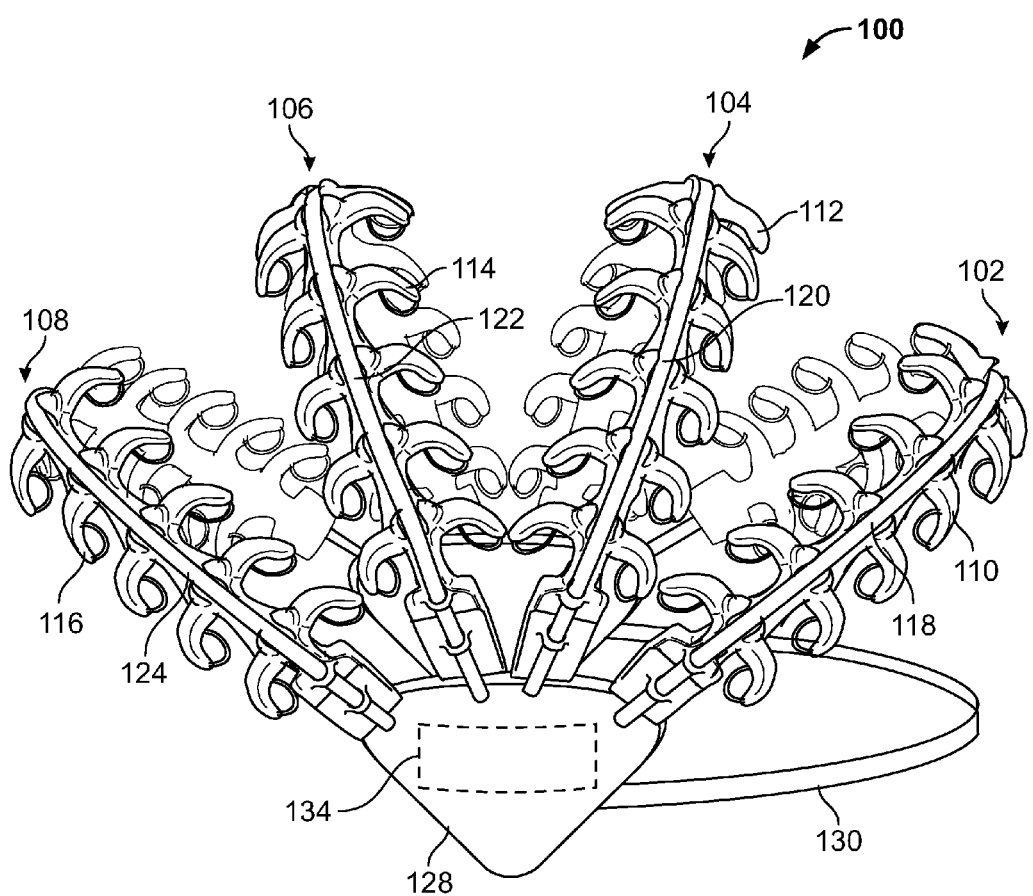
FIG. 3 is a left side view of the headset of FIG. 1.

Certain examples are shown in the above-identified figures and disclosed in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification.

Biological cells and tissues have electrical properties that can be read, which provide information regarding the functioning of the cell or tissue. Various types of electrophysiological techniques have been developed to measure electrical signals from a body. For example, electrocardiography (ECG or EKG) measures electrical activity in a heart. Electroencephalography (EEG) measures electrical activity in a brain. Electrocorticography (ECoG) measures electrical activity using electrodes placed directly on an exposed surface of a brain to record electrical activity in a cerebral cortex. Electromyography (EMG) measures electrical activity in a muscle. Electrooculography (EOG) measures the resting potential of a retina, and electroretinography measures electrical responses of retinal cells. These and/or other electrophysiological signals are important in the treatment, diagnosis and monitoring of many health conditions.

EEG data is indicative of electrical activity of neurons including neural depolarization in the brain due to stimuli of one or more of the five senses (evoked activity) as well as from thought processes (spontaneous activity) generates electrical activity in the brain. Summations of these electrical activities, (e.g., brainwaves), propagate to the surface and are detectable with electroencephalograms. Because the current flow in the human body is due to ion flow, a biopotential electrode is used, which forms an electrical double layer with the human skin to sense the ion distribution.

EEG data can be classified in various bands. Brainwave frequencies include delta, theta, alpha, beta and gamma frequency ranges. Delta waves are classified as those less than about 4 Hertz (Hz) and are prominent during sleep. Theta waves have frequencies between about 3.5 Hz to about 7.5 Hz and are associated with memories, attention, emotions, and sensations. Theta waves are typically prominent during states of internal focus. Alpha frequencies reside between about 7.5 Hz and about 13 Hz and typically peak around 10 Hz. Alpha waves are prominent during states of relaxation. Beta waves have a frequency range between about 14 Hz and about 30 Hz. Beta waves are prominent during states of motor control, long range synchronization between areas, analytical problem solving, judgment, and decision making. Gamma waves occur between about 30 Hz and about 100 Hz and are involved in binding of different populations of neurons together into a network for the purpose of carrying out a certain cognitive or motor function, as well as in attention and memory. Because the skull and dermal layers attenuate waves in this frequency range, brain waves above about 75 Hz (e.g., high gamma band or kappa band) are less easily measured than waves in lower frequency bands. EEG data may be used to determine an emotional or mental state of a person including, for example, attention, emotional engagement, memory or resonance, etc.

EEG signals may be measured using a plurality of electrodes placed on a scalp of a person (e.g., a user, a viewer, a subject, a panelist, a participant or a patient) to measure voltage fluctuations resulting from electrical activity associated with post synaptic currents occurring in the milliseconds range within neurons of a brain. Though subcranial EEG can measure electrical activity with high accuracy, surface electrodes such as, for example, dry electrodes also provide useful neuro-response information.

Many traditional EEG electrodes suffer from high impedance and/or require messy gels to increase signal quality. In addition, many known EEG headsets utilize a helmet or head-strap type assembly that include a limited number of electrodes. These known headsets are uncomfortable to wear and typically cannot effectively accommodate a variety of differently sized heads.

To enable the surface EEG electrodes to effectively receive signals from the brain, the electrodes are to be placed as close to the scalp as possible. The electrodes may be manually placed upon a subject's head or may be contained in a wearable apparatus such as, for example, a headset. However, a subject's hair may interfere with the contact between an electrode and the scalp by limiting the surface area contact of the electrode. For example the average person tends to have from about 80 to about 200 hair follicles per square centimeter (follicles/cm$^2$). The hair strands and the hair follicles that are interposed between the electrode and the scalp raise impedance several mega-Ohms (MΩ). EEG systems with impedances greater than 100 kilo-Ohms (kΩ) are vulnerable to various sources of noise that obscure the reading of the EEG signal Impedance can be reduced by applying pressure to the electrodes thus decreasing the distance between the electrodes and the tissue of the scalp. However, too much pressure such as, for example, greater than two Newtons per millimeter square (N/mm$^2$) results in discomfort for the subject. In some examples, the pressure slightly compresses the underlying stratum corneum, which is the outermost layer of the epidermis, for example the outermost 10-40 micrometers (μm). Known EEG sensors do not account for the thickness of one or more strands of hair or hair follicles and do not effectively adjust to a specific size of a user head and, thus, known systems cannot apply an effective amount of pressure against the scalp. In some examples disclosed herein, a profile of the electrode including the electrode tip is designed to achieve both comfort and noise reduction. In addition, in examples disclosed herein, a headset into which the electrodes are incorporated is modularly adjustable also to enhance comfort and noise reduction, as disclosed in greater detail below.

Because of the very low signal amplitude of EEG data and high impedances, noise is a significant factor to consider in high quality EEG instruments. Noise types are classifiable by the various sources of the noise such as, for example, skin potential noise, thermal noise, amplifier noise, electrode noise and interference noise.

Skin potential noise relates to stretching of the skin that causes a change of the potential at the electrode. Examples disclosed herein mitigate skin potential noise by utilizing special electrode shape(s) such that the pressure imparted by the electrodes onto the scalp reduces skin potential noise. Because the skin is stretched and pressed by the example electrodes described herein, there is less noise in general and less noise when the subject moves. An optimized pressure imparted by the electrodes onto the scalp decreases skin potential noise while increasing comfort. An example pressure is less than about 2 N/mm$^2$.

Thermal noise is electronic noise generated by thermal agitation of charge carrying electronic components. Thermal noise is proportional to the impedance and bandwidth and may be represented by the equation: $V_{TH}=(4\ kTBR)^{1/2}$, where k is the Boltzman constant, T is temperature in Kelvins (K), B is the bandwidth in Hertz, and R is the electrode impedance in Ohms (Ω). For example, with a target impedance of 1 MΩ at room temperature (T=300K) and 150 Hz bandwidth, the thermal noise will be about 1 micro-volt root-mean-square (μVrms). Averaging over a number independently digitized electrodes, n, improves the signal-to-noise ratio by about $1/(n)^{1/2}$ (e.g., see FIG. 12B). As disclosed in greater detail below, an electrode shape with an effective diameter below 0.2 millimeter (mm) allows up to about 100 independent digitized electrodes in an area having a diameter of about less than 15 mm. In some example EEG systems, there is a spatial resolution at the surface of the scalp of a maximum of about 15 mm. The examples disclosed herein mitigate thermal noise by averaging readings over multiple electrodes such as, for example, averaging with n=100 electrodes by a factor of 10.

Amplifier noise is noise intrinsic to the amplification process. Amplifier noise is typically small such as, for example, around 0.5 μVrms at a bandwidth of about 150 Hz. The examples disclosed herein mitigate amplifier noise by averaging readings over multiple electrodes, thereby cancelling at least a portion of the noise out. Averaging over n number of independently digitized electrodes improves the signal-to-noise ratio by about $1/(n)^{1/2}$ (e.g., see FIG. 12B, thus taking into account both thermal noise and amplifier noise). Also, as described above, with the example electrode shape disclosed below, which has an effective diameter below 0.2 mm, with more than 100 independent digitized electrodes in an area having a diameter of less than about 15 mm, and with a spatial resolution at the surface of the scalp of maximum about 15 mm, the examples disclosed herein also mitigate amplifier noise by averaging readings over multiple electrodes such as, for example, by averaging with n=100 electrodes by a factor of 10.

Interference noise exists due to the presence of external electromagnetic fields (e.g. power lines). Electromagnetic induced noise can penetrate the EEG signal over several pathways. For example, an electric field can induce displacement current into the electrode leads, the electrode-skin interface or individual components of the EEG device (e.g. amplifier, power supplies, etc). Another source of electromagnetic noise is the common mode voltage on the subject's body ($V_c$), which is composed of a static voltage component ($V_s$) and a power-line-induced component ($V_a$). The power-line-induced component ($V_a$) is caused by a displacement current ($I_d$), which flows through stray capacitance ($C_d$). The size of this capacitance is determined by the proximity of the subject is to power sources. The power-line-induced component ($V_a$) can be as large as 20V, for example, if the subject grasps an insulated power cord. Friction creates a charge that is stored in capacitance between the body and ground ($C_b$). For example, a third person who is charged in this way can induce a static voltage into the subject if he/she moves close to the subject. The examples disclosed herein enable the encapsulation of the EEG signal from external electromagnetic fields, which enhances the robustness of the EEG signal against electromagnetic noise sources. In some disclosed examples, a faraday cage is established around the EEG system to decouple the EEG system from environmental noise. Also, a dedicated shielding electrode with low impedance connection ($Z_{sh}$<100 kΩ) to the subject's body ensures that no displacement current penetrates the system.

Example headset devices and accompanying components for receiving neuro-response data from a user's head are disclosed herein. An example headset disclosed herein is portable and comprises a plurality of independently adjustable bands operatively coupled to a first housing encasing a processor on one end and a second housing including an adjustment mechanism on the other end.

Example headsets described herein adapt to any head shape while also applying adequate force to each of a plurality of electrodes (e.g., dry electrodes) that are coupled to the headset to provide excellent EEG readings. Some such example headsets provide a simple, cost effective and reliable solution for the use of a large number of dry electrodes. Some such example headsets ensure comfort, good electrode contact, through the hair operation, and shielding against line noise and other type(s) of noise. Examples disclosed herein also include independently adjustable components to enhance comfort and wearability. In addition, examples disclosed herein greatly increase the number of channels (e.g., electrodes) capable of gathering signals from the head, which as detailed below, enhances data gathering and analysis.

An example device is disclosed herein that includes a first elongated band coupled to a first housing to be located near a first ear of a subject and a second housing to be located near a second ear of the subject, the first elongated band comprising a first set of electrodes. The example device also includes a second elongated band coupled to the first housing and to the second housing, the second elongated band comprising a second set of electrodes. In addition, the device includes a third elongated band coupled to the first housing and to the second housing, the third elongated band comprising a third set of electrodes, and a fourth elongated band coupled to the first housing and to the second housing, the fourth elongated band comprising a fourth set of electrodes. Other example devices include fewer or more adjustable bands including, for example three, two, one, five, etc.

In some examples, each of the first, second, third and fourth elongated bands is rotatably coupled to each of the first housing and the second housing. In some examples, each of the first, second, third and fourth elongated bands is removably coupled to each of the first housing and the second housing.

In some examples, the first elongated band is to be located above a nasion (e.g., the intersection of the frontal bone and two nasal bones) of the subject at about ten percent of a distance between the nasion and an inion (e.g., the projection of the occipital bone) of the subject measured over a center of a head of the subject, the second elongated band is to be located above the nasion at about thirty percent of the distance, the third elongated band is to be located at about halfway between the nasion and the inion and the fourth elongated band is to be located above the inion at about thirty percent of the distance.

In some examples, a sum of the number of electrodes in the first, second, third and fourth electrode sets comprises at least 2000 electrodes. In some examples, the number of electrodes or channels could be 3000 electrodes or more. Also, in other examples, where less data channels are needed or desired, there may be fewer electrodes.

In some examples, each of the first, second, third and fourth elongated bands include an adjustable elastic band or strap to change a distance between the elongated band and a head of the subject.

In some examples, the device also includes one or more additional elongated bands, each additional elongated band coupled to the first housing and the second housing and each additional elongated band comprising respective additional sets of electrodes.

In some examples, the device includes an adjustment mechanism coupled to the first housing and/or the second housing to adjust a fit of the device on the subject.

In some examples, the first elongated band comprises a plurality of extensions and the plurality of electrodes of the first set are individually disposed at respective ends of the extensions. In some examples, the extensions are flexible.

In some examples disclosed herein, the electrodes comprise at least a portion of a ring. In some examples, the electrodes comprise a ball. In some examples, the electrodes comprise a hook. In some examples, the electrodes comprise a pin.

In some examples, the electrodes are removably coupled to the respective first, second, third or fourth elongated band.

In some examples, one or more of the electrodes is to compress a stratum corneum of the subject at a force of about 1 N/mm$^2$ to about 2 N/mm$^2$.

In some examples, the disclosed device includes an analog-to-digital converter to convert signals gathered by the electrodes to digital data, an amplifier to amplify the signals, and a signal conditioner to remove noise from the signals. Some such example devices also include a data processor to analyze the data in accordance with one or more analysis protocols to determine a mental state of the subject and a transmitter to transmit at least one of the digital data or the mental state.

In some examples, the device is to be worn on a head of the subject.

Also disclosed herein are example methods that include obtaining electroencephalographic data from a device comprising a first elongated band coupled to a first housing to be located near a first ear of a subject and a second housing to be located near a second ear of the subject, the first elongated band comprising a first set of electrodes having at least eight electrodes and a second elongated band coupled to the first housing and to the second housing, the second elongated band comprising a second set of electrodes having at least eight electrodes. Some devices used in some such example methods include a third elongated band coupled to the first housing and to the second housing, the third elongated band comprising a third set of electrodes having at least eight electrodes and a fourth elongated band coupled to the first housing and to the second housing, the fourth elongated band comprising a fourth set of electrodes having at least eight electrodes. Some such example methods further include analyzing the electroencephalographic data to determine a mental state of the subject.

Some example methods include converting the electroencephalographic data gathered from the electrodes to digital data, amplifying the electroencephalographic data and removing noise from the electroencephalographic data. Other example methods include analyzing the data in accordance with one or more analysis protocols to determine the mental state of the viewer and/or transmitting at least one of the digital data or the mental state.

Also disclosed herein is a tangible machine readable storage medium comprising instructions which, when read, cause a machine to at least obtain electroencephalographic data from a device comprising a first elongated band coupled to a first housing to be located near a first ear of a subject and a second housing to be located near a second ear of the subject, the first elongated band comprising a first set of electrodes having at least eight electrodes and a second elongated band coupled to the first housing and to the second housing, the second elongated band comprising a second set of electrodes having at least eight electrodes. Some such example devices also include a third elongated band coupled to the first housing and to the second housing, the third elongated band comprising a third set of electrodes having at least eight electrodes and a fourth elongated band coupled to the first housing and to the second housing, the fourth elongated band comprising a fourth set of electrodes having at least eight electrodes. Some example instructions cause a machine to analyze the electroencephalographic data to determine a mental state of the subject.

Some example instructions cause a machine to convert the electroencephalographic data gathered from the electrodes to digital data, amplify the electroencephalographic data, and remove noise from the electroencephalographic data. Some instructions cause a machine to analyze the data in accordance with one or more analysis protocols to determine the mental state and transmit at least one of the digital data or the mental state.

An example device disclosed herein includes a central body portion such as, for example, a spine and a plurality of extensions extending from the central body portion, each extension having an end coupled to an electrode. The example device also includes an adjustment band disposed along a longitudinal axis of the central body to adjust a position of the extensions.

In some examples, the adjustment band is elastic. Also, in some examples, the adjustment band has a circular cross section. In other examples, the adjustment band has a rectangular cross section. In some examples, the adjustment band is slidably disposed along the longitudinal axis.

In some examples disclosed herein, the central body portion comprises a first protrusion, a second protrusion, and a recess formed between the first protrusion and the second protrusion, and the adjustment band is disposed in the recess. In some examples, the central body portion and the extensions comprises one or more of silicone or rubber. Also, in some disclosed examples, the device includes a flexible printed circuit board encapsulated in the central body portion and extensions.

In some examples, each of the extensions is curved in a direction away from the central body portion. In some such examples, each of the extensions is curved in the same direction. Furthermore, in some examples, a first extension is located directly across the central body portion from a second extension. In some examples, the central body portion and the extensions are flexible but not elastic and the adjustment band is flexible and elastic.

In some examples, the electrodes are resilient (e.g., springy). Also, in some examples, the electrodes are removable. In some examples, the example electrodes comprise at least a portion of a ring. The example device also includes, in some examples, an array of electrodes disposed on one side of the central body portion. In some examples, the array is an embossed plate and the device includes up to 256 electrodes.

In some examples, a tightening of the adjustment band causes the electrodes to apply a force to a head of a subject wearing the device. In some examples, the force is approximately the same at each electrode.

In some examples the disclosed device includes a silver nylon coating.

Some example devices disclosed herein include an analog-to-digital converter to convert a signal obtained from an electrode to a digital signal. Also, some example devices include a signal conditioner to at least one of amplify a signal obtained from an electrode or remove noise from the signal.

In some examples, the device includes a cover partially surrounding an electrode so that a first portion of the cover is disposed on a first side of the electrode, a second portion of the cover is disposed on a second side of the electrode, and an end of the electrode to contact a tissue of a subject extends from the cover. In some examples, the electrode has a cross section of less than about 0.5 mm, a first outer end of the first portion of the cover and a second outer end of the second portion of the cover are separated by a distance of about less than 1 mm, and the end of the electrode to contact the tissues extends about less than 0.2 mm from the cover.

Another example method disclosed herein includes obtaining electroencephalographic data from a device worn by a subject, the device comprising a central body portion and a plurality of extensions extending from the central body portion, each extension having an end coupled to an electrode. The device of some such example methods also includes an adjustment band disposed along a longitudinal axis of the central body to adjust a position of the extensions. Some such example methods also include analyzing the data to determine a mental state of the subject.

Some example methods also include one or more of converting a signal obtained from an electrode to a digital signal, amplifying a signal obtained from an electrode and/or removing noise from the signal.

Another example tangible machine readable storage medium disclosed herein includes instructions which, when read, cause a machine to at least obtain electroencephalographic data from a device worn by a subject. The device of some such example instructions includes a central body portion, a plurality of extensions extending from the central body portion, each extension having an end coupled to an electrode and an adjustment band disposed along a longitudinal axis of the central body to adjust a position of the extensions. Some example instructions further cause a machine to analyze the data to determine a mental state of the subject.

Some example instructions further cause the machine to one or more of convert a signal obtained from an electrode to a digital signal, amplify a signal obtained from an electrode and/or remove noise from the signal.

Some example devices disclosed herein includes a first band comprising a first set of electrodes and a second band comprising a second set of electrodes. In some examples, the first band and the second band are to be oriented in a first direction to obtain first neuro-response data from a subject, and the first band and second band are to be oriented in a second direction to obtain second neuro-response data from the subject, the second direction being substantially orthogonal to the first.

In some examples, the first band has a first end and a second end, the second band has a third end and a fourth end, the first end is coupled to the third end, and the second end is coupled to the fourth end. Also, in some examples, the first end is coupled to the third end through a first housing and the second end is coupled to the fourth end through a second housing. In some examples, the second housing includes a processor to analyze data collected from the electrodes. In addition, in some examples, the first housing includes an adjustment mechanism to adjust a fit of the device on the subject.

In some examples, the device is to be oriented in the second direction to gather a midline reading from a brain of the subject.

Other example methods disclosed herein include obtaining first neuro-response data from a subject with a device oriented in a first direction. The device of some such example methods includes a first band comprising a first set of electrodes and a second band comprising a second set of electrodes. The example methods also include obtaining second neuro-response data from the subject with the device oriented in a second direction, the second direction approximately orthogonal to the first.

Some examples methods also include analyzing the data gathered from the electrodes using a processor disposed in a second housing. Also, some examples methods include gathering a midline reading from a brain of the subject with the device in the second direction.

Also disclosed herein is a tangible machine readable storage medium comprising instructions which, when read, cause a machine to at least obtain first neuro-response data from a subject with a device oriented in a first direction, the device comprising a first band comprising a first set of electrodes and a second band comprising a second set of electrodes. Some example instructions further cause the machine to obtain second neuro-response data from the subject with the device oriented in a second direction, the second direction orthogonal to the first.

Some example instructions further cause the machine to analyze the data gathered from the electrodes using a processor disposed in a second housing. Some example instructions further cause the machine to gather a midline reading from a brain of the subject with the device in the second direction.

Also disclosed herein are example devices that include a first set of electrodes to read an electrical signal from a tissue of a subject and a second set of electrodes to read the electrical signal. In such examples, the first set and the second set of electrodes are mechanically coupled to a headset. In addition, in the example devices, the first set of electrodes comprises a first type of electrodes, and the second set of electrodes comprises a second type of electrodes, different than the first type.

In some examples, the first type of electrodes comprises individually mounted electrodes, and the second type of electrodes includes an array of electrodes. In some examples, two or more of the electrodes in the array can be electrically shorted to form one electrode with an increased surface area. Also, in some examples, the first type of electrode comprises at least one of a partial ring, a ball point and/or a hook. In addition, in some examples, the first set is disposed along a first outer side of an elongated band and along a second outer side of the elongated band and the second set is disposed along a center axis of the elongated band.

Some example methods disclosed herein include reading an electrical signal from a tissue of a subject using a first set of electrodes. Some such example methods also include reading the electrical signal using a second set of electrodes, wherein the first set and the second set of electrodes are mechanically coupled to a headset and the first set of electrodes comprises a first type of electrodes and the second set of electrodes comprises a second type of electrodes, different than the first type.

Also disclosed herein is a tangible machine readable storage medium comprising instructions which, when read, cause the machine to at least read an electrical signal from a tissue of a subject using a first set of electrodes and read the electrical signal using a second set of electrodes. The first set and the second set of electrodes used with such example instructions are mechanically coupled to a headset and the first set of electrodes comprises a first type of electrodes and the second set of electrodes comprises a second type of electrodes, different than the first type.

Some example devices disclosed herein include a first housing comprising a magnetic lock. Some such example devices also include a first elongated band having a first end adjustably coupled to the first housing. The first elongated band comprises a first plurality of electrodes. Some such example devices also include a first adjustable strap. The first adjustable strap comprises a first magnetic fastener to magnetically link with the magnetic lock at a first engagement point to secure the first elongated band in a first position and to magnetically link with the magnetic lock at a second engagement point to secure the first elongated band in a second position.

In some examples, the device is to be worn on a head of a subject, wherein the first position is closer to a top of the head than the second position and adjustment of the first magnetic fastener from the first position to the second position tightens the first elongated band and brings the electrodes closer to the head. In some examples, the first elongated band is removably coupled to the first housing.

Some such example devices also include a second elongate band having a second end adjustably coupled to the first housing. The second elongated band comprises a second plurality of electrodes. Some such example devices also include a second adjustable strap. The second adjustable strap comprises a second magnetic fastener to magnetically link with the magnetic lock at a third engagement point to secure the second elongated band in a third position and to magnetically link with the magnetic lock at a fourth engagement point secure the second elongated band in a fourth position.

In some examples, the first elongated band and second elongated band are independently adjustable. Also, in some examples, the first elongated band and the second elongated band are independently removable.

Other methods disclosed herein include releasing a first magnetic fastener of an adjustable strap of a first elongated band of a device from a first engagement point with a magnetic lock of a first housing to unlock the first elongated band from a first position. Some such example methods also include coupling the first magnetic fastener to the magnetic lock at a second engagement point to secure the first elongated band in a second position.

Some examples methods include releasing a second magnetic fastener of an adjustable strap of a second elongated band of a device from a third engagement point with the magnetic lock to unlock the second elongated band from a third position. Some example methods also include coupling the second magnetic fastener to the magnetic lock at a fourth engagement point to secure the second elongated band in a fourth position.

Also, some example methods include one or more of independently adjusting the first elongated band and second elongated band and/or independently removing the first elongated band and the second elongated band.

Some example devices disclosed herein include a first hub and a first removable band comprising a first plurality of electrodes removably coupled to the first hub. In some such examples, the first band comprises a first cover comprising at least one of nylon or silver. The first band is washable in an automated washing machine. In some examples, the cover is stretchable. In some examples, the device includes a second removable, washable band comprising a second plurality of electrodes. Also, in some examples, the first removable band is adjustably coupled to the first hub and usable for a first subject having a first head size and a second subject having a second head size, the second head size different than the first head size.

Some example methods disclosed herein include removing a first removable band comprising a first plurality of electrodes from a first hub, the first band comprising a first cover comprising at least one of nylon or silver. Some such example methods also include washing the first band in an automated washing machine. Also, some example methods include removing a second removable, washable band comprising a second plurality of electrodes from the first hub and washing the second band in the automated washing machine. In addition, some example methods include adjusting the first removable band relative to the first hub to fit a first subject having a first head size and/or readjusting the first removable band relative to the first hub to fit a second subject having a second head size, the second head size different than the first head size.

Turning now to the figures, FIGS. 1-4 show an example headset 100. The example headset may be used for instance, to gather medical information from a patient in a medical or a home environment, to control aspects of a game or other entertainment, to provide data as part of a fitness regime, to collect audience measurement data, to control remote devices and/or multiple other uses. The example headset 100 of FIG. 1 includes a plurality of independently adjustable bands, each band comprising a plurality of electrodes for receiving signals from a head of a user, subject, viewer and/or panelist. As used herein, a participant is a person who agreed to be monitored. Typically, a participant provides their demographic information (e.g., age, race, income, etc.) to a monitoring entity (e.g., The Nielsen Company) that collects and compiles data about a topic of interest (e.g., media exposure). More specifically, the headset 100 of the illustrated example includes a first band 102, a second band 104, a third band 106 and a fourth band 108. Each of the bands 102-108 includes a plurality of electrodes. In the illustrated example, the electrodes are partially ring-shaped electrodes. The ring-shaped electrodes may have, for example, a diameter of less than about 3 mm and a length less than about 3 mm. The bigger and wider the dimensions of an electrode, the more force needed to sufficiently apply the electrode to the scalp. In some examples, the electrodes have a diameter of about 1 mm to about 2 mm. However, many other types, sizes and/or shapes of electrodes may be additionally or alternatively used as discussed in further detail below. In the example of FIG. 1, the bands 102-108 are intended to extend over the head of a user from the left side of the head to the right side of the head. Each of the bands 102-108 comprises an elongated structure with a longitudinal axis. In this example, each band 102-108 takes the form of a spine-shaped structure 110, 112, 114 and 116, respectively. Each of the spines 110, 112, 114, 116 supports an elastic adjustment band or strap 118, 120, 122 and 124, respectively. Each of the bands 102-108 is rotatably and removably coupled on one side to a first housing 126 and rotatably and removably coupled on the other side to a second housing 128. For example, the bands 102-108 may include a pivot type connection and/or a snap fastener to plug the bands 102-108 into the headset. In other examples, the bands are fixedly coupled to the headset. In the example shown, the first housing 126 may be placed near the right ear of a user and the second housing 128 may be placed near the left ear of the user so that the bands 102-108 are disposed over the head of the user for reading electrical activity along the scalp. The headset 100 of the illustrated example also includes an additional support band 130, which is adjustable and may be, for example, elastic or any other suitable material that may be used for tightening and securing the headset 100 around the back of the head of a user. In the example shown, the headset 100 includes four bands. However, in other examples, the headset 100 may include fewer or more (e.g., three or less or ten or more) adjustable bands. Each band may carry about eight to about 256 or more electrodes per band.

In the example of FIG. 1, the bands 102-108 are rotatably and removably coupled to the first and second housings 126 and 128 to allow a user to adjust the position of the bands 102-108 over the head of the user. The bands 102-108 of this example may be rotated toward the inion (the projection of the occipital bone) or the nasion (the intersection of the frontal bone and two nasal bones) of the user to position the electrodes in specific locations for measuring electrical activity. Each of the spines 110-116 of FIG. 1 is comprised of a flexible material such as, for example, plastic, rubber, polyurethane, silicone and/or any other suitable material. The flexibility of the example spines 110-116 allows the headset 100 to sit comfortably on the head of a user. Further, the elastic straps 118-124 of the illustrated example are supported by the spines 110-116 and may be pulled to tighten the spines 110-116 downward and, thus, to increase the pressure of the electrodes against the scalp of a user. In the illustrated example, the elastic straps 118-124 are flexible and elastic. In addition, the elastic straps 118-124 of FIG. 1 are slidably and translatably coupled to the spines 110-116. Further, in the example of FIG. 1 the entire headset 100 and/or the individual bands 102-108 may be cleaned in a typical washing machine for routine cleaning and/or to disinfect and sterilize the headset 100 such as, for example, between uses or between users. In some examples there are various templates of headsets for differently sized heads. People have different head sizes based on age, sex, race and/or genetics. For example, human heads may range from about 54 cm to about 65 cm in circumference. In some examples there may be two or three template headsets. For example, a first template may accommodate heads of about 56 cm in circumference, a second template for heads of about 59 cm in circumference and a third template for heads of about 62 cm in circumference. In these examples, the center band (e.g., along the midline) may be about 23 cm, about 25 cm and about 26 cm, respectively. Thus, in some examples, the templates may include bands of multiple sizes that differ in length from about 1 cm to about 2 cm between different templates. The different template sizes are used as a coarse adjustment when fitting a headset on a subject. The adjustment of the elongated bands is then used to perfect the fit as a fine adjustment, which is detailed more below.

In the example shown, the first housing 126 includes an example adjustment mechanism 132 (shown in FIG. 10) to adjust the length of the elastic straps 118-124. The elastic straps 118-124 of the illustrated example may be pulled tight via the adjustment mechanism 132 to position the respective bands 102-108 and tighten the spines 110-116 downward toward the scalp. An example adjustment approach is disclosed in greater detail below in connection with FIG. 10.

In the example shown, the second housing 128 supports electrical components 134 such as, for example, a processor for processing the signals from the electrodes, disclosed in further detail below. In some examples, the processing occurs at the headset as an all-in-one or self-contained system. In other examples, some of the processing occurs at the headset and some processing occurs remotely after the headset transmits data or semi-processed results to a remote site such as, for example, via a wireless connection. In still other examples, all data is streamed to a remote analyzer for processing. The electrical components 134 of the illustrated example are used to, for example, convert the electroencephalographic data from analog data to digital data, amplify the electroencephalographic data, remove noise from the data, analyze the data, and transmit the data to a computer or other network. The second housing 128 of the illustrated example includes hardware and software such as, for example, an amplifier, a signal conditioner, a data processor and/or a transmitter for transmitting signals to a data center or a computer. Each of the spines 110-116 of the illustrated example are communicatively coupled to the electrical components including the example processor via a wired connection and/or wirelessly. In other examples the electrical components 134 are supported in the first housing 126 and the adjustment mechanism 132 is supported on or in the second housing 128.

Figure 4A:
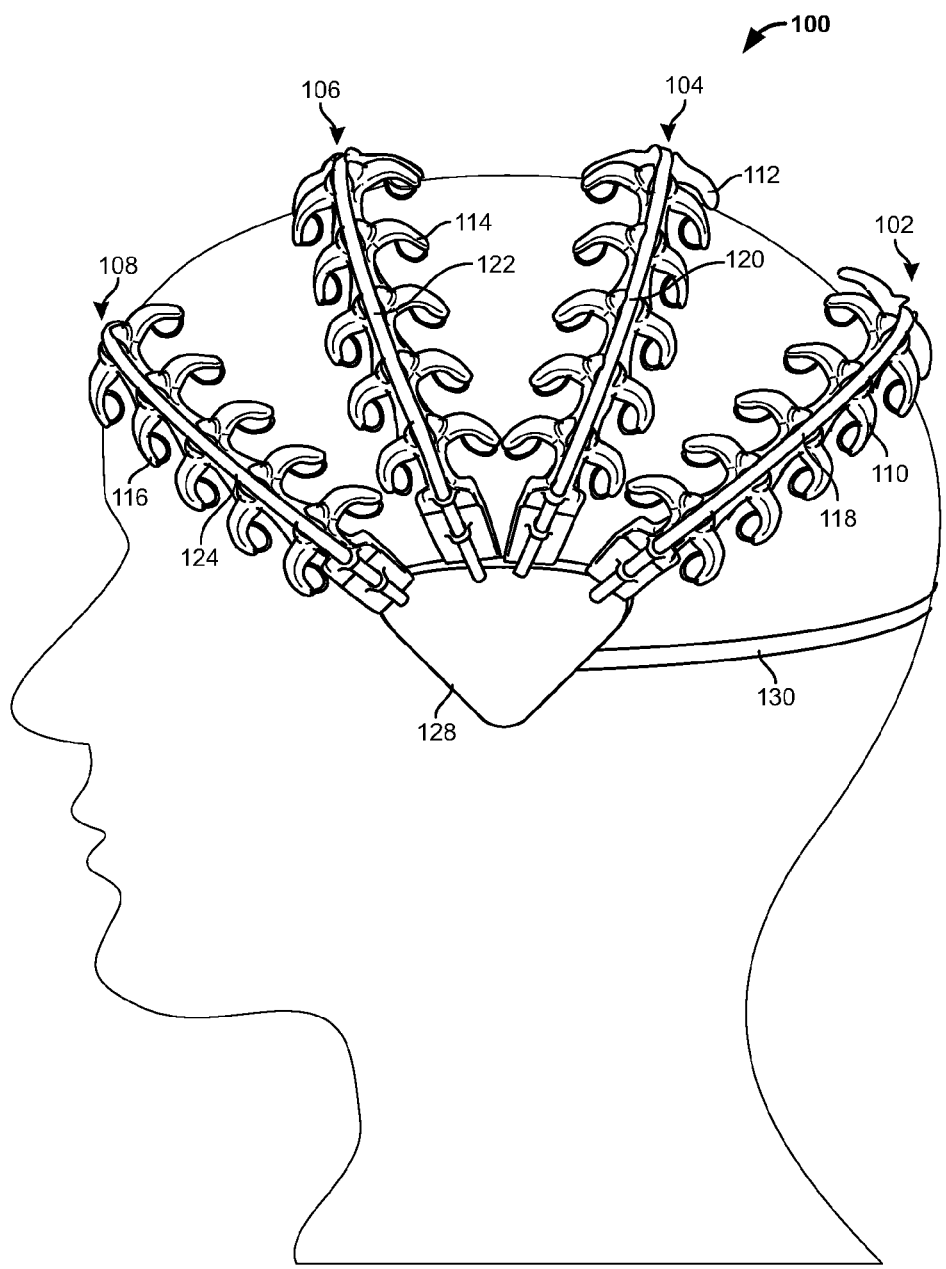
FIG. 4A is a perspective view of the headset of FIG. 1 in an example orientation.

FIG. 4A illustrates a perspective view of the headset 100 worn on the head of a user. As shown, the bans 102-108 traverse over the head from a left side to a right side. The location of the bands 102-108 may be adjusted and the elastic straps 118-124 may be tightened to tighten the bands 102-108 downward on the user's head. In the example shown, the additional support band 130 is stretched around the back of the head and may be pulled tight or adjusted to secure the headset 100 to the head of the user.

Figure 4B:
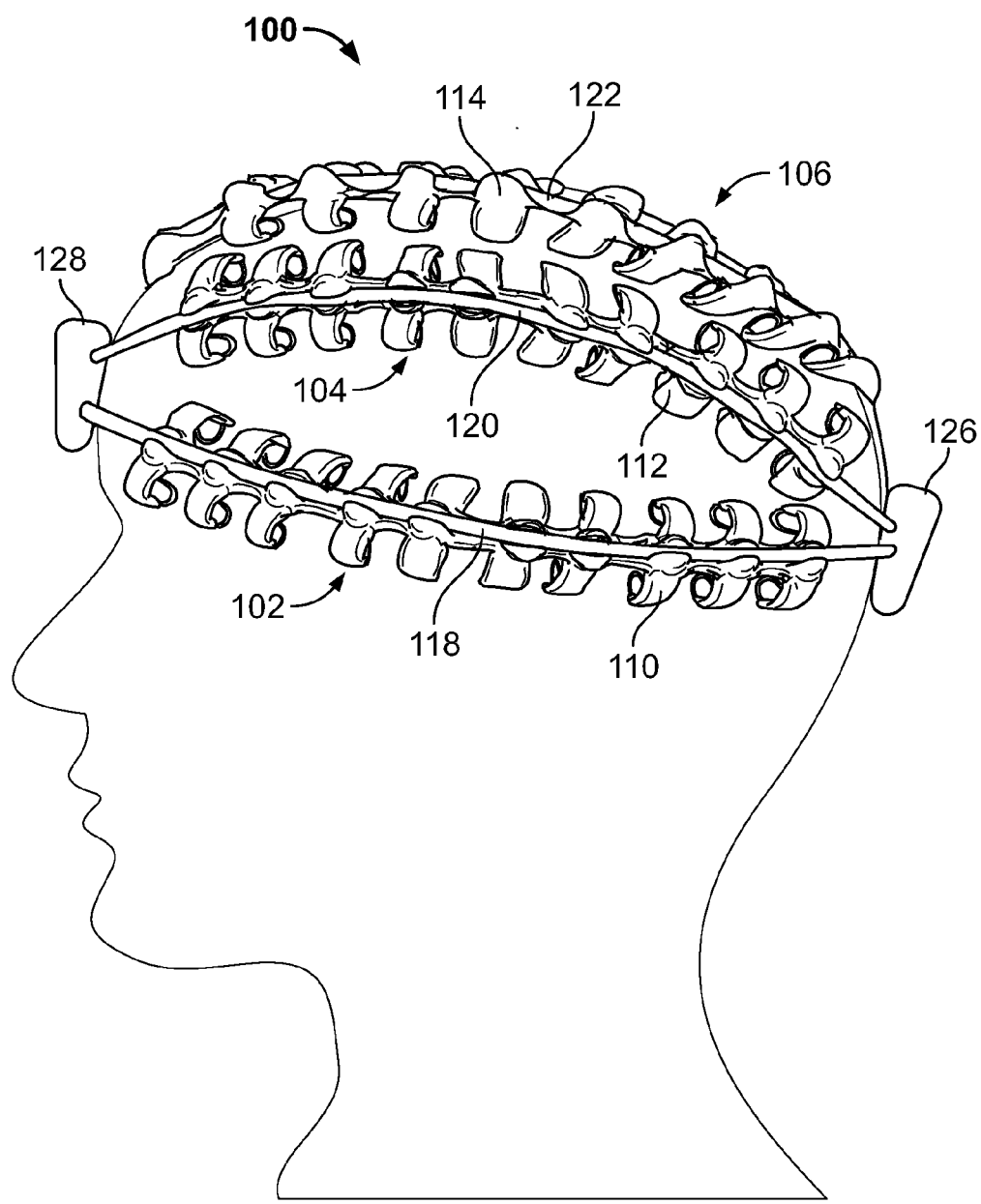
FIG. 4B is a perspective view of the headset of FIG. 1 in another example orientation.

As shown in FIG. 4B, in addition to being worn in the side-to-side orientation explained above, the headset 100 of the illustrated example may be worn in a front to back orientation, wherein the first housing 126 or the second housing 128 is placed over the forehead of a user and the bands 102-108 traverse to the other of the second housing 128 or the first housing 126, which is disposed on the back of the user's head. The bands 102-108 may be laterally adjusted and/or tightened individually for optimum reading. The orientation of FIG. 4 facilitates a midline reading of by the headset 100.

Figure 5:
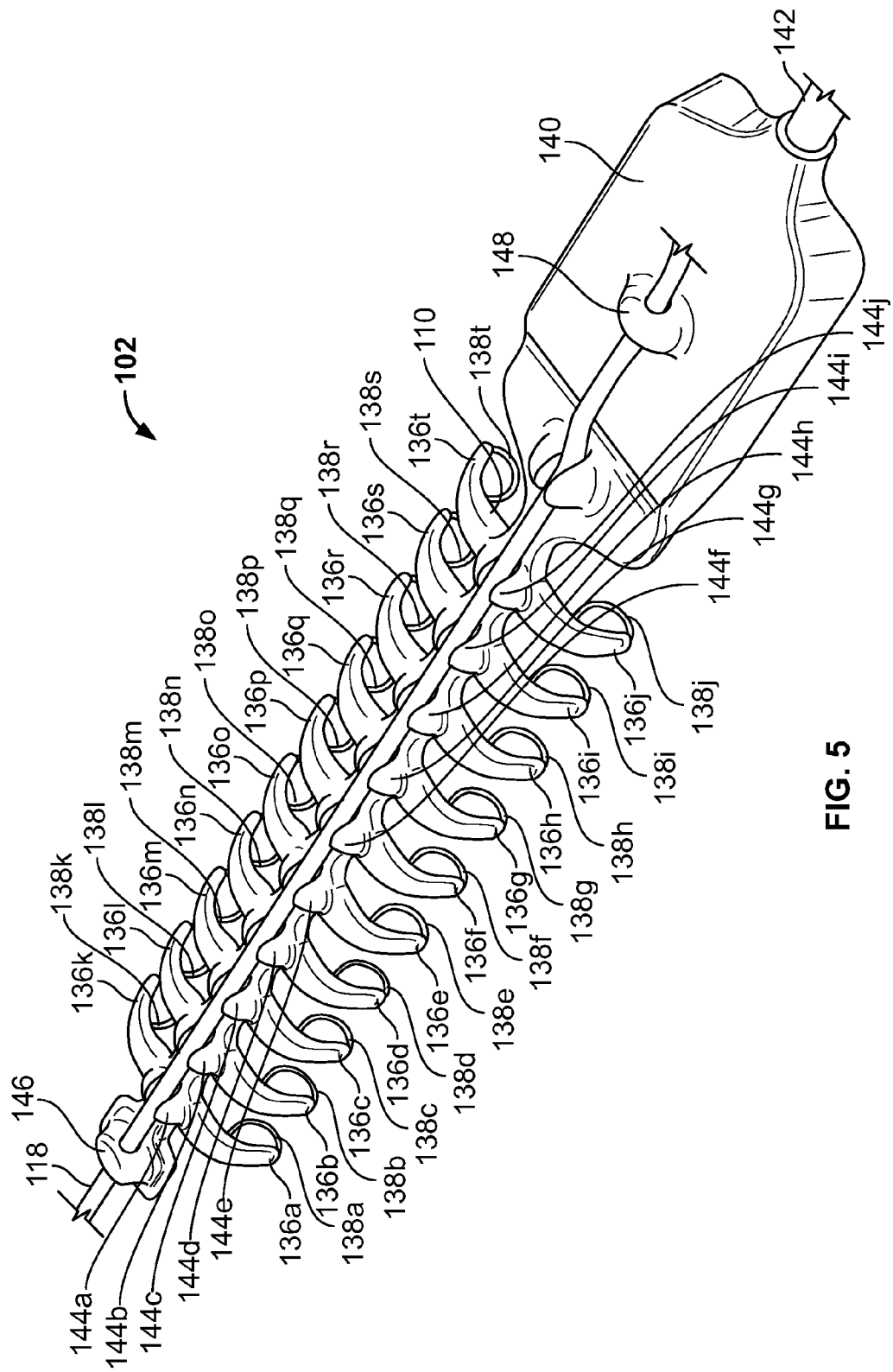
FIG. 5 is a perspective view of an example adjustable band or spine of the headset of FIG. 1.

FIG. 5 illustrates the example band 102 that may be used with the headset 100. As seen, the first band 102 is comprised of the first spine 110 and the first elastic strap 118. The first spine 110 is designed in a spine-like structure having a plurality of opposed extensions, 136a-136t, similar to that of a spine and vertebrae arrangement. Each of the extensions 136a-136t is coupled to a partially ring-shaped electrode 138a-138t, respectively. The extensions 136a-136t are flexible to retract and bend as the first band 102 is tightened down over the head of a user. In the example shown in FIG. 5, the electrodes 138a-138t are molded within the extensions 136a-136t of the first spine 110. However, in other examples, the electrodes 138a-138t may be removably coupled (e.g., snapped on) to the extensions 136a-136t. Each of the electrodes 138a-138t has its own channel running through the spine 110. Also, in some examples, the readings from multiple electrodes may be averaged together to increase the effective surface area between the electrodes and the scalp and decrease impedance, as disclosed in more detail below. The first spine 110 further includes a housing 140 that may contain individual amplifiers and analog-to-digital converters for each of the electrode channels. The spine 110 also includes a wire 142 to communicatively couple the electrodes 138a-138t to the processor 134 and/or to the other electrical components of the second housing 128 for processing. In other examples the spine 110 includes a wireless transmitter and power supply, for example in the housing 140, for wirelessly transmitting data to the processor 134 in the second housing 128 or to another processor outside of the headset 100.

The topside of the first spine 110 includes a plurality of runners 144a-144j, which are extensions or protrusions for guiding and securing the first elastic strap 118 along the topside of the first spine 110. In the illustrated example, the runners 144a-144j are formed in pairs of two elongated runners extending along opposite sides of the elastic strap 118. In other examples, the runners 144a-144j are implemented by one or more elongated circular tubes running over the elastic strap 118. The first spine 110 further includes a first eye 146 and a second eye 148. In the example shown the second eye 148 is coupled to the housing 140. The first elastic strap 118 is disposed between the runners 144a-144j along the longitudinal axis on top side of the first spine 110 and also through the first and second eyes 146, 148. The first and second eyes 146, 148 assist in maintaining the position of the elastic strap 118 on the spine 110. The first elastic strap 118 is slidably engaged along the top side of the first spine 110 to slide as the first elastic strap 118 is stretched and pulled tight or released. In the example shown in FIG. 5, the first elastic strap 118 has a circular cross-section. However, in other examples, the first elastic strap 118 has a rectangular, elliptical, or any other cross-section shape. In some examples, the elastic strap 118 is shaped to enhance shielding of the electronic signals propagating through the spine 110.

In the example shown in FIG. 5, the first band 102 includes 20 electrodes on the first spine 110. However, in other examples, the first spine 110 may carry other numbers of electrodes (e.g., 256 or more individual electrodes).

Figure 6:
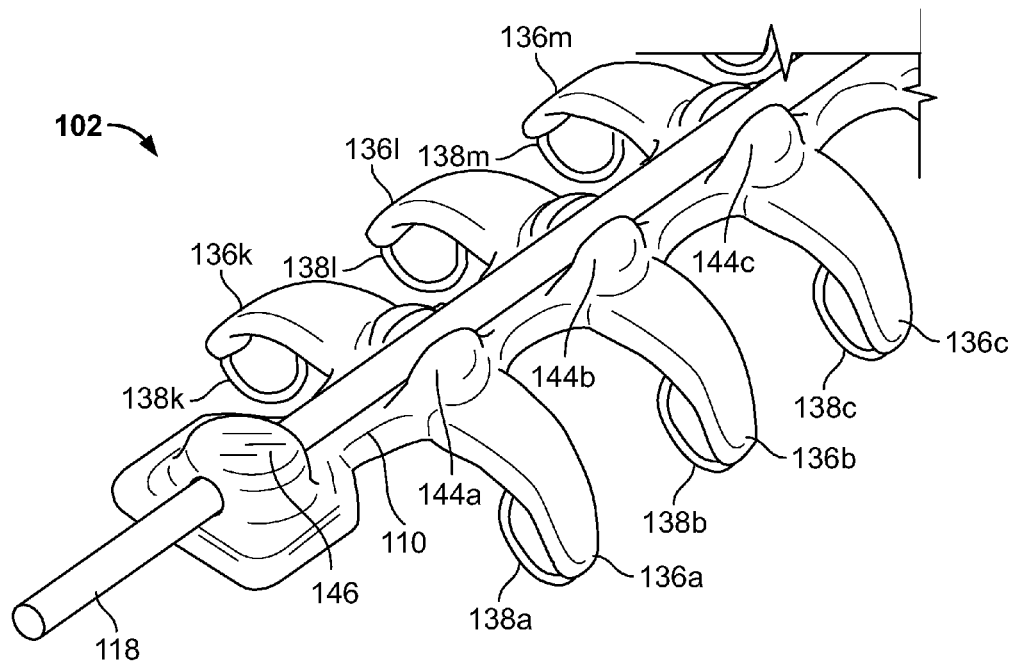
FIG. 6 is an enlarged view of an end of the example spine of FIG. 5.

FIG. 6 is an enlarged view of a portion of the first band 102. As seen in FIG. 6, the extensions 136a-136c and 136k-136m are curved slightly downward, which positions the electrodes 138a-138c and 138k-138m downward toward the scalp. As shown in FIG. 6, the first elastic strap 118 is disposed along the top of the first spine 110 and held in place by the runners 144a-144c and the first eye 146. Each of the extensions 136a-136c and 136k-136m is coupled to a respective one of the electrodes 138a-138c and 138k-138m. As the first elastic strap 118 is pulled tighter, the elastic strap 118 is effectively shortened, thereby creating a downward force on the extensions 136a-136c and 136k-136m, which flex upward or bow outward to force the electrodes against the scalp of a user. The example bands 102-108 are designed to create a force of about 1 $N/mm^2$ to about 2 $N/mm^2$ on the scalp of a user. In some examples, the applied force is the same for each electrode.

Figure 7:
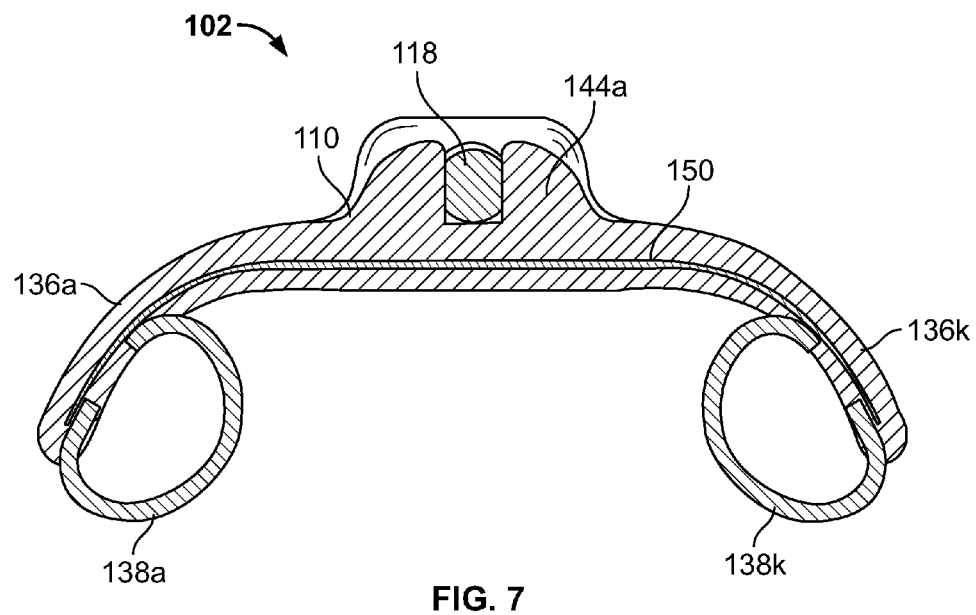
FIG. 7 is a cross-sectional view of the example spine of FIG. 5.

FIG. 7 is a cross-sectional view of the first band 102 having the first spine 110 and the first elastic band 118. The extensions 136a and 136k are curved downward. The electrodes 138a and 138k are partially ring-shaped electrodes coupled to the underside of the extensions 136a and 136k, respectively. The ends of the electrodes 138a and 138k are molded within the first spine body 110 and operatively coupled to a printed circuit board (PCB) 150, which runs through the first spine 110. Each of the electrodes 138a-138t (shown in FIG. 5) is communicatively coupled to the PCB 150. The PCB 150 of the illustrated example includes three electronics layers (e.g., layers including at least one electrical component or circuit line) and one shielding layer.

Figure 8A:
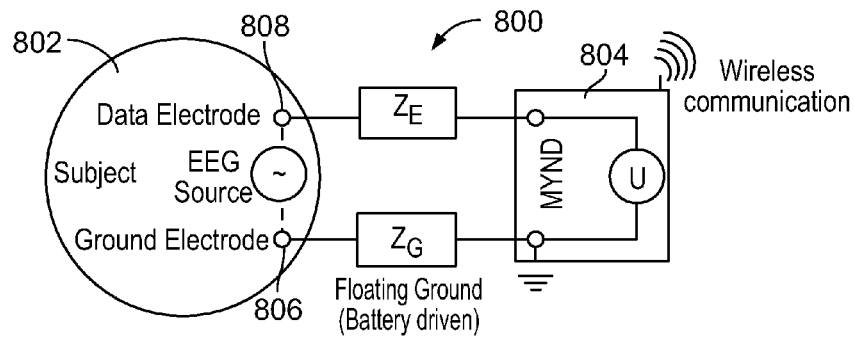
FIG. 8A is a circuit diagram for an example EEG system.
Figure 8B:
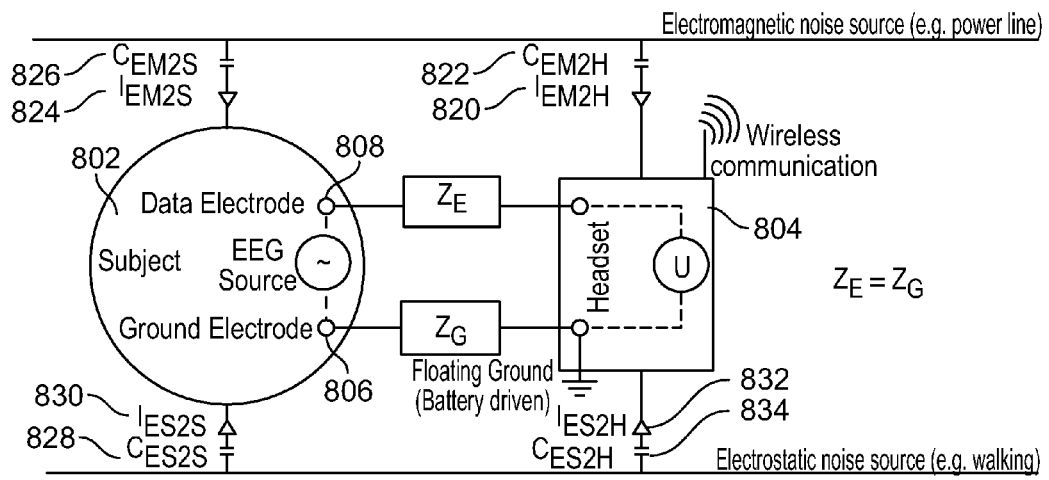
FIG. 8B is a circuit diagram for an example EEG system with wet electrodes.
Figure 8C:
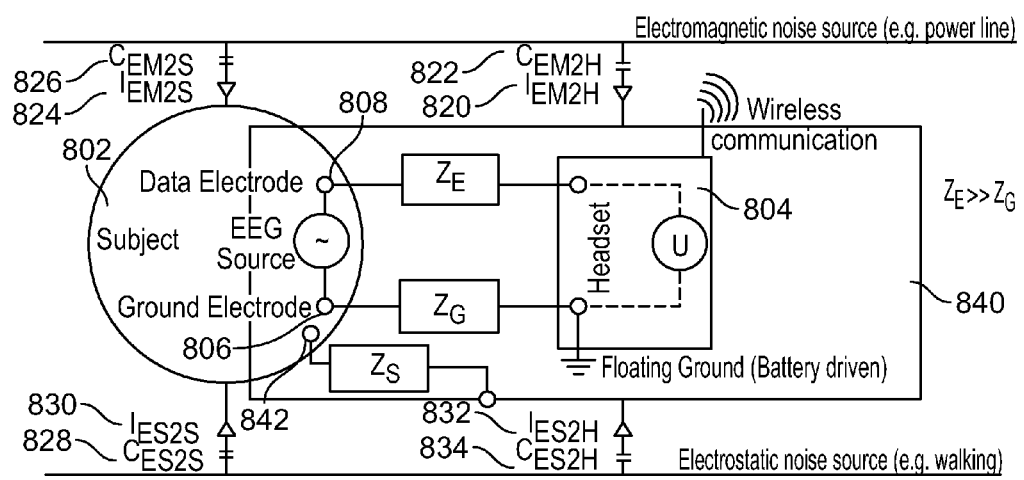
FIG. 8C is a circuit diagram for an example EEG system with dry electrodes in accordance with the teachings of this disclosure.

Several example methods of shielding are disclosed herein to reduce or eliminate electromagnetic interference with EEG readings including, for example, the reduction of impedance to reduce and/or eliminate the need for external shielding in some instances. The examples disclosed herein enable high-resolution EEG measurement with high impedance skin-electrode interfaces and inter-electrode high impedance mismatches. In some examples, the high-resolution measurement is achieved by battery powered EEG measurement devices such as, for example, the headsets disclosed herein, that may include floating driven low-impedance ground, wireless communication and the example disclosed shielding techniques. FIGS. 8A, 8B and 8C illustrate the effect of impedance through example electrical circuit representations of an EEG system without external noise sources (FIG. 8A), a wet electrode EEG system with external noise sources (FIG. 8B), and a dry electrode EEG system with external noise sources (FIG. 8C), which represents the example systems disclosed herein.

FIG. 8A illustrates an example EEG system 800 in which a subject 802 is coupled to an EEG measurement device 804 such as, for example, the headsets disclosed herein. In this example, the headset 804 is a wireless EEG measurement device. The potential between a driven ground electrode 806 and a data electrode 808 is measured by applying biopotential electrodes on the head of the subject 802. FIG. 8A represents an ideal or theoretical situation in which there is no external noise such as, for example, a completely shielded room in which the subject never moves. In such a system, measurements between the data electrode 808 and the ground electrode 806 are indicative of the signal of from the EEG source (e.g., the subject's brain) without noise artifacts.

In a real world environment (FIGS. 8B and 8C), there are external noises from electromagnetic (e.g., power lines) or electrostatic (e.g., walking) sources. Because of the low signal amplitudes of EEG data (for example, about 1 μV to about 100 μV) and high electrode-skin impedances (for example, greater than about 100 kΩ), external noise sources play a significant role in the quality of the EEG data. Electromagnetic induced noise can penetrate the EEG signal over several pathways. For example, an electric field can induce displacement current 820 ($I_{EM2H}$, electromagnetic source to headset) that flows through the associated capacitance 822 ($C_{EM2H}$, electromagnetic source to headset), into the electrode leads of the headset 804, the electrode-skin interface or individual components of the EEG device (e.g. amplifier, power supplies, etc.). Another source of electromagnetic noise is the common mode voltage on the subject's body. A displacement current 824 ($I_{EM2S}$, electromagnetic source to subject), flows through stray capacitance 826

($C_{EM2S}$, electromagnetic source to subject). Stray capacitance is the capacitance between any two adjacent conductors. The size of this capacitance is determined by how close the subject is to power sources. The noise attributable to the stray capacitance can be as large as, for example if the subject grasps an insulated power cord, 20V.

Another source of noise is electrostatic. Friction creates charge that is stored in the capacitance 828 ($C_{ES2S}$, electrostatic source to subject) between the body and ground. For example, a third person who is electrostatically charged can induce a static voltage and associated current 830 ($I_{ES2S}$, electrostatic source to subject), into the subject if he/she moves close to the subject. Displacement current 832 ($I_{ES2H}$, electrostatic source to headset), is also injected and capacitance 834 ($C_{ES2H}$, electrostatic source to headset), is also induced from the external electrostatic noise to the headset 804.

The external noise capacitively injects displacement current 820 ($I_{EM2H}$), 832 ($I_{ES2H}$) in the subject 802 or the headset 804, which will be converted by the impedances of the data electrodes ($Z_E$) and ground electrode ($Z_G$) into additional noise that can be magnitudes higher than the signal of interest. If there are equal impedances, the noises will cancel out. In a low impedance wet system (FIG. 8B), the conversion of displacement current into additional noise is minimized such that noise can be kept under acceptable values. Typically, however, it is not achievable for the impedances of the data electrodes ($Z_E$) and ground electrode ($Z_G$) to be equal.

In a system including dry electrodes with high impedance electrode-skin interfaces (e.g., greater than about 100 kΩ) (FIG. 8C), the impedance from the data electrode ($Z_E$) is much greater than the impedance from the ground electrode ($Z_G$). In this configuration, the displacement currents 820 ($I_{EM2H}$), 832 ($I_{ES2H}$) would typically flood the system with noise. However, the examples disclosed herein couple a conductive material that has an electrode-skin impedance of less than about 100 kΩ to the body of the subject 802. Example conductive materials include an aluminum sheet and/or a silver coated nylon. The conductive material and the subject 802 form a shield 840 such that the EEG device (e.g., headset 804) is capacitively decoupled from the environment. The shield 840 is coupled to the subject via a shield electrode 842 that has a low impedance ($Z_S$). The shield 840 and shield electrode 848 effectively encapsulate the headset 804. The displacement currents 820 ($I_{EM2H}$), 832 ($I_{ES2H}$) that result from external noise sources such as electromagnetic sources (e.g., power lines) or electrostatic noise sources (e.g., such as walking of the subject or near other people) flows through the path of least resistance (e.g., through the shield electrode with low impedance $Z_S$) and, thus, these displacement currents 820 ($I_{EM2H}$), 832 ($I_{ES2H}$) are not visible at the input of the EEG measurement devices (e.g., headset 804).

Figure 9:
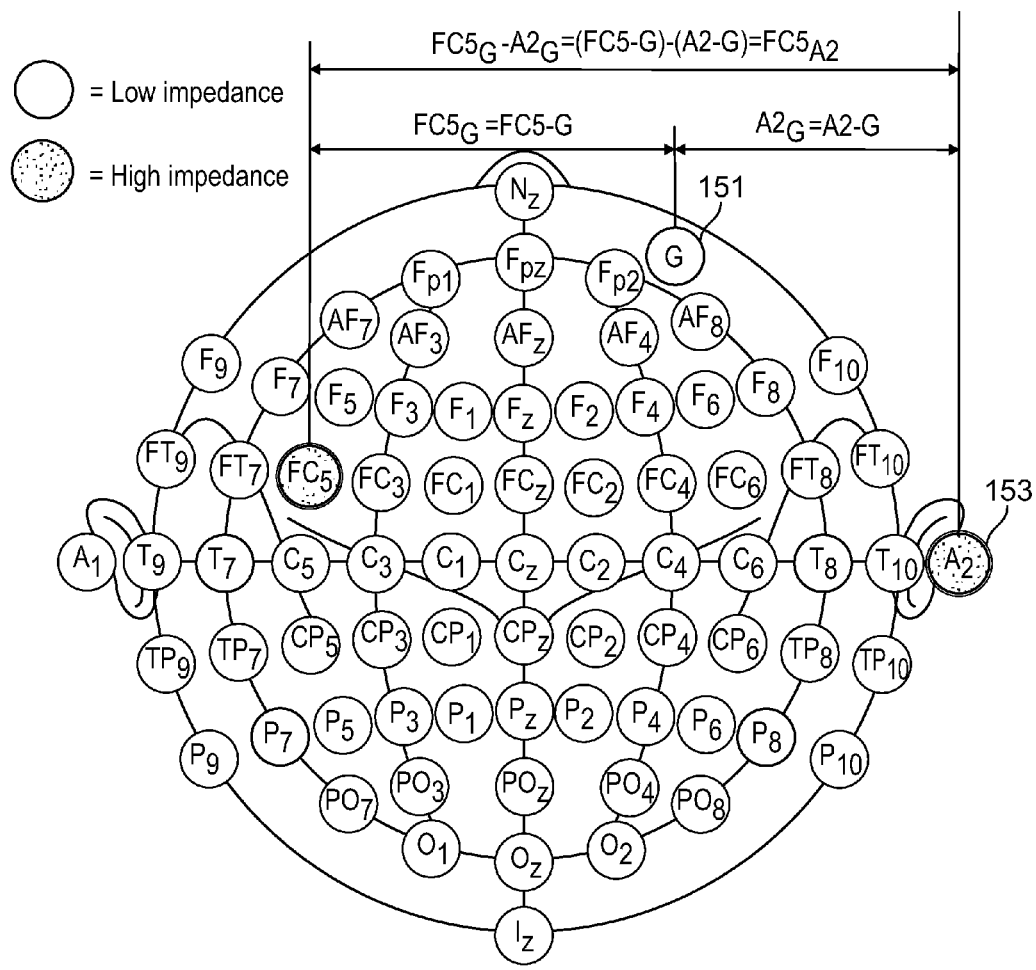
FIG. 9 is a schematic view of a top of a head illustrating example electrode and ground placement locations.

In some examples disclosed herein, a low-impedance electrode-skin interface for ground and shield electrodes is realized by introducing an unconventional location for the ground electrode. For example, FIG. 9 is a schematic view of a top of head showing example electrode and ground placement using the example headset of FIG. 1 or other example headsets disclosed herein. There are several abbreviations in the diagram including "N" for nasion, "F" for frontal (e.g., in relation to the frontal lobe of a brain, which is the area located at the front of each cerebral hemisphere), "A" for ear lobe, "C" for center (e.g., in relation to a center area of the brain), "T" for temporal (e.g., in relation to the temporal lobe of the brain, which is located inferior and posterior to the frontal lobe at each cerebral hemisphere), "P" for parietal (e.g., in relation to the parietal lobe of the brain, which is located posterior to the frontal lobe), "O" for occipital (e.g., in relation to the occipital lobe of the brain, which is located at the back of the head), "I" for inion, and the subscript "z" for readings taken along the midline of the brain.

As shown in FIG. 9, a driven ground electrode 151, which in this example is a low impedance dry electrode, and an electrode for the shield are placed at the forehead. A second data electrode 153 is placed at a typical ground location such as, for example, an earlobe or a mastoid. The forehead is an unconventional location for the ground electrode 151 because of the underlying muscle movement. Ear lobes and mastoids are relatively quiet areas (e.g., relatively free from of electrode activity) of the scalp that are free of hair, which lowers the impedance at these positions, have low brainwave activity and are less susceptible to artifacts from muscle movement such as, for example, movement of the jaw muscles. Subtracting this additional added data channel 153 from every other data channel (in either the digital domain or the analog domain) will cancel the unwanted effect of the ground electrode at the forehead. This is referred to as referencing, where the "0" potential of the system has to be shifted (or referenced). The equation in FIG. 9 shows that the effect of the ground electrode 151 at the forehead drops out when the data electrode 153 is subtracted from a data channel (e.g., data channel FC5). Thus, a low impedance electrode-skin connection (e.g., less than about 100 kΩ) is achieved without the use of gel at the forehead of a subject.

In addition to enabling the system to have a dry low-impedance interface, these examples also enhance the common mode rejection ratio (CMRR) because common signals (noise) will be attenuated by the subtraction. CMRR is where devices tend to reject input signals common to two input leads. A high CMRR is desired in applications where the signal of interest is a small voltage superimposed on potentially large voltage offset.

Examples disclosed herein obtain EEG readings of high quality with low noise for several reasons. Some such examples are self-contained units and, therefore, the EEG platform of these examples is electrically disconnected or decoupled from external electric sources. Additionally or alternatively, examples disclosed herein include a conductive layer that is coupled to the human body (e.g., the shield of FIG. 8C) and encases the EEG platform (e.g., the headset 804 of FIG. 8C). Having a low impedance coupling between the conductive layer and the human body and a high impedance to the EEG platform also capacitively disconnects the EEG platform from the environment such that external sources cannot penetrate the EEG platform and capacitive coupled displacement currents are not detectable or visible at the input of the EEG platform, as disclosed above. Thus, the EEG platform is electrically isolated from external noise sources. Examples disclosed herein provide low electrode-skin impedance such as, for example, as low as about 100 kg.

In other examples, additional shielding is provided. In some such examples, each electrode includes an individual shield, the cables are shielded, and/or all electronics include further shields. In some examples, the headset includes a conductive paint to enhance shielding. Also, in some examples, the headset includes a cover such as, for example, a silver-coated nylon, which also enhanced shielding.

Furthermore, as disclosed herein, some example systems utilize reduced shielding or no shielding because the electrodes gather data with such low impedance that the signal-to-noise ratio is high enough to enable the data to be processed without additional shielding. Also with such low impedance, noise sources become less relevant. The low capacitance of the components in some example systems reduces the need for additional shielding and, thereby reduces the complexity of the system. Low impedance and low capacitance may be achieved, for example, with miniature signal lines in the flexible circuit board 150 and via the use of small profile electrodes that are kept close to the head as disclosed herein.

Figure 10:
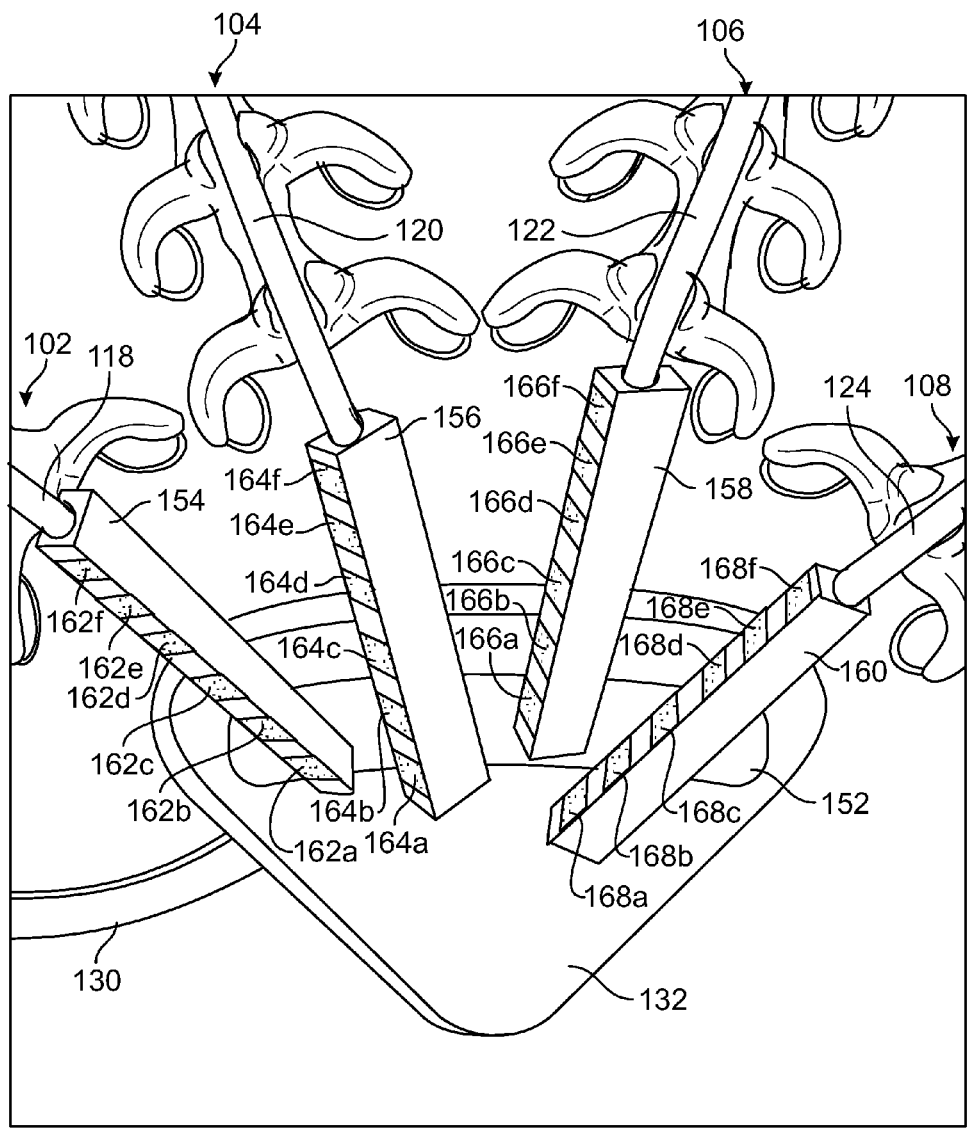
FIG. 10 is an enlarged view of an example adjustment mechanism shown on the headset of FIG. 1.

FIG. 10 is an enlarged view of the example adjustment mechanism 132, which can be incorporated into the first or second housing 126, 128. The adjustment mechanism 132 of the illustrated example comprises a magnetic block or lock 152. Each of the elastic straps 118-124 is coupled to an attachment strip 154-160, respectively. Each of the attachment strips 154-160 comprise a plurality of vertically arranged magnetic elements, 162a-162f, 164a-164f, 166a-166f and 168a-168f, respectively. Each of the attachment strips 154-160 is magnetically releasable and lockable with the magnetic lock 152 at a plurality of positions. In the illustrated example, there are multiple positions for coupling each one of the attachment strips 154-160 to the magnetic lock 152. The magnetic elements 162a-162f, 164a-164f, 166a-166f, and 168a-168f on the attachment strips 154-160 allow a user to adjust the length of the elastic straps 118-124. For example, if a user wants to tighten the band 102 for comfort and/or signal connection, the user releases the corresponding attachment strip 154 from engagement with the magnetic lock 152, pulls the attachment strip 154 in a downward direction to another magnetic element 162a-162f, which pulls the elastic strap 118 and causes the spine 110 of the band 102 to move in a direction closer to the user's head causing the respective electrodes to more closely engage the user's scalp. The user then engages the magnetic strip 154 with the magnetic lock 152 to lock the band 102 in the desired position. If the user wants to loosen the band 102 for comfort, to adjust the electrode placement and/or signal connection, and/or to remove the headset 100, the user may release the attachment strip 154 from the magnetic lock 152 and moves the attachment strip 154 in an upward direction to loosen the elastic strap 118 and to cause the spine 110 of the band 102 to move in a direction away from the user's head thereby causing the respective electrodes to more lightly engage or to disengage the user's scalp. The user then reengages the attachment strip 154 with the magnetic lock 152 to lock the band 102 in a desired position. The same process may be repeated with any other band. To fully remove a band, the corresponding magnetic strip is removed from the attachment lock 152 and not reengaged. Also, in some examples, there may be magnetic balls or endpoints to each elastic strip that engage one of a plurality of magnetic locks supported on the adjustment mechanism 132. In such examples, the bands are adjustable into multiple positions defined by the position of the magnetic locks. In other examples, the elastic bands on the spine may be adjusted in any other fashion.

FIGS. 11A, 11B, 11C and 11D illustrate example electrodes that may be used with the bands 102-108 of the headset 100. Sensor (electrode) geometries and materials affect the impedance characteristics of the signal connections. In some examples the electrodes are formed, for example, of silver or silver chloride, which may provide, for example about 10 MΩ of impedance per square millimeter of contact surface. Other materials with other impedance per area values may additionally or alternatively be used.

Figure 11A:
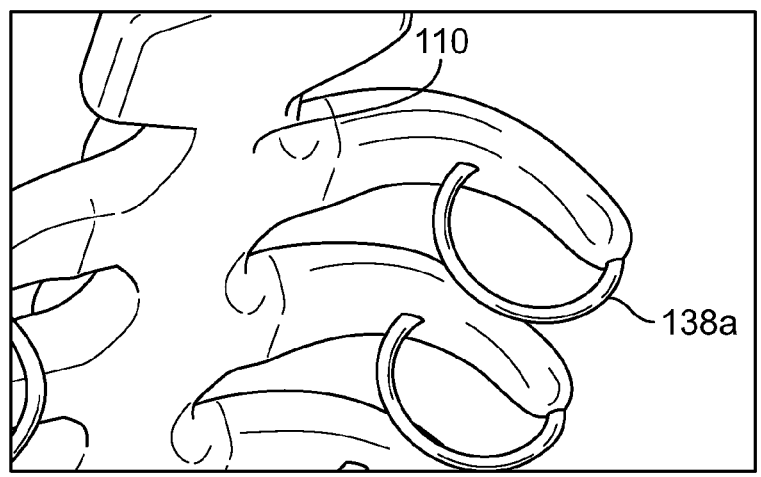
FIG. 11A is a perspective view of an example electrode of FIGS. 1-7.

The example ring-shaped electrode 138a shown in FIG. 11A comprises a smooth curved element. In the example of FIG. 11A, the ends of the ring-shaped electrode 138a are molded into the body of the spine 110. However, in other examples, the electrodes are removably coupled to the body of the spine 110. The electrode 138a of the illustrated example may be constructed of any electrically conductive element. The electrodes in the illustrated example are less than about 3 mm in diameter and greater than about 3 mm in length. This configuration allows the electrode to penetrate the hair of a user and make contact with the scalp. The ring-shaped electrode 138a of the illustrated example is sufficiently resilient (e.g., springy) to flex and adjust when pressure is applied downward toward the head.

Figure 11B:
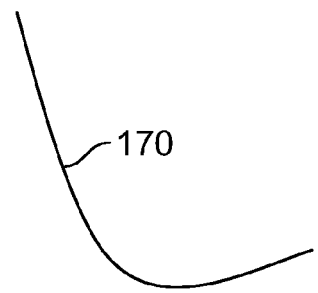
FIGS. 11B and 11C are front views of two alternative example electrode designs.
Figure 11C:
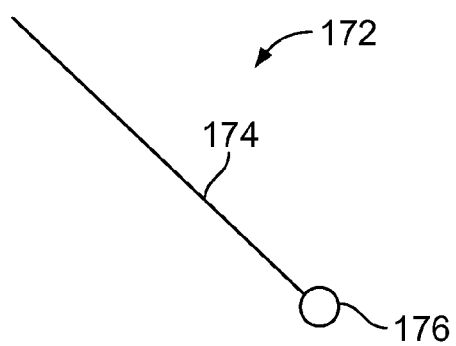

The example shown in FIG. 11B is a hook-shaped electrode 170. Similar to the example ring-shaped electrode 138a of FIG. 10, the example hook-shaped electrode 170 of FIG. 11B is curved, thereby allowing the electrode to penetrate the hair and lay against the scalp of a user. FIG. 11C illustrates an example ball electrode 172. The example ball electrode 172 of FIG. 11C comprises a shaft 174 and a ball 176. The ball 176 of the illustrated example can easily penetrate the hair and touch the scalp of a user. In some examples, the ball electrode has an impedance of about 1.3 MΩ, the ball had a diameter of about 1.8 mm, and, when pressed into the tissue, the ball has an effective contact area of about 7.7 mm² Increasing the size of the electrodes increases the contact area and further decreases impedance. For example, if a ball electrode with four times the diameter of the example ball electrode described above is used, the contact area will be about 30 mm², and the impedance will be reduced to about 300 kΩ.

Figure 11D:
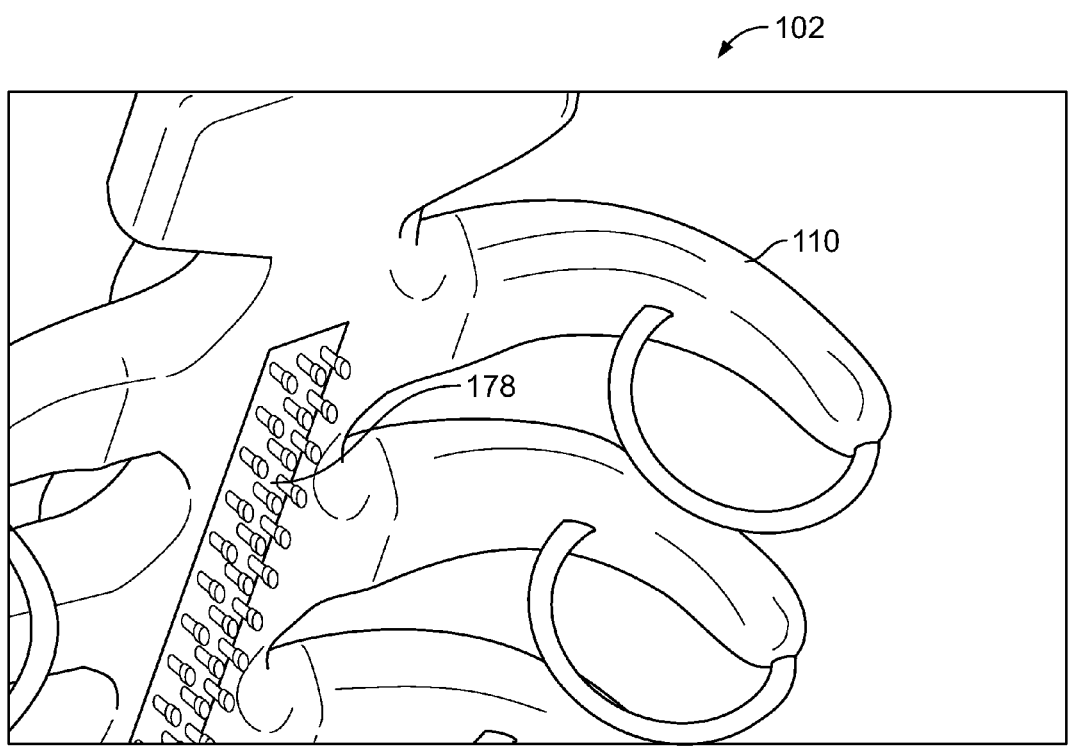
FIG. 11D is a perspective view of an example central electrode array plate.

FIG. 11D is an example implementation of the first spine 110 equipped with a central array plate 178. In this example, there is one array plate 178. However, in other examples, there may be a plurality of array plates. The bottom side of the first spine 110 of the illustrated example includes the central array plate 178 to increase the amount of electrodes touching the scalp. The central array plate 178 of the illustrated example is embossed to include a plurality of pin-like individual electrodes. As the first elastic strap 118 (shown in FIG. 1) is tightened, reflective pressure from the scalp forces the extensions 136a-136t (shown in FIG. 5) of the first spine 110 to flex outward so the bottom of the first spine 110 is moved closer to the scalp. As the bottom of the first spine 110 approaches the scalp, some or all of the individual electrodes on the central array plate 178 penetrate the hair and touch the scalp of the user. In the example shown in FIG. 11D, the central array plate contains approximately 256 individual electrodes or more. Each electrode has its own channel that is communicatively coupled to the processor via the PCB 150. With the large number of electrodes included on the example array plate 178, the number electrodes disposed at the extension on the spines, and the number of spines included in a headset 100, the example headset 100 gathers signals from a very large number of channels. If, for example, the headset 100 includes ten spines, the number of channels could easily surpass 2000 or 3000 channels. This large number advantageously provides a larger amount of data from multiple areas of the brain to create a clearer and more comprehensive picture of brain activity. This large amount of channels also provides an oversampling, which enables virtual movement of an electrode as disclosed below.

In some examples, the array plate 178 enables the headset 100 to include about twenty-four electrodes within about a 1.5 cm radius. The electrodes within the same area likely collect the same signal or substantially similar signals. In some examples, the quality of the signals collected through the electrodes can be improved by effectively increasing the surface area of the electrode contact with the scalp by combining two or more electrodes and/or by averaging two or more of the signals collected via the electrodes within the radius for use as a single value.

In some examples, individual electrodes may be coupled in a parallel connection to effectively increase the contact area of the electrodes by the number of electrodes coupled in parallel. Because of the parallel connection, if one electrode has a high impedance or otherwise gathers a poor signal, the effect of that electrode is small on the whole parallel configuration. The coupling of electrodes reduces the impedance and the effect of thermal noise. In some examples, the electrodes are fixedly coupled in parallel. In other examples, two or more electrodes are coupled via a switching circuit, which can be selectively activated to short out one or more electrodes to effectively increase the surface area contact between the electrodes and the tissue on the scalp. By shorting out one electrode and increasing the effective surface area of a second electrode, the impedance is lowered, which also enables the second electrode to effectively read higher frequency bands.

Figure 12A:
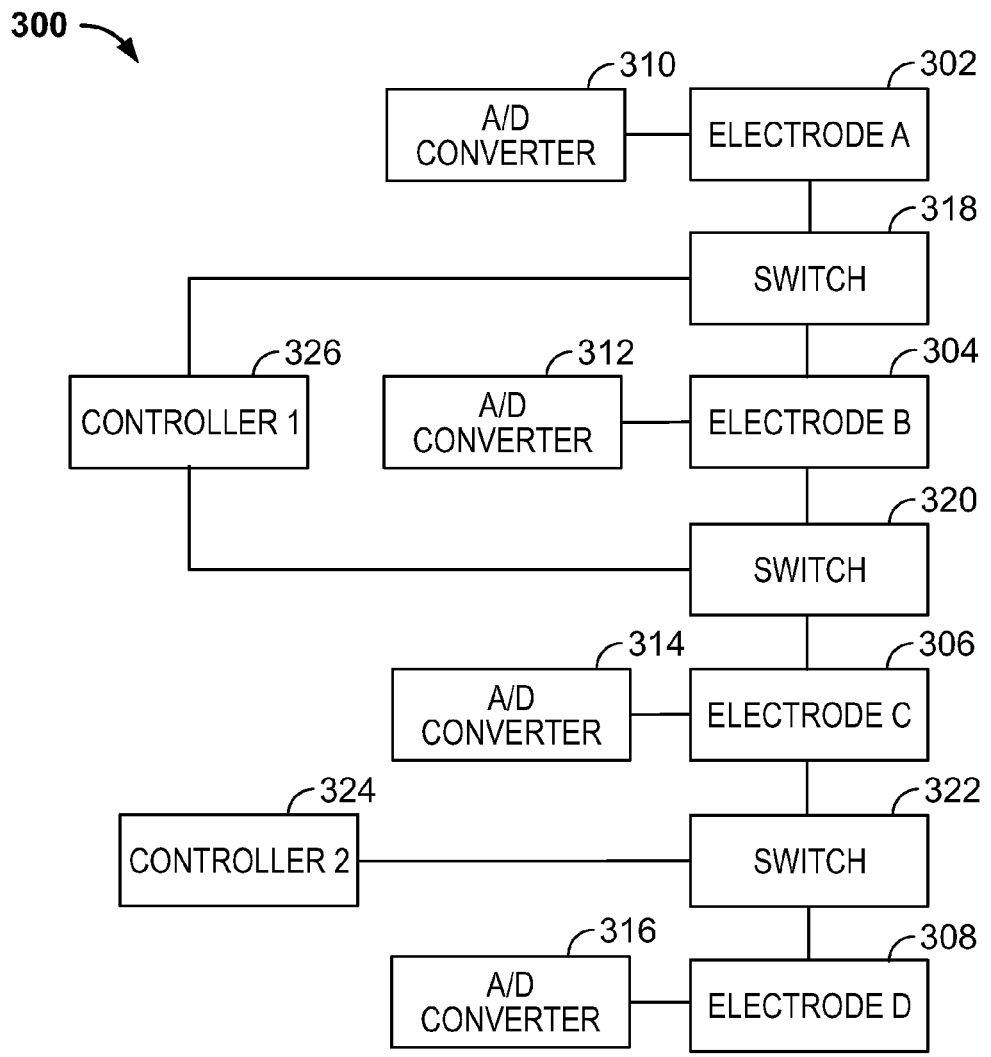
FIG. 12A is a block diagram of an example switching circuit.

An example switching circuit 300 is shown in FIG. 12A. The example circuit 300 includes a plurality of electrodes, Electrode A 302, Electrode B 304, Electrode C 306 and Electrode D 308. In other examples there may be other numbers of electrodes including, for example, two, five, ten, fifty, etc. These electrodes 302, 304, 306, 308 may represent a subset of the plurality of electrodes disposed within a small area such as, for example, the area defined above with about a 1.5 cm radius. In the example, each electrode 302, 304, 306, 308 is coupled to a respective analog-to-digital converter 310, 312, 314, 316. In other examples, the electrodes 302, 304, 306, 308 may be coupled to the same analog-to-digital converter or a different number of analog-to-digital converters. In addition, in some examples, the electrodes 302, 304, 306, 308 may additionally or alternatively be coupled to other signal processing components such as, for example, the components disclosed below with FIGS. 36 and 37.

In addition, as shown in FIG. 12A, multiple electrodes such as, for example, adjacent electrodes may be coupled via switches. For example, Electrode A 302 and Electrode B 304 may be selectively electrically coupled via a first switch 318. Electrode B 304 and Electrode C 306 may be selectively electrically coupled via a second switch 320. Also, Electrode C 306 and Electrode D 304 may be selectively electrically coupled via a third switch 322. In other examples, additional and/or alternative electrode(s) may be coupled via the switches 318, 320, 322 and/or additional switch(es). In some examples, one or more of the switches includes a transistor. Also, in some examples, a controller controls each switch (e.g., controller 2 324 controls switch 322). In some examples, a single controller controls multiple switches (e.g., controller 1 326 controls switches 318, 320). The switches 318, 320, 322 can be opened to electrically decouple the associated electrodes, or the switches 318, 320, 322 can be closed to electrically couple associated electrodes. Electrically coupling two electrodes is a shorting out that increases the contact area of the shorted out electrode, which as noted above, decreases impedance and increases signal quality.

Figure 12B:
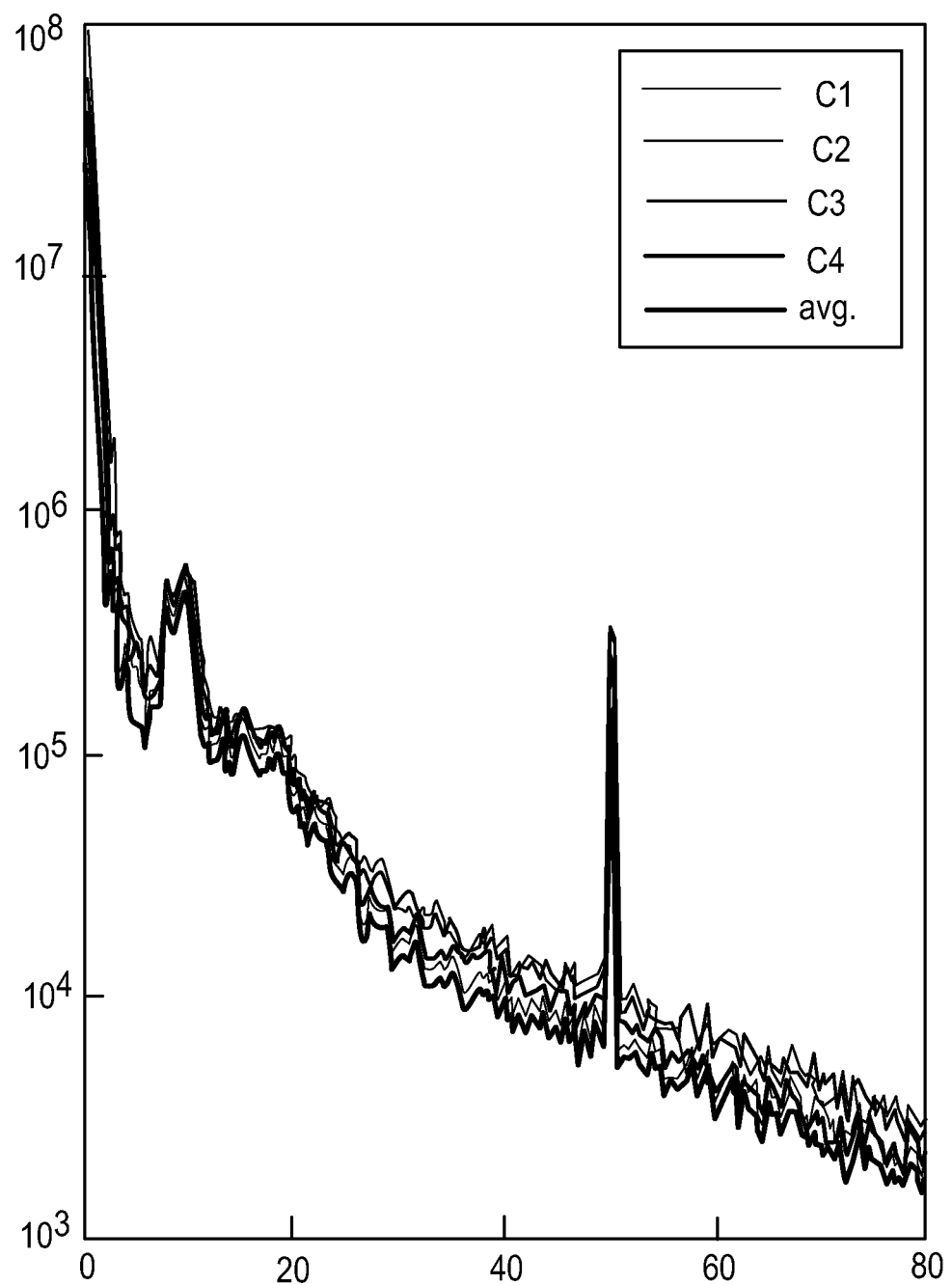
FIG. 12B is a graphical representation of averaging of multiple channels of data.

As noted above, another method to increase signal quality includes averaging signals from two or more channels (e.g., electrodes). The averaging will increase the signal-to-noise ratio by reducing both thermal noise and amplifier noise. An example graphical representation of signal averaging is shown in FIG. 12B. As shown, there are four channels (C1, C2, C3, C4) of signals represented on the logarithmic scale. The signal from each channel includes the EEG signal plus the background noise. The first peak, at 10 Hz, shows the subject closing his eyes. Thus, electrostatic noise from the contractions of the subject's muscles is increased. Another increase is background noise is the second peak, at 50 Hz, which is electromagnetic noise due to power lines (e.g., power line frequency in Europe). As shown in FIG. 12B, the average of the four channels, which is shown as the darkest line has the lowest values on the y-axis and, thus, carries the lowest amount of noise. As the frequency level increases, the noise reduction in the averaged signal increases such that the average is more purified from noise than any of the individual component signals. This disparity grows as frequency increases. Thus, averaging signals enables higher frequencies to be read including, for example frequencies as high as about 100 Hz or even about 120 Hz, with less noise interference.

A combination or hybrid system may also be used that combines the coupled electrodes and the averaged signals. For example, a set of electrodes within a specific area may include subsets of electrodes that are electrically coupled via fixed parallel couplings or via selective switching. Each subset may provide a high quality signal. Signals from two or more subsets may be averaged to further increase signal quality.

Furthermore, due to a large number of electrodes, a user or an automated analyzer could determine which electrodes are most optimally in contact with the scalp and gathering the clearest signal by comparing the signal quality from the electrodes. Electrodes in the vicinity with lower signal quality may then be ignored. In addition, if an electrode has a relatively weak signal and an adjacent electrode has a stronger signal, the user or automated analyzer can utilize the stronger signal and ignore the weaker signal. This enables the user or machine (e.g., the analyzer) to virtually move the electrode to the stronger signal gathering position without having to physically adjust any mechanical components (i.e., without physically adjusting the location and orientation of the bands).

FIGS. 13A and 13B are cross-sectional views of example electrodes in contact with the scalp of a user. FIG. 13A shows a traditional electrode 180 that is unable to penetrate a user's hair. Thus, the traditional electrode 180 does not make sufficient physical contact with the user's scalp, which increases the impedance and reduces signal quality. In the example of FIG. 13B, an electrode 182 is smaller and thinner than the traditional electrode 180 and is dimensioned to penetrate the hair to contact the scalp of a user directly without any hair strands and/or hair follicles underlying the electrode 182. The example electrode 182 also includes a cover 184 (e.g., a shield) for shielding the electrode from electromagnetic interference (e.g., electromagnetic waves and noise) from the environment. The example cover 184 of FIG. 13B is sufficiently wide such that it cannot penetrate all the hair on a user's head and, thus, enhances a user's comfort. However, in the illustrated example, the electrode 182 is smaller and thinner than the cover 184 so that the electrode 182 does penetrate the hair to contact the user's scalp. Thus, the electrode 180 can compress at least a portion of the strateum corneum. If the electrode is too thick, it will not be able to penetrate the hair of a user (as shown in the traditional electrode 180 of FIG. 13A). If the electrode is too thin, and sticks out too far, the electrode will create a sharp pain on the user's head. In the example shown in FIG. 13B, the electrode 182 has a diameter $d_2$ of about 0.5 mm and the cover 184 has an outside diameter $d_1$ of about 1 mm. In the example of FIG. 13B the electrode 182 has length $l_1$ that extends about 0.2 mm from the cover 184 to contact the scalp of a user. Because the electrode 182 is able to make direct contact with the scalp without the interference of hair, there is less impedance and less noise in a signal gathered from the electrode 182 than from the electrode 180 shown in FIG. 13A. Therefore, less shielding is needed. In general, the smaller the diameter of the electrode in contact with the scalp, the more discomfort a user may experience. However, if the distance between adjacent electrodes is decreased and/or the number of electrodes in a specific area is increased, the force or tension applied to the headset and, thus to the electrodes, is split amongst the electrodes, which increases comfort for the user and, thus may offset the effect of the small electrode points.

FIG. 14 is a circuit diagram 1400 of an example electrode to skin contact, which may represent, for example, $Z_E$ of FIGS. 8A-C. The coupling between the skin and the electrode is a layered conductive and capacitive structure represented by combinations of parallel resistor and capacitor (RC) elements connected in series. The parallel capacitor $C_d$ 1402 and resistor $R_d$ 1404 represent the coupling impedance of the double layer at the skin-electrode interface, and the parallel capacitor $C_i$ 1406 and resistor $R_i$ 1408 represent the input impedance of the amplifier 1410. The resistor $R_s$ 1412 represents the minimum series contact resistance and the voltage $V_{pol}$ 1414 represents the DC polarization potential of the body.

Figure 15:
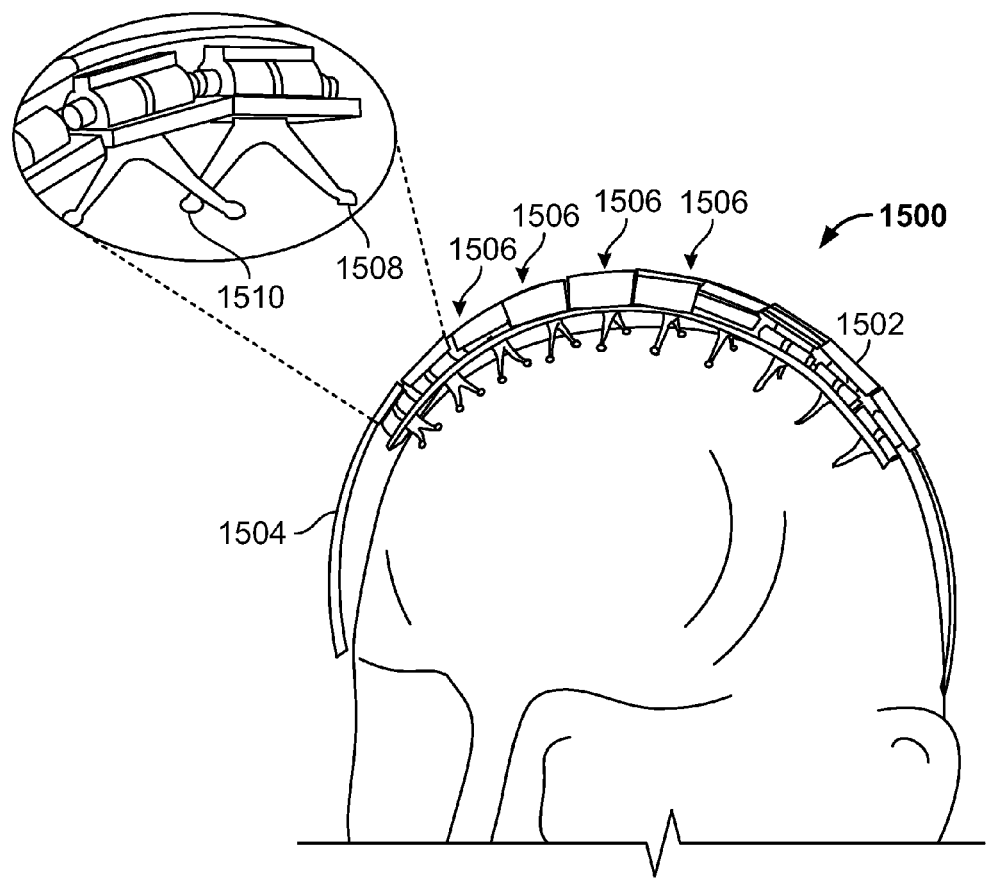
FIG. 15 is a perspective view of an alternative band or spine and an alternative electrode constructed in accordance with the teachings of this disclosure.
Figure 16:
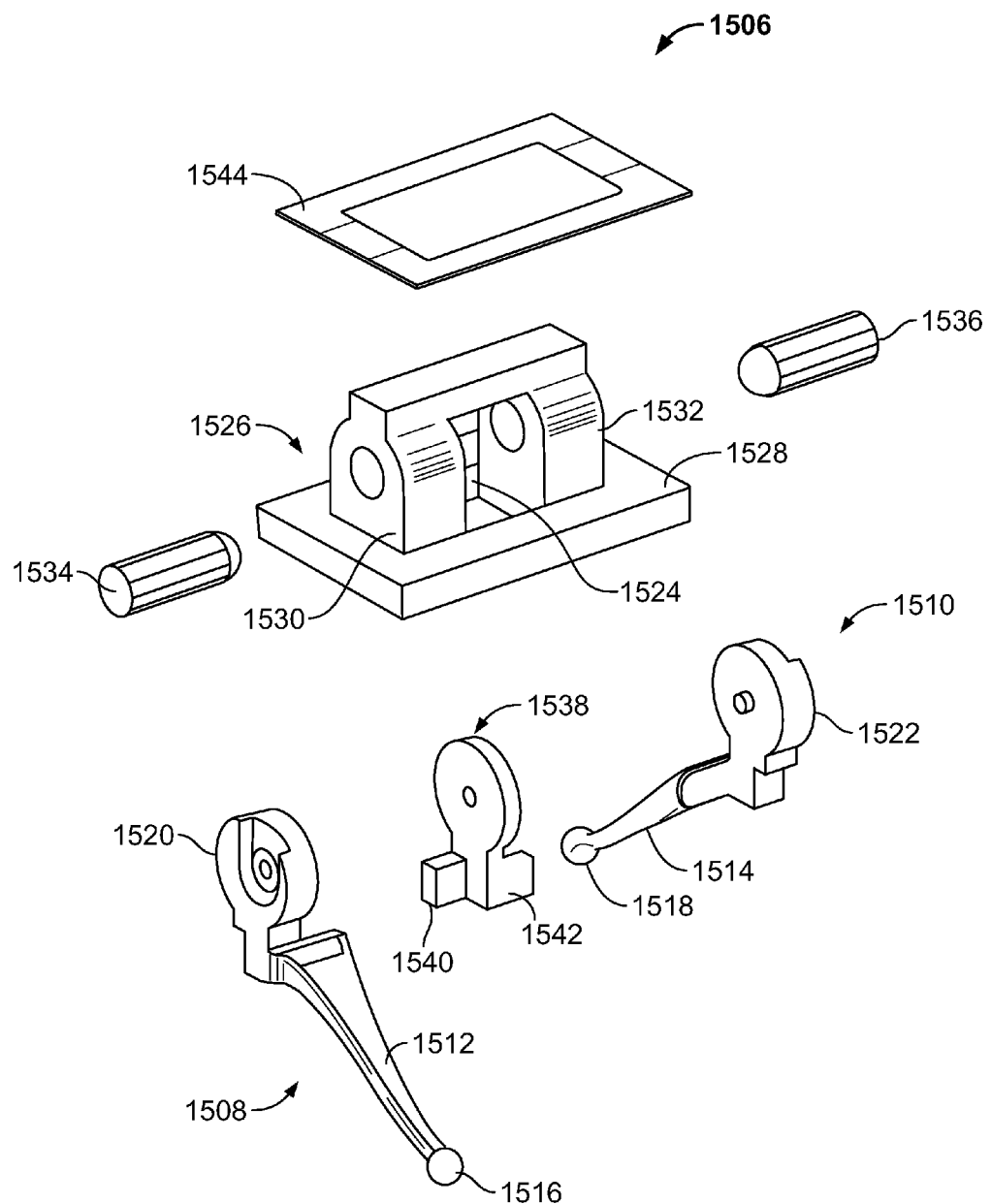
FIG. 16 is an exploded view of the example electrode of FIG. 15.

FIGS. 15 and 16 illustrate an alternative spine and electrode constructed in accordance with the teachings of this disclosure. An example band 1500 has a spine body 1502 and an elastic strap 1504 to tighten the spine body 1502 against the head of a user. The spine body 1502 includes a plurality of individual electrode units 1506, each having a pair of leg-shaped electrodes 1508 and 1510 pivotably coupled to the unit 1506 and projecting downwards to aim the electrodes 1508 and 1510 at the scalp of a user.

An exploded view of an example electrode unit 1506 is shown in FIG. 16. The electrode unit 1506 of the illustrated example includes the electrodes 1508 and 1510, each of which includes a shaft 1512, 1514 and a contact ball 1516, 1518, respectively. Each of the electrodes 1508, 1510 further comprises a mounting ring 1520, 1522, respectively. The mounting rings 1520, 1522 are disposed within an opening 1524 within a housing 1526. The housing 1526 comprises a plate 1528 and sleeves 1530, 1532. The mounting rings 1520, 1522 of the electrodes 1508, 1510 fit between the sleeves 1530, 1532. In the illustrated example, the shafts 1512, 1514 protrude below the plate 1528 and are angled outward from each other to contact the scalp of a user. The electrodes 1508, 1510 are pivotably coupled the housing 1526 via respective pins 1534, 1536, which are disposed through the sleeves 1530, 1532 and through the respective holes in the mounting rings 1520, 1522. In the example of FIG. 16, a spring 1538 is disposed between the mounting rings 1520, 1522 and the sleeves 1530, 1532. The spring 1538 includes tabs 1540, 1542. As the electrode unit 1506 is tightened down toward the head, the electrodes 1508, 1510 rotate and flex upward. The ends of the shafts 1512, 1514 adjacent the mounting rings 1520, 1522 are pressed against the respective tabs 1540, 1542 of the spring 1538, which biases the electrodes 1508, 1510 back down toward the head. The electrodes 1508, 1510 flex and maintain a consistent pressure downward on the scalp of a user when force is applied to the electrode unit 1506. In the illustrated example, the spring 1538 comprises a nonconductive material to keep the signals gathered from the first electrode 1508 separate from the signals gathered from the second electrode 1510.

The electrode unit 1506 of the illustrated example allows a user to easily remove and replace individual electrodes. The top of the plate 1528 includes a flexible PCB 1544, which communicatively couples the electrodes 1508, 1510 to a processor for data processing. The PCB and the electrodes 1508, 1510 may be coupled to the processor and/or any other analysis unit via a wired or wireless connection. As shown in FIG. 15, the band 1500 of the illustrated example includes multiple individual electrode units 1506. Each electrode unit is hinged to the adjacent electrode unit, such that the entire band 1500 may curve around and lay against the head of a user.

Figure 17:
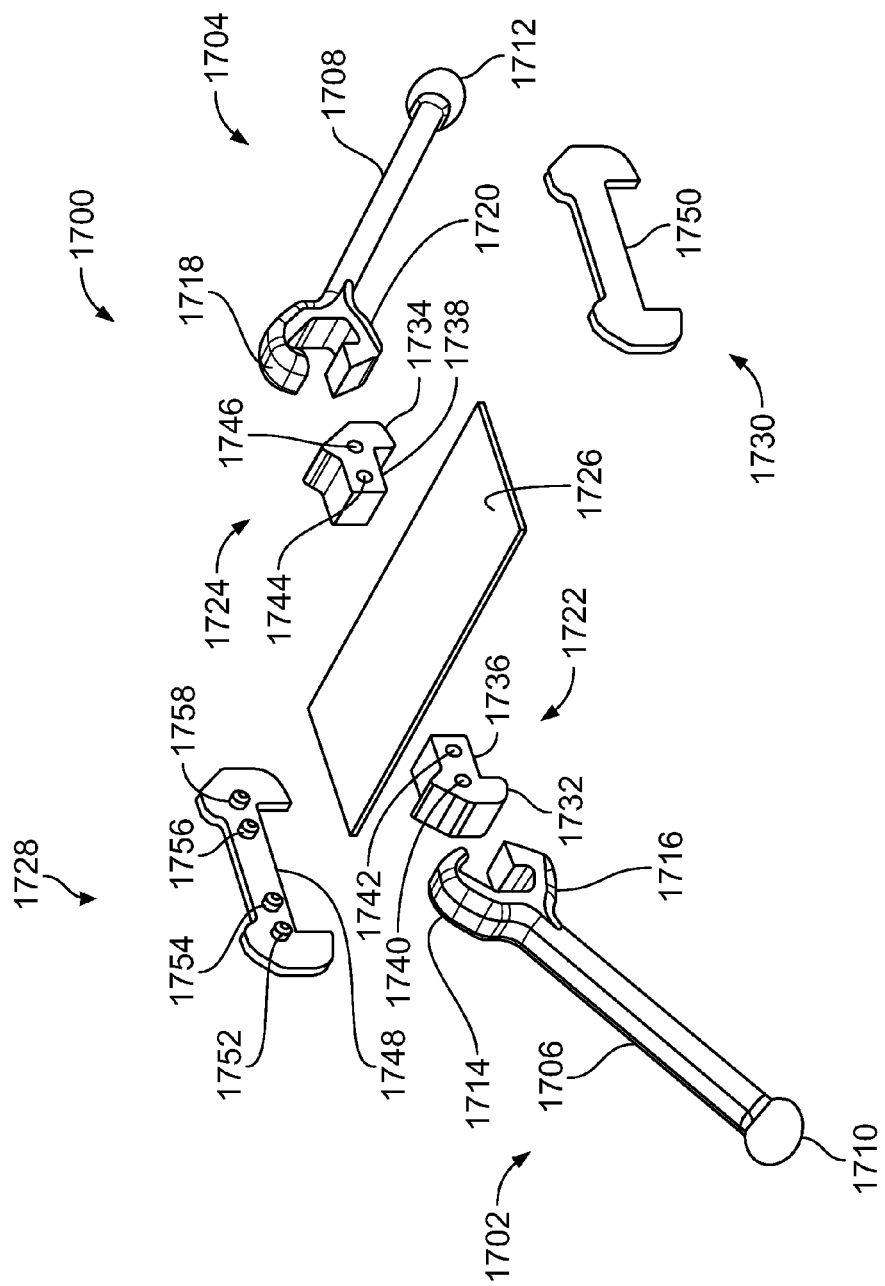
FIG. 17 is an exploded view of another example snap electrode constructed in accordance with the teachings of this disclosure.

FIG. 17 is an exploded view of another example electrode unit 1700 constructed in accordance with the teachings of this disclosure. In this example, the electrodes 1702, 1704 are snap electrodes. Each of the electrodes 1702, 1704 has a shaft 1706, 1708 and a contact ball 1710, 1712, respectively. The first electrode 1702 has a top hook member 1714 and a bottom hook member 1716. Likewise, the second electrode 1704 has a top hook member 1718 and a bottom hook member 1720. The example snap electrode unit 1700 of the illustrated example further includes a first connector 1722, a second connector 1724, a flex board 1726, a back plate 1728 and a front plate 1730. The first and second connectors 1722, 1724 each include a vertical portion 1732, 1734, respectively, and a horizontal portion 1736, 1738, respectively. Each of the first and second connectors 1722, 1724 further include two apertures 1740, 1742, 1744, 1746, respectively. The vertical portions 1732, 1734 are sized to fit within respective ones of the top and bottom hook member, 1714, 1716, 1718, 1720. The back plate 1728 includes a channel 1748 configured to receive the flex board 1726. The front plate 1730 likewise has a channel 1750 to receive the flex board 1726. The back plate also includes four pegs, 1752-1758. Two of the pegs 1752, 1754 are dimensioned to engage the apertures 1740, 1742 on the first connector 1722. The other two pegs 1756, 1758 are dimensioned to engage the apertures 1744, 1746 on the second connector 1724. The front plate 1730 of the illustrated example is operatively coupled to the opposite side of the back plate 1728.

In operation, the snap electrode unit 1700 is pressed downward against a user's head. The downward force causes the shafts 1706, 1708 to pivot upwards. The top hook members 1714, 1718 rotate inward onto the horizontal portions 1736, 1738, respectively, and, thus, against the flex board 1726. The flex board 1726 provides a reflective force so the electrodes 1702, 1704 keep a consistent force against the scalp of a user. The flex board 1726 also serves as the PCB to propagate any signals gathered from the electrodes 1702, 1704 to a processor and/or other analysis unit as disclosed herein.

Figure 18:
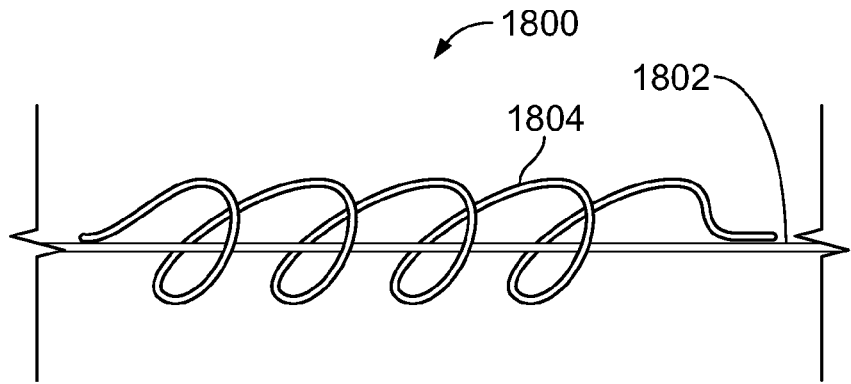
FIG. 18 is a perspective view of another example electrode constructed in accordance with the teachings of this disclosure.

FIG. 18 illustrates another example electrode 1800 constructed in accordance with the teachings of this disclosure. In the illustrated example, the electrode 1800 includes a wire band 1802 and a coil electrode 1804. In the example of FIG. 18, the coil electrode 1804 is a coil of wire wrapped around the wire band 1802 and is positioned to lie against the scalp of a user. The individual coils of the coil electrode 1804 will penetrate the hair of a user to make contact with the scalp. If the electrode 1804 rotates, the electrode 1804 will continually maintain contact with the scalp, and any signal being gathered will not be lost.

Figure 19A:
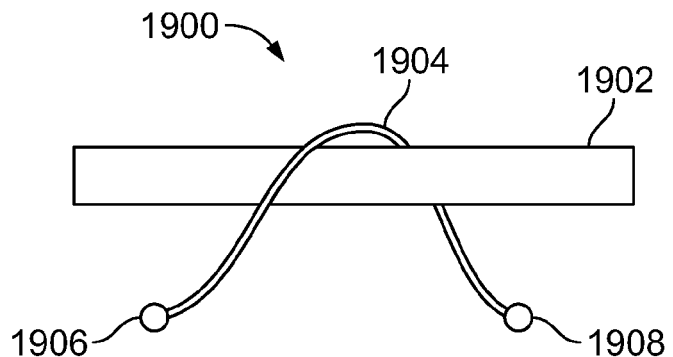
FIG. 19A is a perspective view of another example electrode constructed in accordance with the teachings of this disclosure.
Figure 19B:
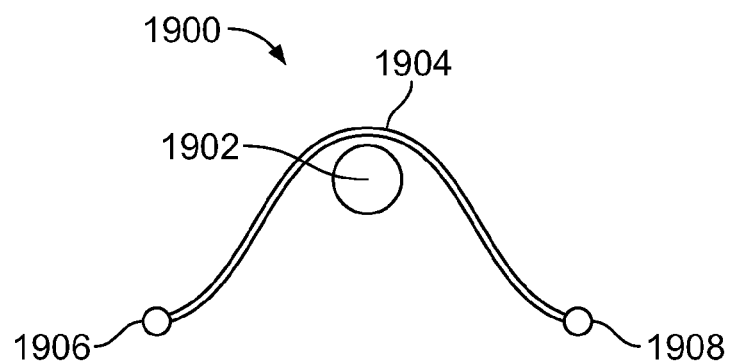
FIG. 19B is a cross-sectional view of the example electrode of FIG. 19A.

FIGS. 19A and 19B illustrate another example electrode 1900 constructed in accordance with the teachings of this disclosure. In the illustrated example, the electrode 1900 includes a wire band 1902 and a single curve electrode 1904. FIG. 19B is a cross-sectional view of the electrode 1900 of FIG. 19A. The single curve electrode 1904 of the illustrated example has two ball tips 1906, 1908 at the ends of the electrode 1904. The single curve electrode 1904 curves over the wire band 1902 so that both ends are pointed downward and both the ball tips 1906, 1908 may contact the scalp of a user. As the wire band 1902 is stretched or tightened, the electrode coupled thereto is also stretched, and the center portion of the electrode 1904 moves closer to the scalp to provide additional pressure to the ball tips 1906, 1908 against the scalp.

Figure 20:
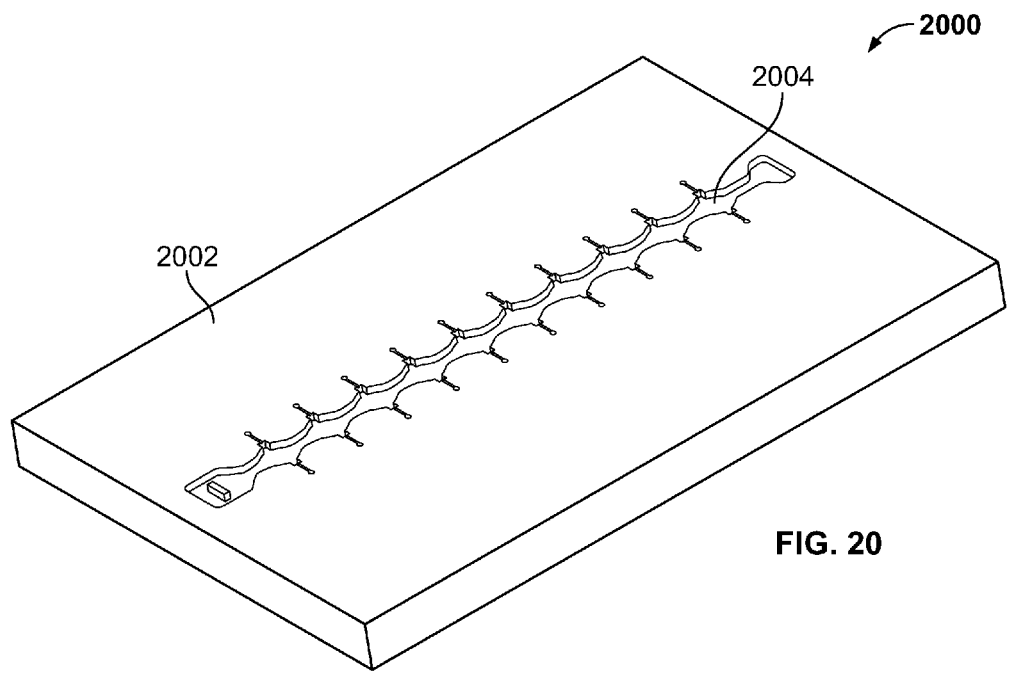
FIG. 20 is a perspective view of an example mold used for manufacturing an example spine.

FIG. 20 shows a mold 2000 that may be used for manufacturing a spine as shown and described in FIGS. 1-7. In the illustrated example, the mold 2000 comprises a mold body 2002 and a mold cavity 2004. The mold cavity 2004 defines the shape of a flat spine. In an example manufacturing procedure, the PCB and electrodes are placed within the mold first, and then liquid plastic or resin is injected into the cavity 2004 to form the spine body. After the molding processing the spine is remove and formed to curve the individual extensions downward.

Figure 21:
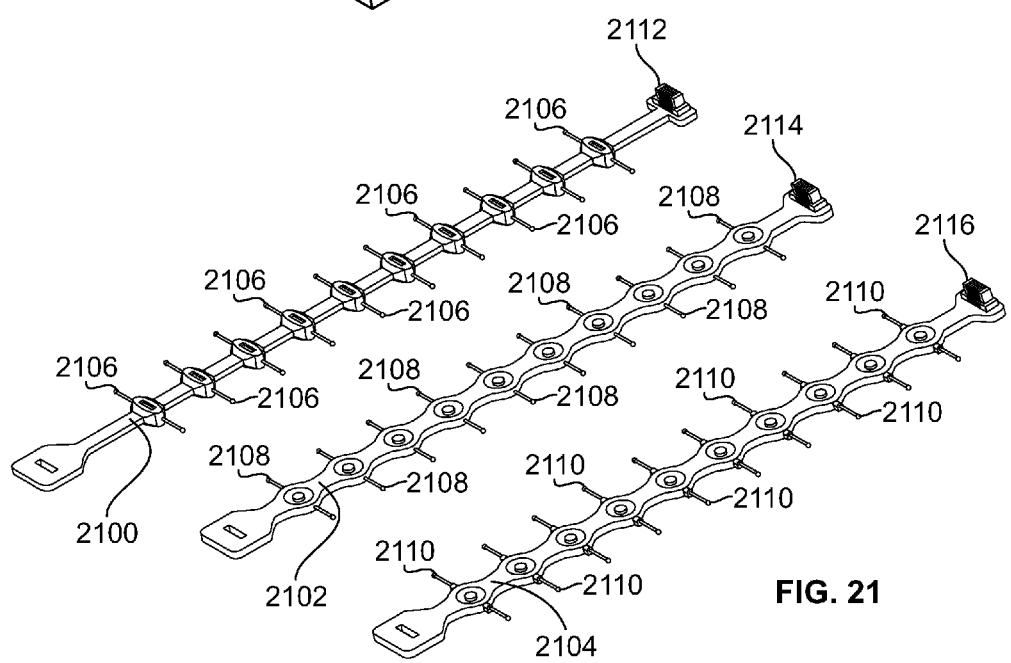
FIG. 21 is a perspective view of an example spine after manufacturing in the example mold of FIG. 20.
Figure 22C:
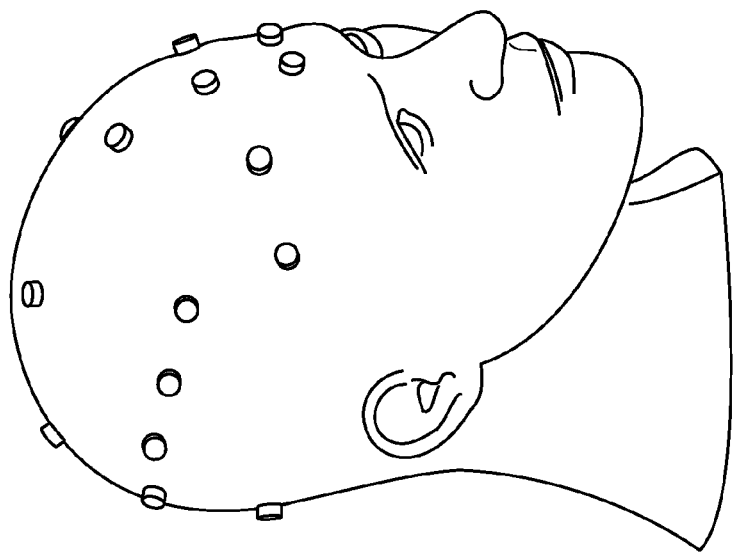
Figure 22B:
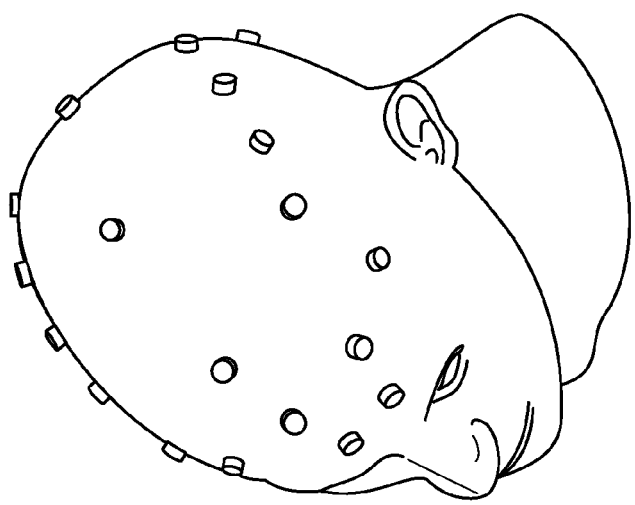
Figure 22A:
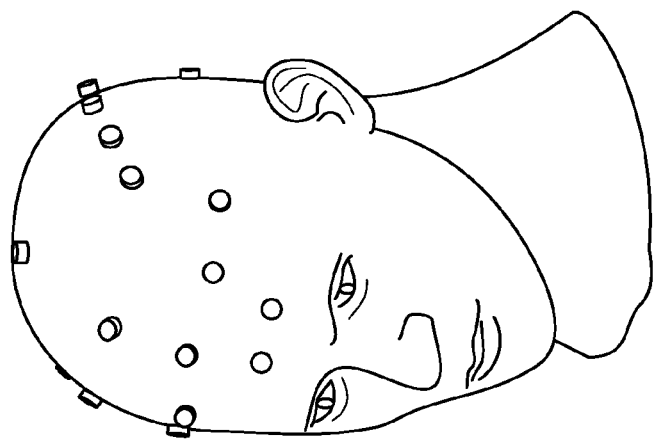
Figure 22F:
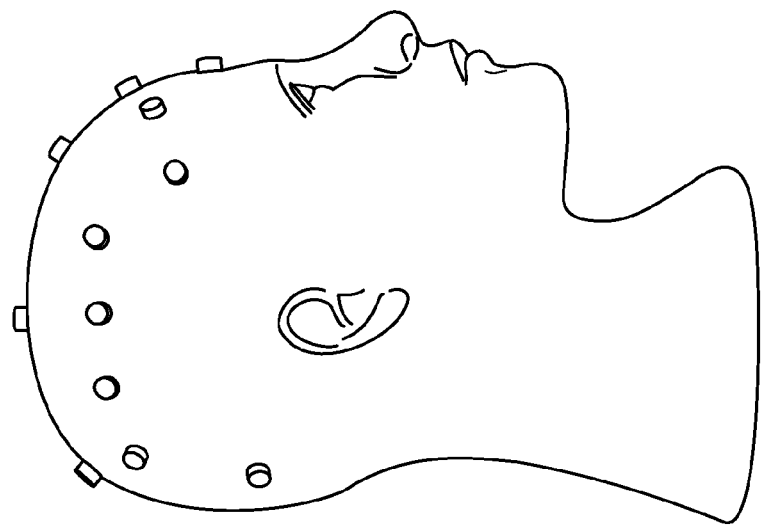
Figure 22E:
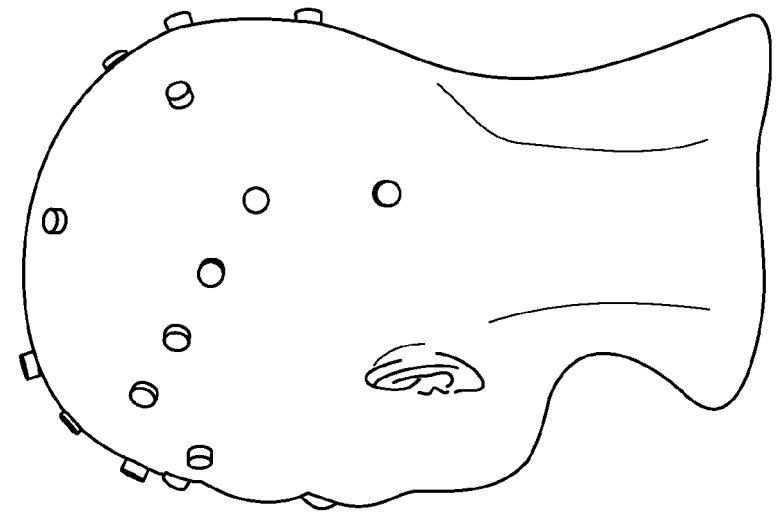
Figure 22D:
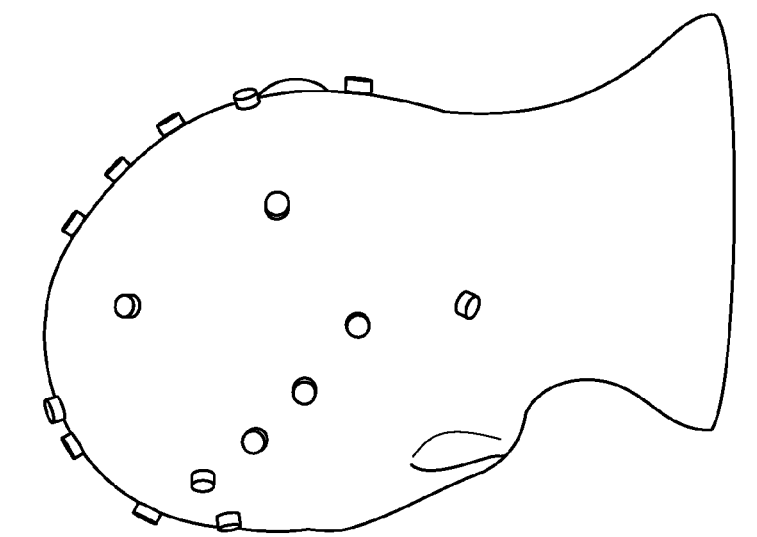
Figure 22I:
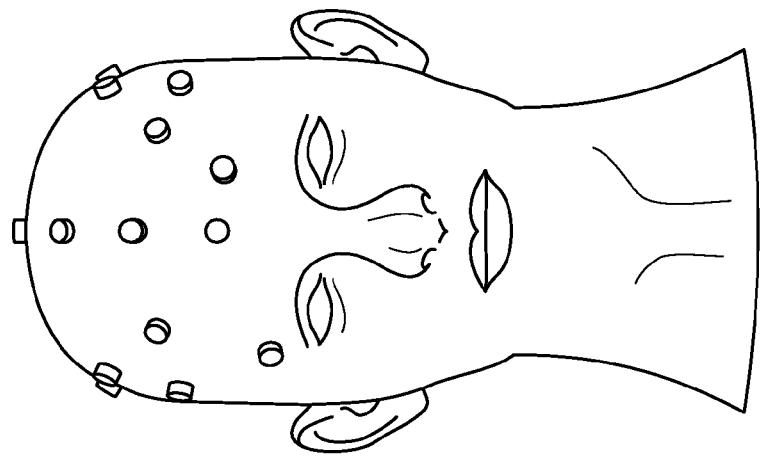
Figure 22H:
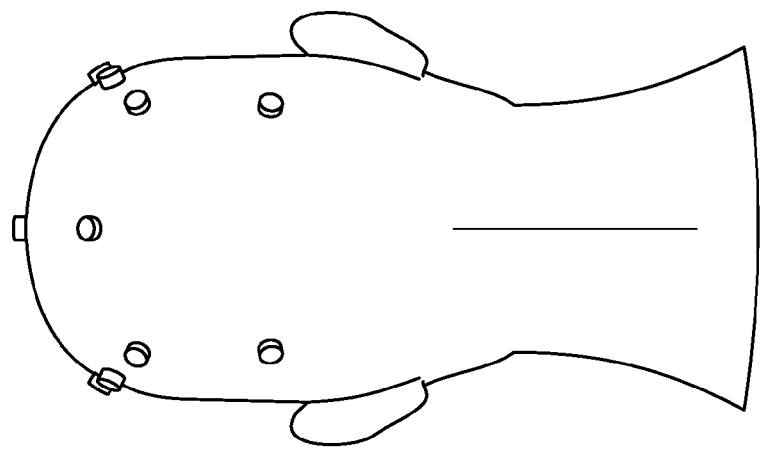
Figure 22G:
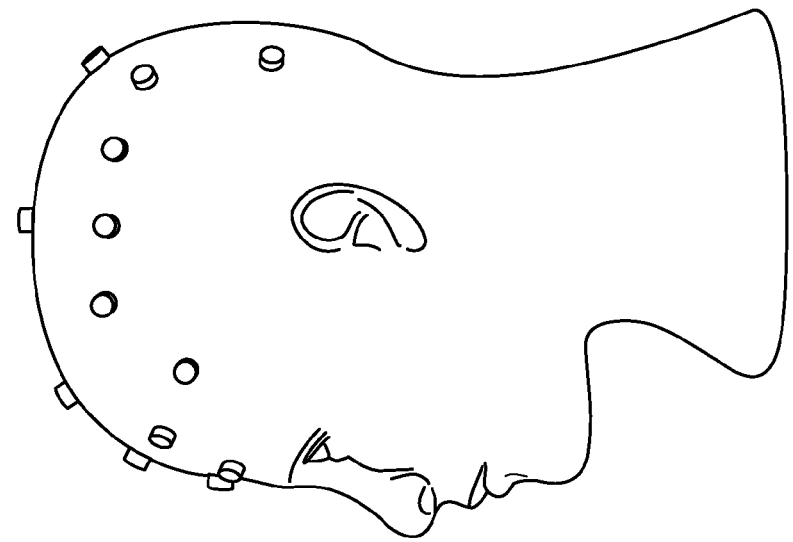

FIG. 21 shows multiple spines 2100, 2102, 2104 directly after molding in the process described in connection with FIG. 20 and before the spines are shaped. In the example of FIG. 21, the spines 2100, 2102, 2104 comprise a plurality of electrodes 2106, 2108, 2110 protruding from the spines 2100, 2102, 2104. The ball electrodes 2106, 2108, 2110 may be curved downward. In this example, the ends of each spine 2100, 2102, 2104 include a pin port 2112, 2114, 2116 for coupling the spine 2100, 2102, 2104 to a processing unit to a headset.

FIGS. 22A-22J are perspective views of a user's head identifying optimum areas for electrode contact. As shown in these figures, there are multiple electrode sites including, for example, twenty sites related to the International 10-20 system. These sites provide coverage of all the lobes of the brain including frontal, parietal, occipital and temporal. These sites are the accepted EEG electrode sites for a clinically valid EEG. The sites shown in FIGS. 22A-22J are selected to give broad coverage and avoid sites with excessive muscle activity. In an example headset with eighty channels, the twenty sites of the International 10-20 system are covered as are additional sites over muscle. For example the eighty channel system provides predominant coverage to non-muscle contaminated sites as well as covering muscle sites included in the standard clinical EEG system.

FIG. 22J illustrates an example headset with five bands 2202-2210 positioned on the head of a user for reading. The individual bands 2202-2210 are adjustable and may be placed along specific paths to optimize electrode placement. The example scheme of FIG. 22J bisects the head into a left section and a right section by forming a line between the nasion (between the eyes) to the inion (back of the head). A second line bisects the head along a line from the left ear canal to the right ear canal. Each of these lines is further partitioned at intervals of 10% and 20% of its distance. In the illustrated example, a first elongated band 2202 is located above a nasion of the subject at about ten percent of a distance between the nasion and an inion of the subject measured over a center of a head of the subject. A second elongated band 2204 is located above the nasion at about thirty percent of the distance to the inion. A third elongated band 2206 is located at about halfway between the nasion and the inion. A fourth elongated band 2208 is located past the halfway point, e.g., closer to the inion than the nasion but more than thirty percent of the distance away from the inion. A fifth elongated band 2210 is located above the inion at about thirty percent of the distance. This arrangement may optimize coverage of the entire head. In other examples, additional bands are included in positions between the five illustrated bands. Still further, in other examples, the bands 2202-2210 are positioned at any other desired degree of rotation depending on the desired readings and/or the quality of electrical contact between the electrodes and the scalp.

Figure 23:
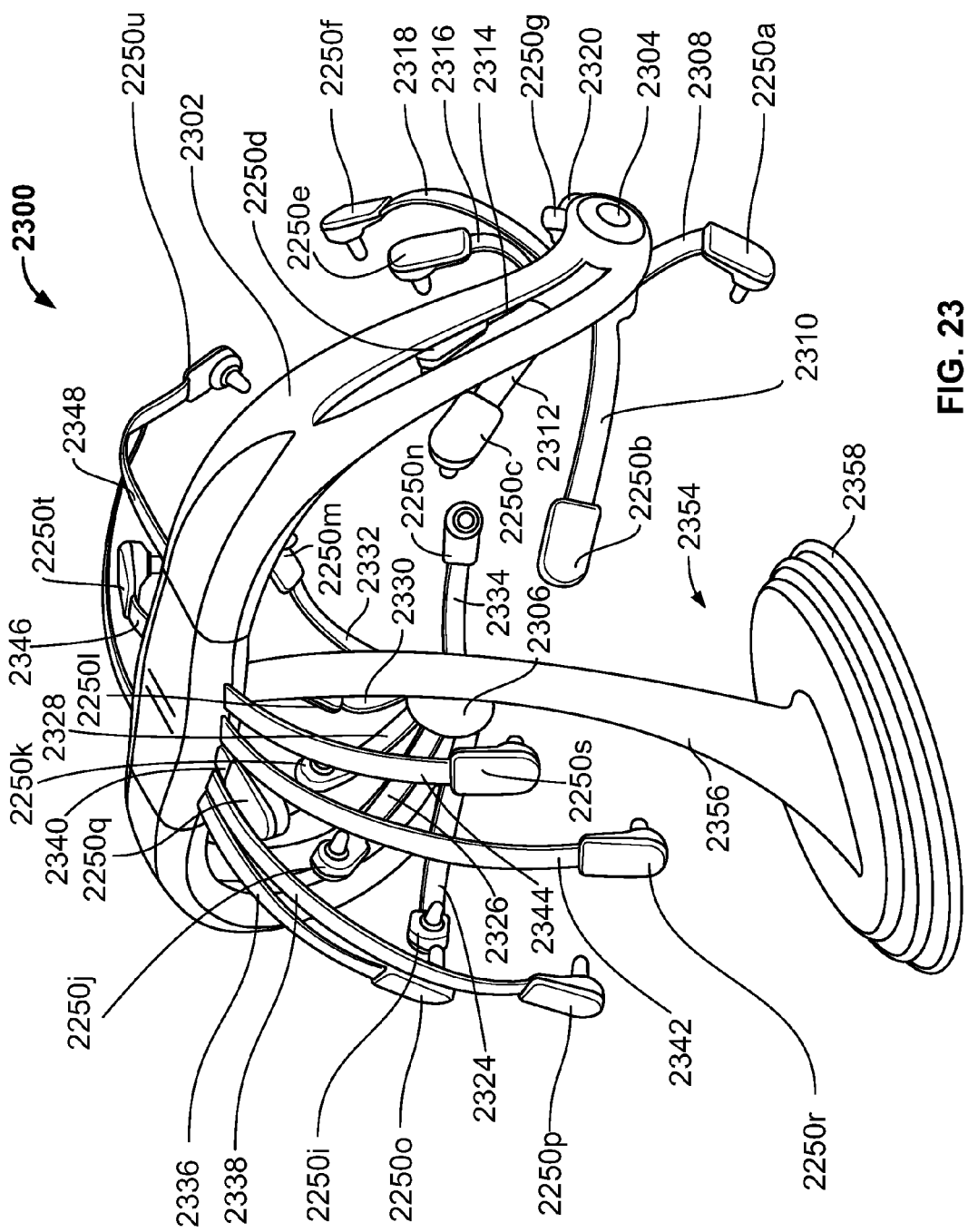
FIG. 23 is a perspective view of another example headset constructed in accordance with the teachings of this disclosure and having a plurality of bands with electrode tips.

FIG. 23 illustrates an alternative example headset 2300 constructed in accordance with the teachings of this disclosure for measuring electrical activity at the scalp. The headset 2300 of this example comprises a main headband 2302, which curves over the top of the head of a user. Multiple support bands having individual electrodes extend from the headband 2302 in multiple directions for positioning electrodes over multiple locations on a user's head. The headset 2300 includes a left hub 2304 and a right hub 2306, both of which are rotatably and removably coupled to the ends of the headband 2302. In the illustrated example, the left hub 2304 includes seven support bands 2308-2320. The right hub 2306 of the illustrated example also includes seven support bands 2322-2334. However, in other examples, different number(s) of support bands are used to increase, decrease and/or otherwise adjust the number and/or location of electrode placement. In this example, each of the support bands 2308-2334 has a set length and two ends which are fixedly and flexibly coupled to the left and right hubs 2304, 2306, respectively. In some examples, one or more of the lengths of the support bands 2308-2334 are adjustable. The headband 2302 further includes front support bands 2336-2344 and rear bands 2346-2348. In this example, each of the supports bands 2336-2348 has a set length and is fixedly and flexibly attached on one end to the headband 2302. Also, in some examples, one or more of the lengths of the support bands 2336-2344 are adjustable. The distal ends of all the support bands 2308-2348 are operatively coupled to a respective electrode housing 2250a-2250u. Each housing 2250a-2250u houses an individual electrode 2352a-2352u, respectively. In some examples, one or more of the electrode housings 2250a-2250u support a plurality of electrodes. In the illustrated example, different ones of the support bands 2308-2348 have different lengths to position the respective electrodes 2352a-2352u over different locations on the scalp. The locations may be selected to optimize detection of electrical activity in the brain. The support bands 2308-2348 are curved slightly inward to apply sufficient force on the head of a user to cause the respective electrode to press slightly onto the scalp to reduce noise and increase the signal-to-noise ratio to enhance signal quality. Further, the support bands 2308-2348 in the illustrated example include a flexible plastic to enable each support band 2308-2348 to flex when placed over the head of a user and accordingly adjusts to different head sizes and applies a constant and/or sufficient force to the scalp for reading the electrical signals of the brain. In the example shown in FIG. 23, the headset 2300 has twenty-one support bands and twenty-one electrodes. However, in other examples the headset includes more or fewer support bands and/or may include more than one electrode per support band.

Further, as shown in FIG. 23, the headset 2300 is couplable to a base 2354 for storing the headset 2300 when not in use, for charging the headset 2300 and/or for data transfer as disclosed in greater detail below. The base 2354 includes a generally vertically extending support shaft 2356 to hold the headset 2300 above a support surface such as a table, desk or shelf. The base 2354 also includes a base plate 2358 to support the base 2354 in an upright position. In some examples, the base 2354 transfers data via a wired connection to a data analyzer. In other examples, the base 2354 wirelessly transfers data.

Figure 24:
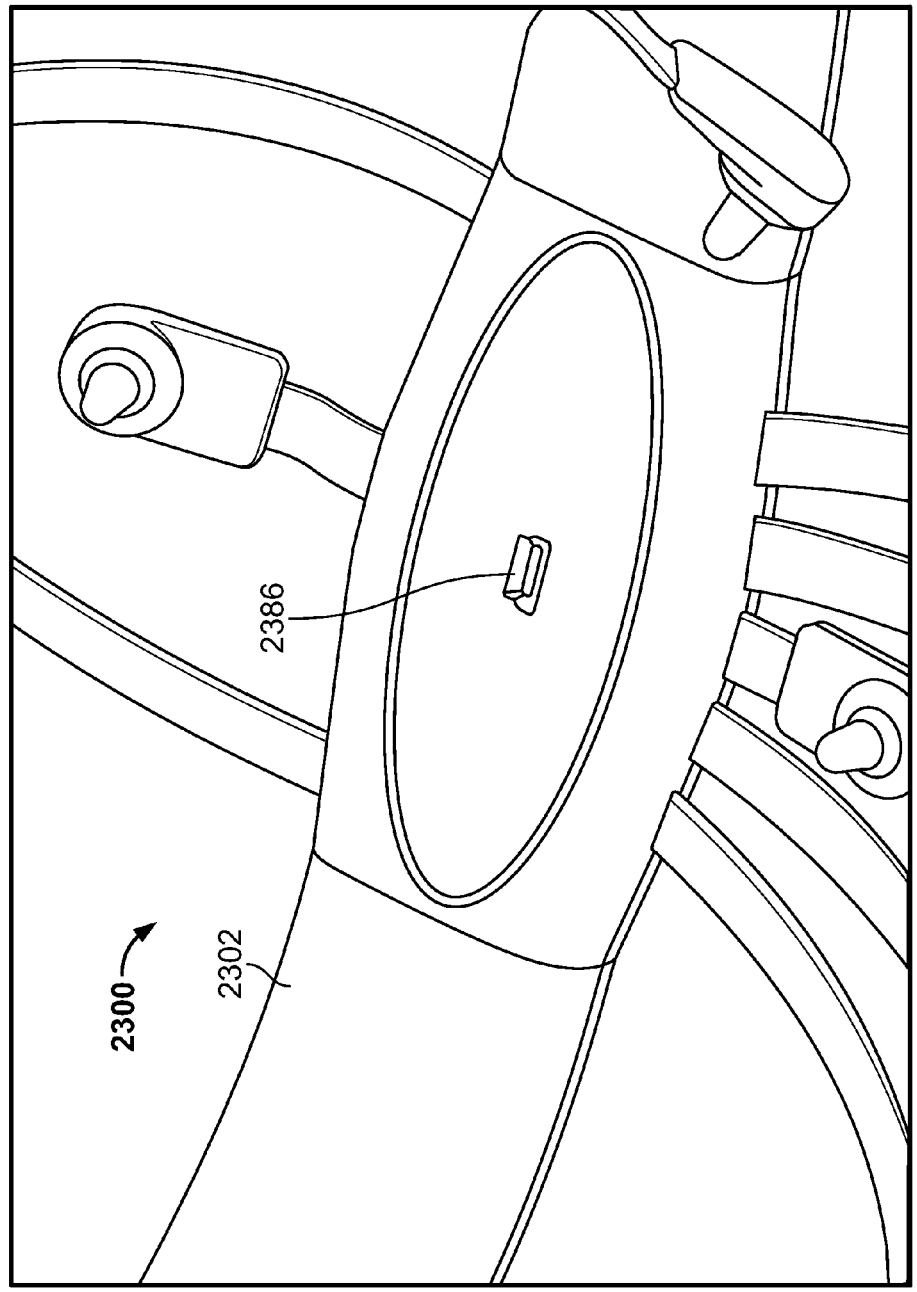
FIG. 24 is a bottom view of the example headset of FIG. 23 and a USB connection port.
Figure 25:
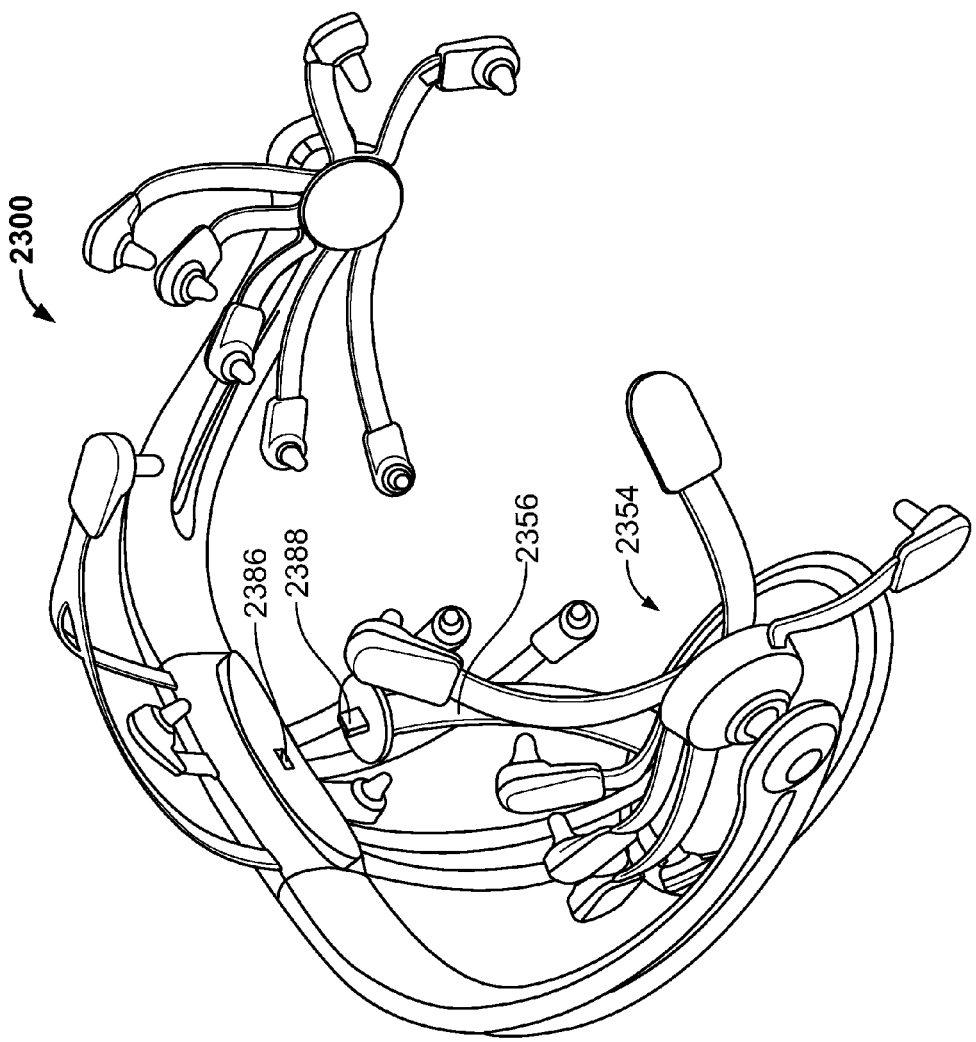
FIG. 25 is a perspective view of the example headset of FIG. 23 on a USB base stand.

FIG. 24 is a bottom view of the example headset 2300 of FIG. 23. The headband 2302 has a micro-USB port 2386 on the bottom for battery charging and data transfer. The headset 2300 includes a battery within the central headband 2302 and/or within a housing such as, for example, a housing located near the sides of the head (see e.g., the housings 3010, 3012 disclosed below in connection with FIG. 30, which may be incorporated into the example headset 2300 of FIG. 23). As seen in FIG. 25, the base shaft 2356 of the base 2354 includes a male micro-USB connector 2388, which may be inserted into micro-USB port 2386 for charging the headset 2300 and/or transferring data from a headset-based processor to a computer or a database for further processing. In other examples, any other suitable electrical and/or communication coupling may be used including, for example, other types of physical ports and/or a wireless coupling.

Figure 26:
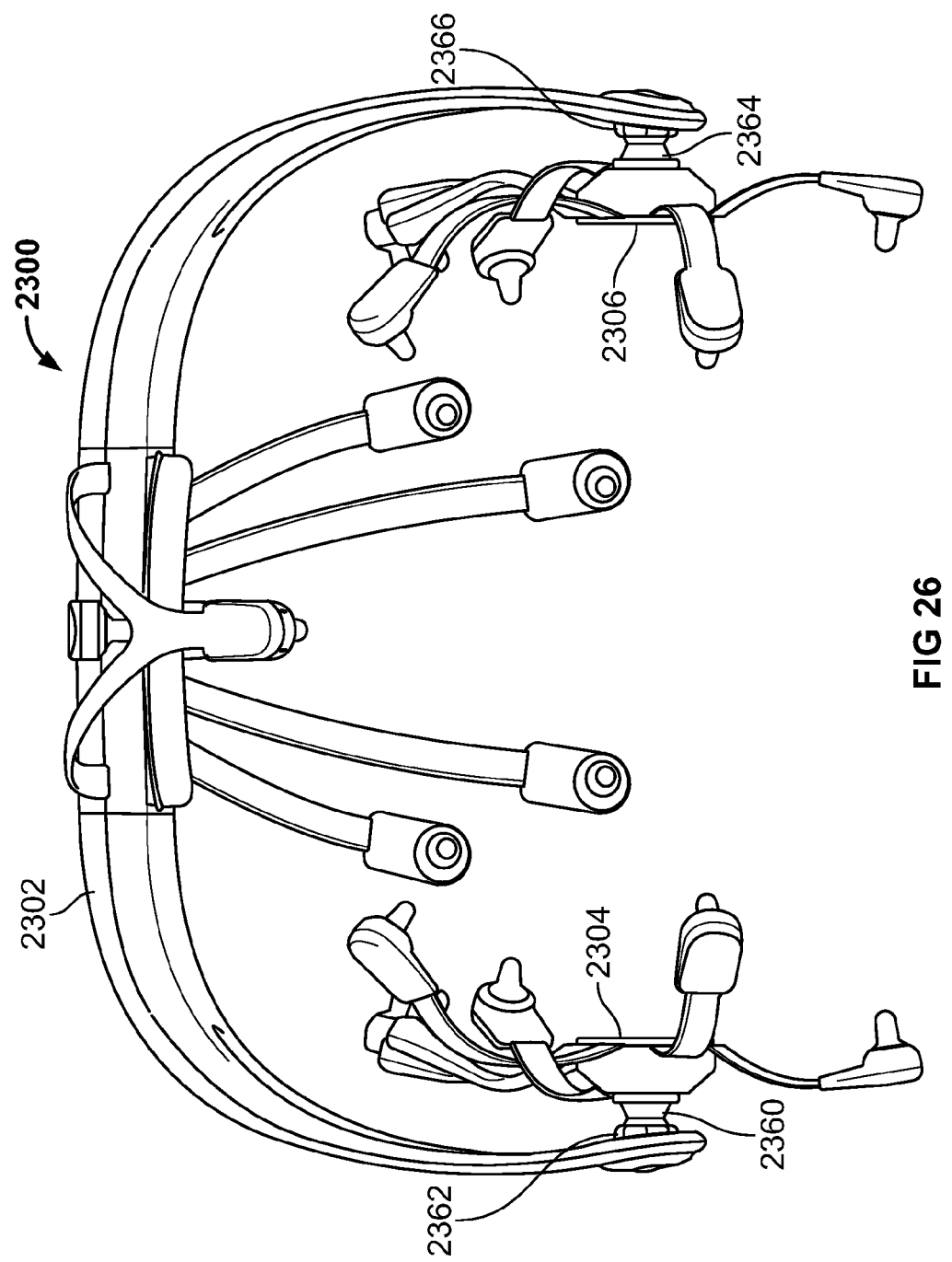
FIG. 26 is a back side view of the example headset of FIG. 23.
Figure 27:
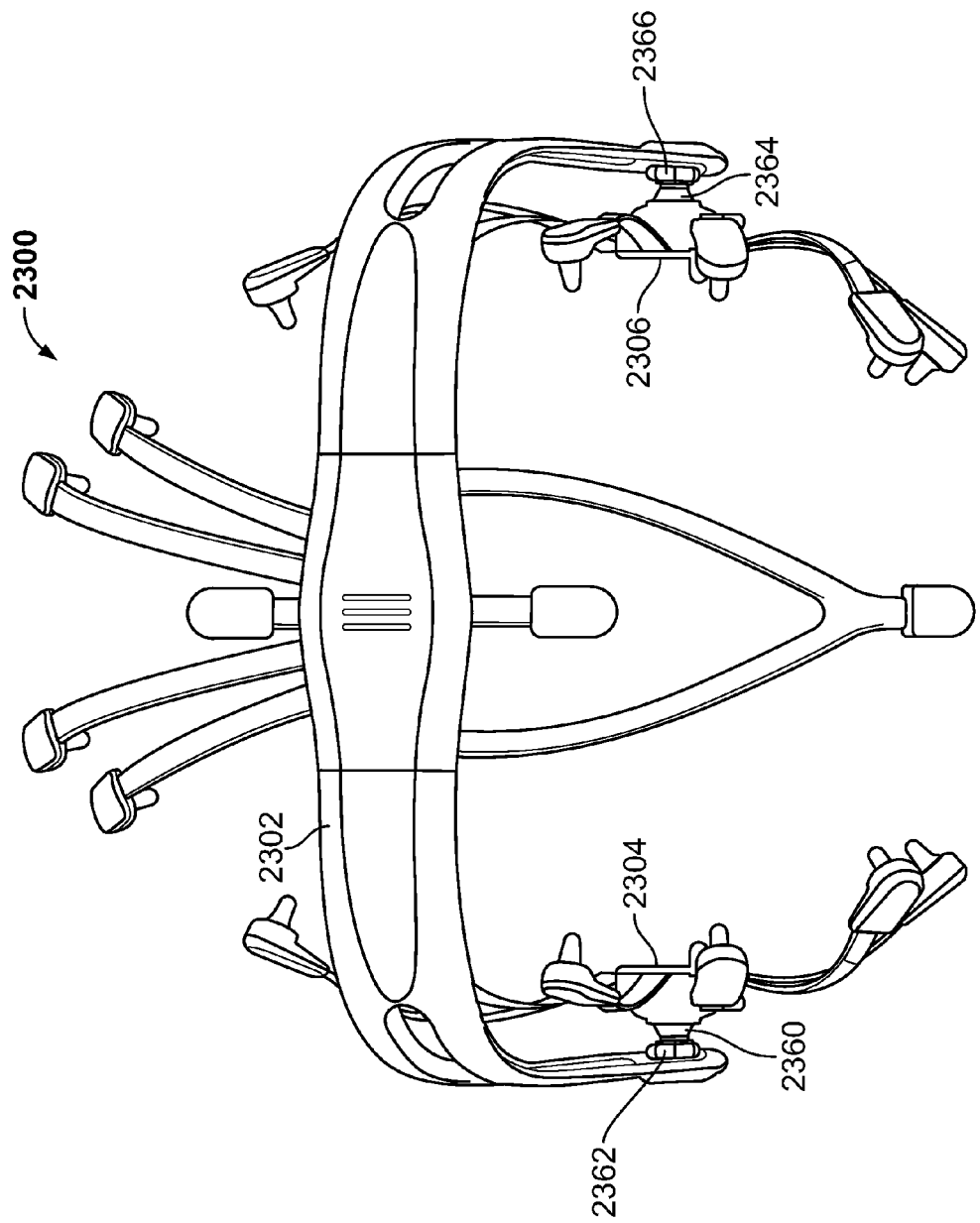
FIG. 27 is a top side view of the example headset of FIG. 23.
Figure 28:
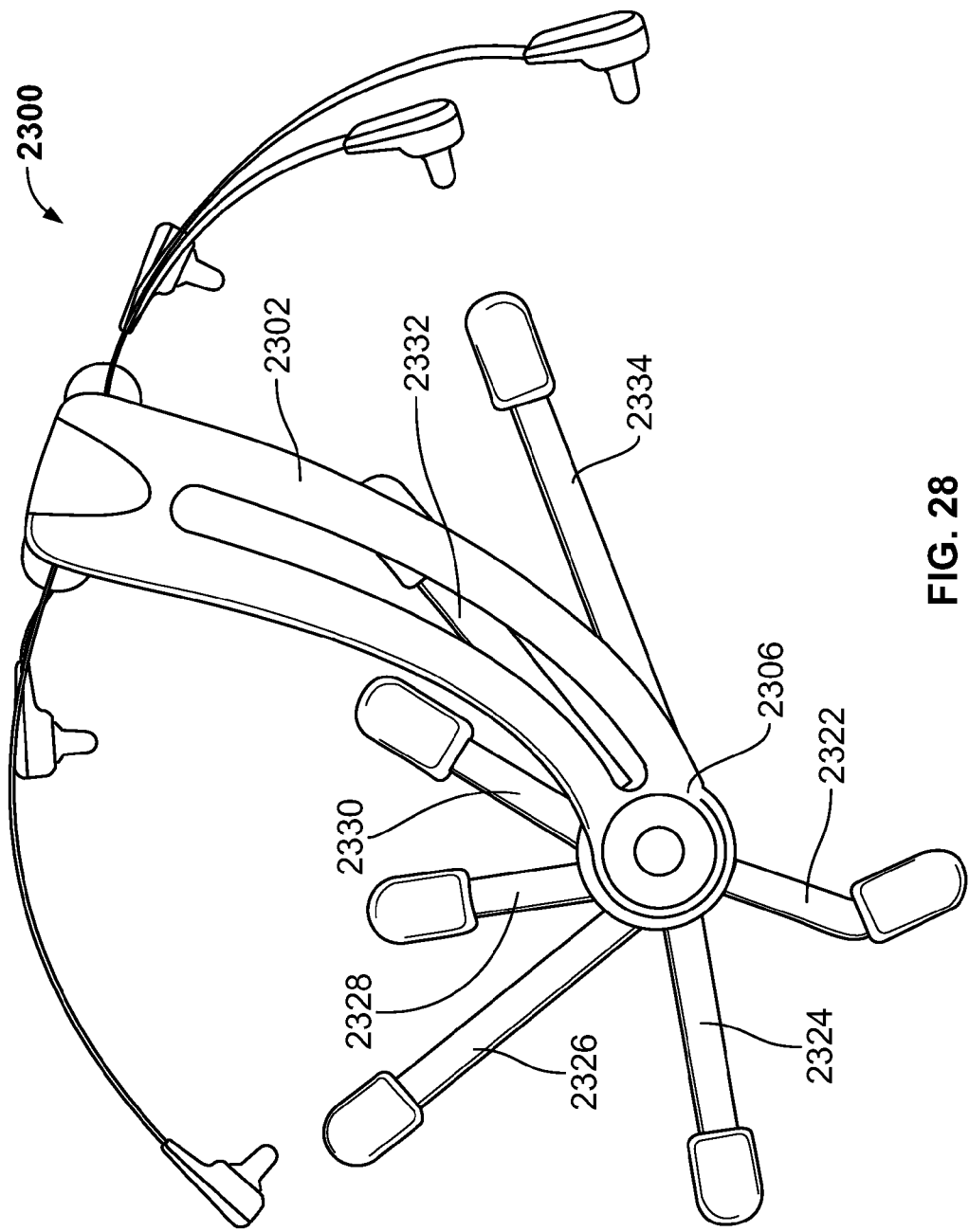
FIG. 28 is a right side view of the example headset of FIG. 23.

FIGS. 26-29 are different views of the example headset 2300. As seen in FIGS. 26 and 27, the left and right hubs 2304, 2306 are rotatably and pivotally coupled to the ends of the headband 2302. The left hub 2304 has an adjustment ball 2360 that fits within a left socket 2362 on the inside of the headband 2302. The adjustment ball 2360 and left socket 2362 (i.e., ball and socket joint) allow the hub 2304 to rotate and pivot in any desired direction to position the support bands 2308-2320 over desired locations on the left side of a user's head. The right hub 2306 also has an adjustment ball 2364 that is designed to fit within a right socket 2366 on the headband 2302. Thus, the right hub 2306 also is coupled to the headband via a ball and socket joint to enable the hub 2304 to rotate and pivot in any desired position. FIG. 28 shows the headband 2302 slightly curved to the back such that the headset 2300 is supported at a crown of the head while the left and right hubs 2304, 2306 are positioned near the left and right ear, respectively.

Figure 29:
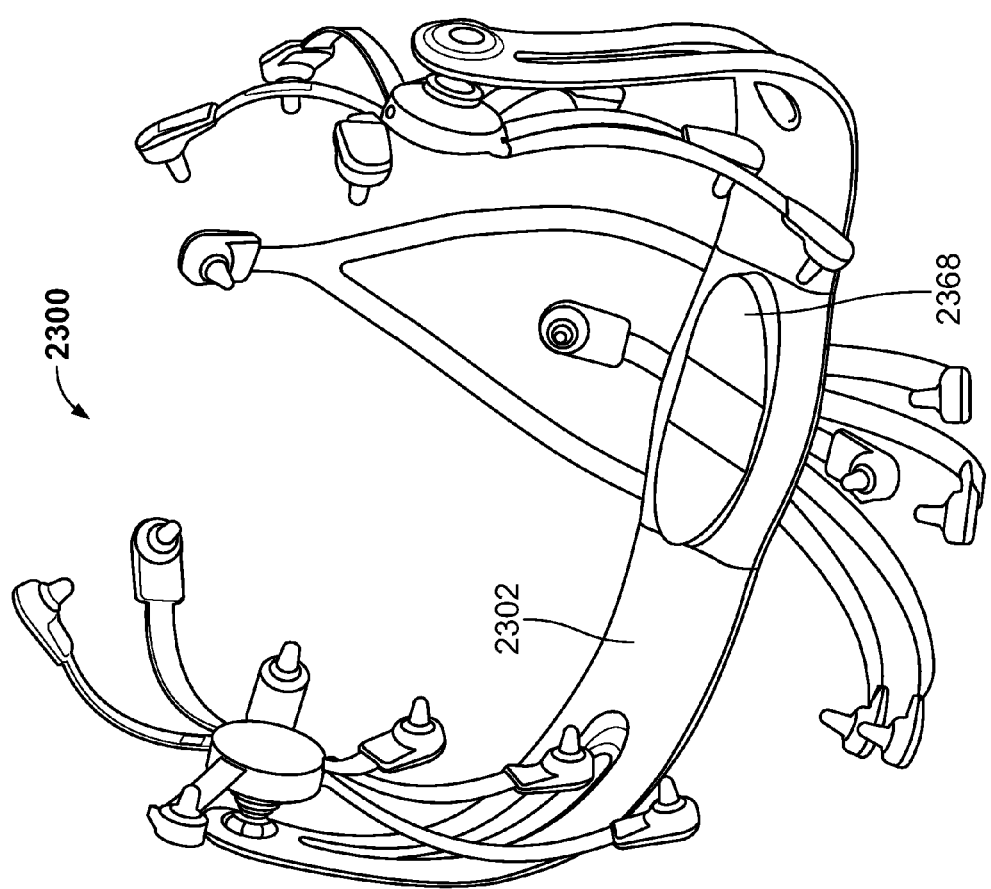
FIG. 29 is a bottom perspective view of the example headset of FIG. 23.

FIG. 29 is a bottom view of the headset 2300 and shows that the headset 2300 includes a pad 2368 that provides comfort to the user and also may be used to provide stability to the headset 2300 so that the headset 2300 maintains its position as the user moves his or her head. Increasing the stability of the headset 2300 also decreases any noise that may be generated by friction caused by movement of the electrodes along the scalp of the user. In addition, the pad 2368 may double as a housing that encases electrical components such as, for example, a processor, which may, for example, comprises hardware, firmware and/or software for processing the signals from the electrodes, converting the electroencephalographic data from analog data to digital data, amplifying the electroencephalographic data, removing noise from the data, analyzing the data, and/or transmitting the data to a computer or other network. The headset 2300 comprises a printable circuit board 2370 that is disposed within the headband 2302 and the support bands 2308-2344 to communicatively couple the electrodes 2352a-2352u to the processor for processing. Also, in some examples, the housing 2368 may encase a power supply such as, for example, one or more batteries.

Figure 30:
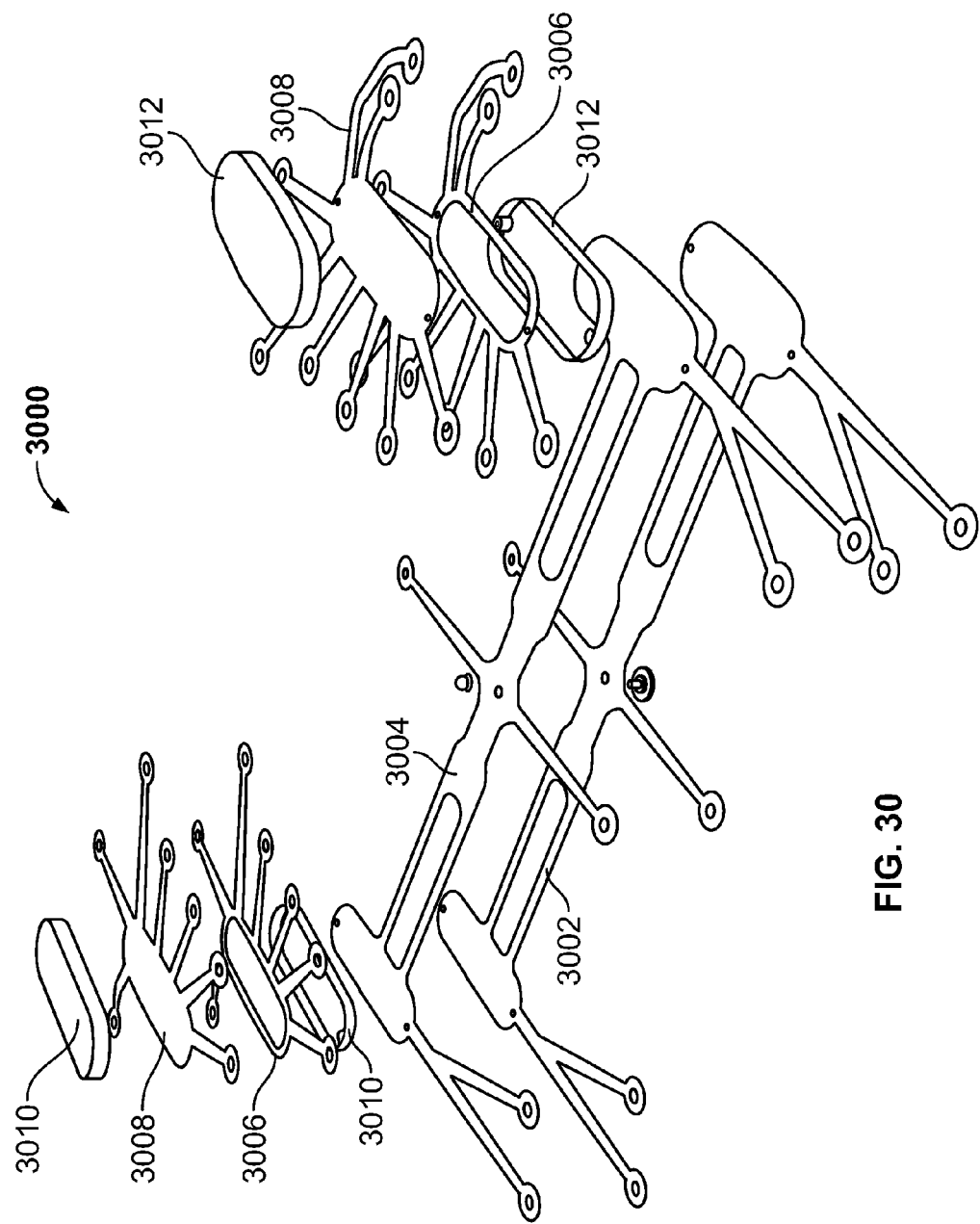
FIG. 30 illustrates an exploded view of example layers of an example headset.

FIG. 30 illustrates an exploded view of example layers for an example headset 3000. Though an alternative shape is shown in FIG. 30, the layering concepts shown in FIG. 30 may be used for any suitable headset structure including, for example, the headset 100 of FIG. 1, the headset 1500 of FIG. 15, a headset created in the mold 2000 of FIG. 20, the headset 2300 of FIG. 23 and/or other suitable headset. The first layer 3002 comprises a plastic and/or metal housing layer. The first layer 3002 provides tension and shape to the headset 3000 as well as the flexibility needed to adjust the headset and apply sufficient pressure at each electrode to optimize signal gathering. The dimensions (e.g., width) of each arm in the layer is specifically designed for a particular tension (e.g., to optimize performance). The second layer 3004 is the flexible circuit board that is used to transmit data gathered at each electrode to the electronics/processor. The headset 3000 includes a third layer 3006 and fourth layer 3008 at each end. The third layer 3006 corresponds to the material of the first layer 3002 and the fourth layer 3008 corresponds to the material of the second layer 3004. The first layer 3002 and the third layer 3006 provide shielding to the signals as the signals propagate along the second layer 3004 and the fourth layer 3008. Also, the material used may be selected to enhance shielding for the flexible PCB and electromagnetic interference shielding for the example systems. Also, the PCBs of the second layer 3004 and fourth layer 3008 are flexible and thin and include thin wiring that has low impedance and low capacitance, which reduces loss during signal propagation.

Figure 31:
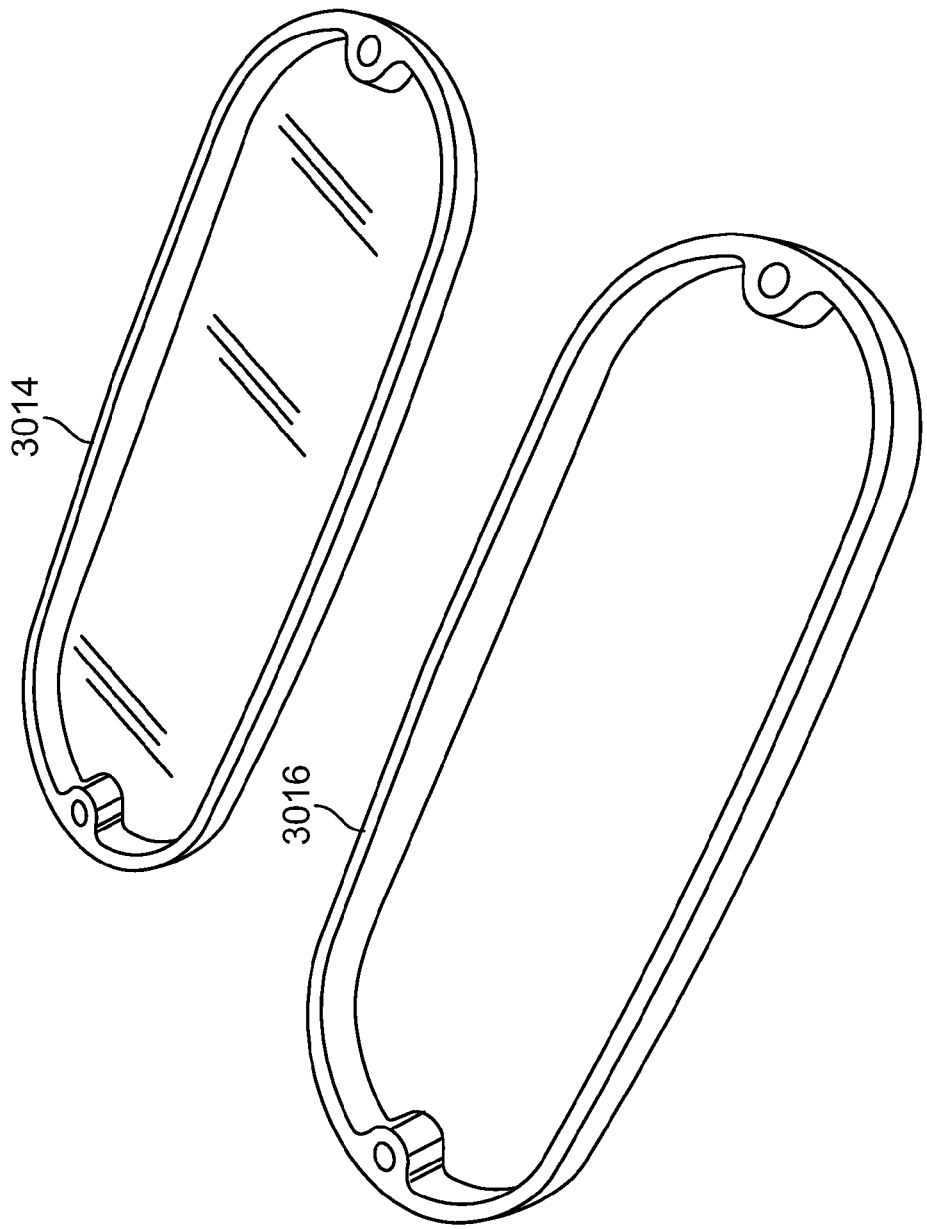
FIG. 31 is an exploded view of the example circuit housing of FIG. 30.

The headset 3000 also includes a first housing 3010 and a second housing 3012. An example of the first and second housing is shown in greater detail in FIG. 31. Each housing includes a cover 3014 and a support ring 3016. The electronic components and processor are supported in one of more of the housings 3010, 3012. Additionally or alternatively, in some examples, an adjustment mechanism such as, for example, the adjustment mechanism of FIG. 9 is supported by one or more the housings. Though an oval shape is shown in FIGS. 30 and 31, any suitable shape may be used for the housings.

Figure 32A:
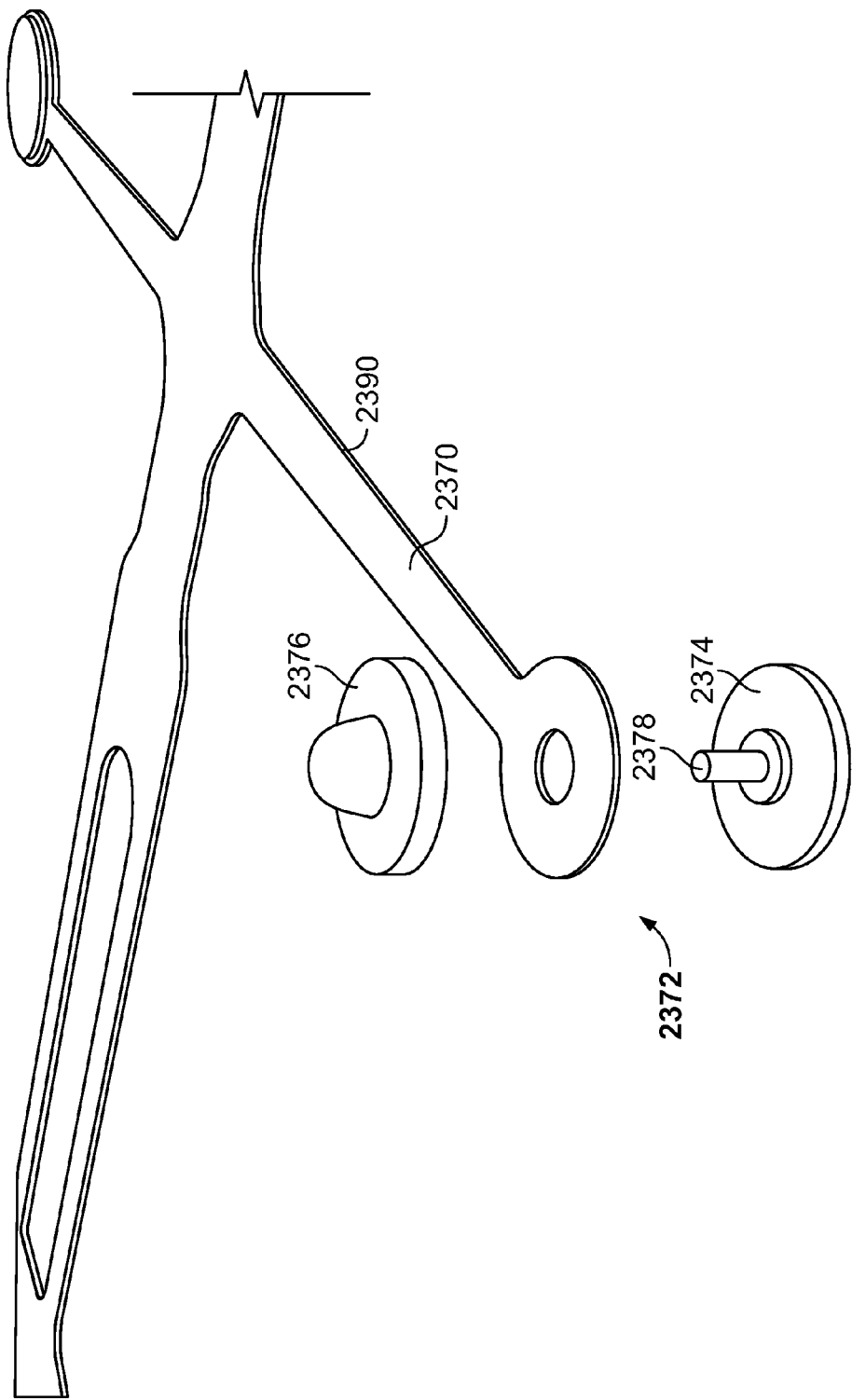
Figure 32C:
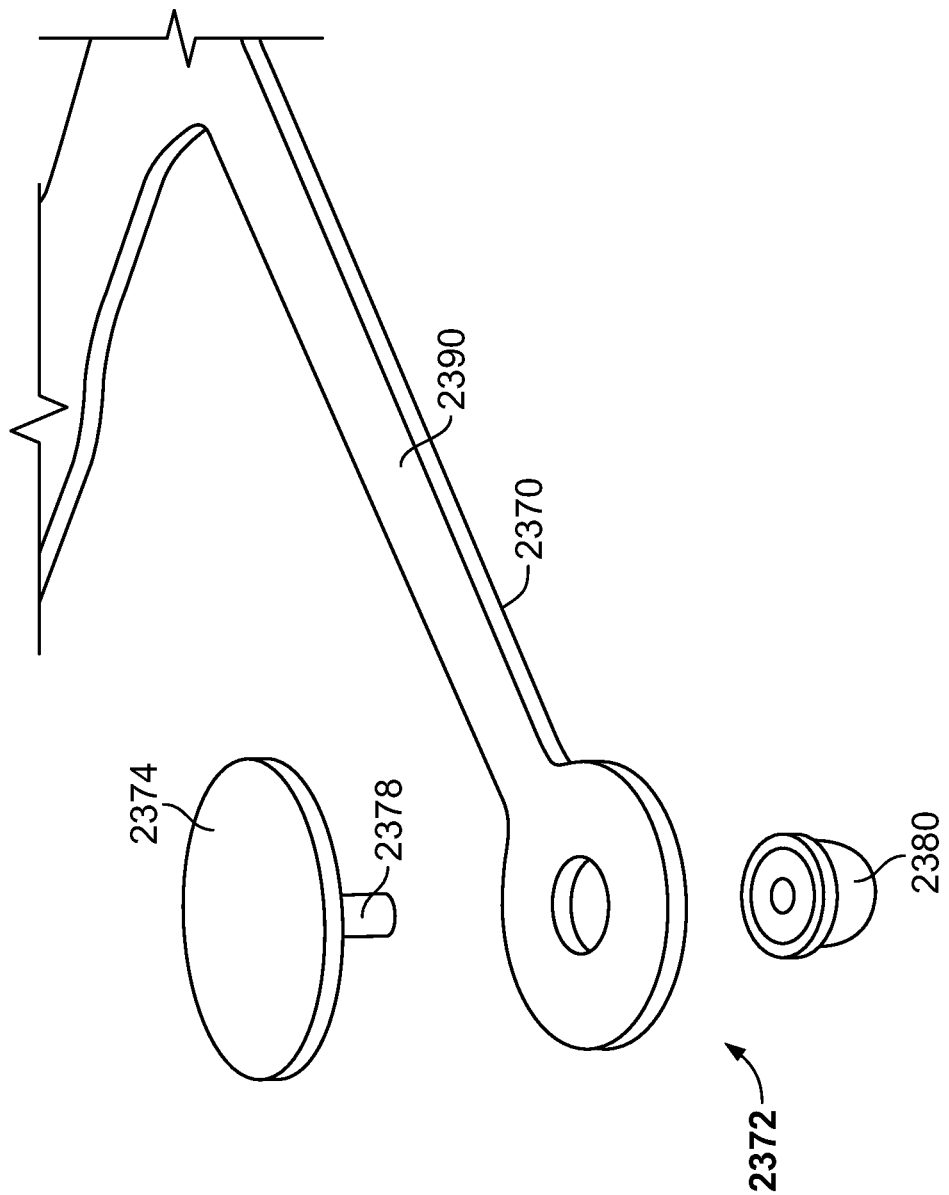
Figure 32D:
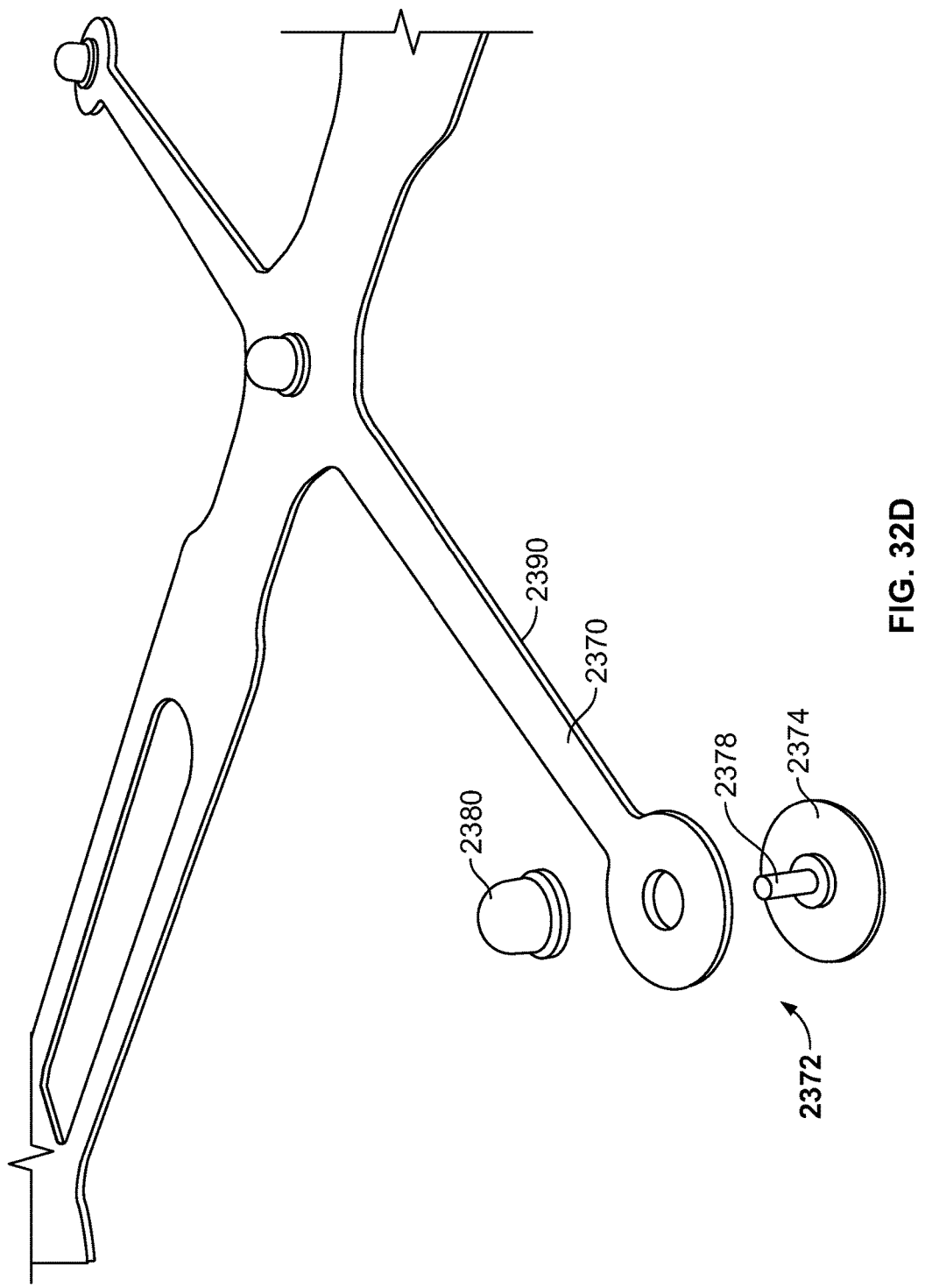

FIGS. 32A and 32B illustrate top and bottom perspective views of an example snap electrode unit 2372. The snap electrode unit 2372 comprises back plate 2374 and an electrode layer 2376. The electrode layer 2376 may comprise a silver coated electrode or an electrode coated with or made from any suitable conductor. The back plate 2374 has a shaft 2378, which extends through the PCB 2370 and support band 2390 into the back of the electrode 2376 to couple the electrode 2376 to the PCB 2370 and the support band 2390. The electrode may be readily assembled with the back plate or disassembled from the back plate to facilitate replacement of the electrodes. FIGS. 32C and 32D illustrate a snap electrode unit 2372 with an alternative contact electrode 2380.

Figure 33:
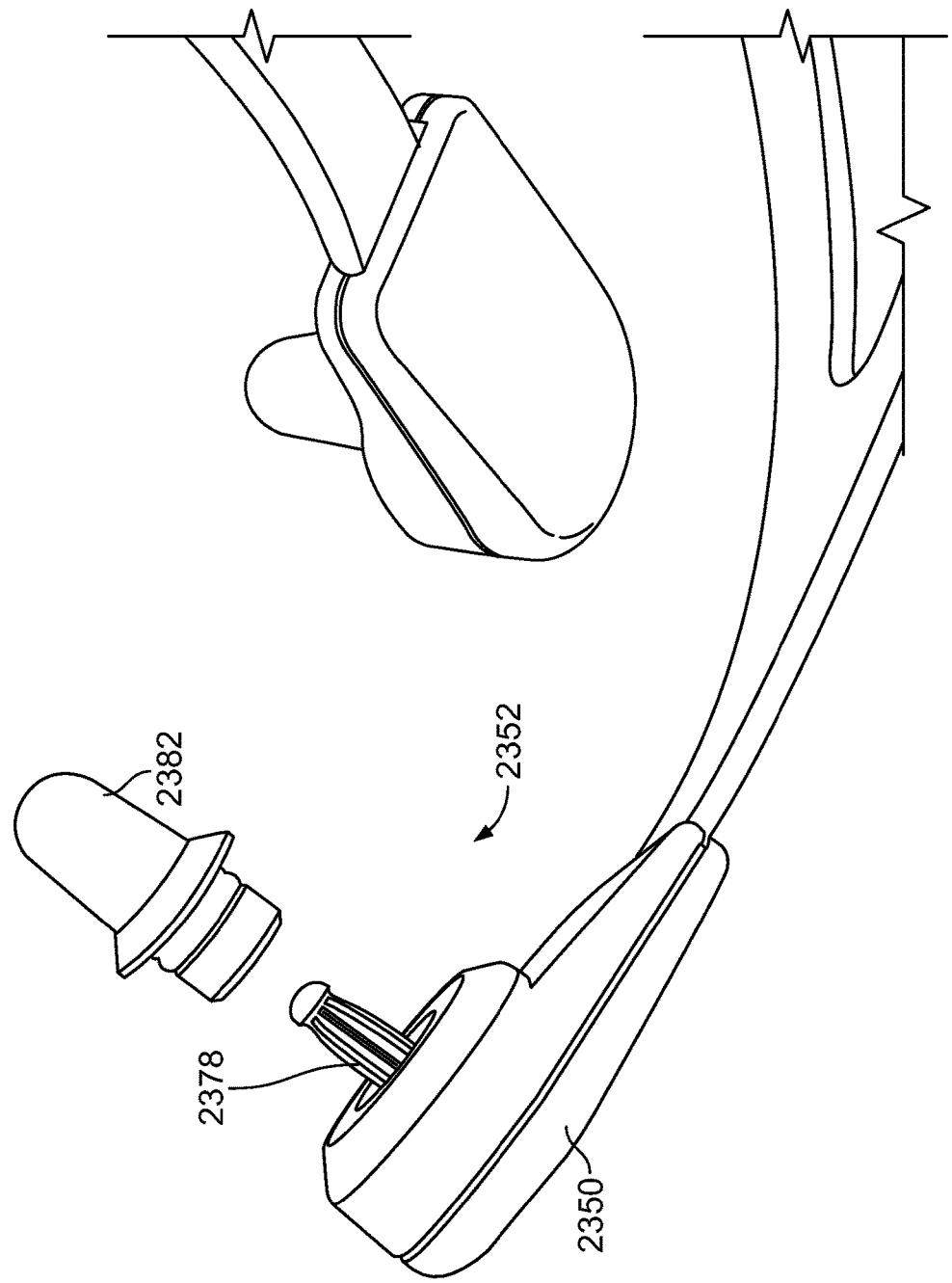
FIG. 33 is a side view of the example electrode connector of FIGS. 32A-32D in a partially assembled state.

FIG. 33 is an enlarged view of the example electrode housing 2350 and the example electrode unit 2352 of FIG. 23. As shown in FIG. 33, the housing encloses the back plate 2374 (shown in FIGS. 32A-32D) but the shaft 2378 extends from the housing to receive the electrode. In the illustrated example, the electrode unit 2352 includes an alternative elongated electrode 2382. In other examples, the electrode has any other shape or size appropriate to contact the scalp of a user to receive electrical signals.

Figure 34:
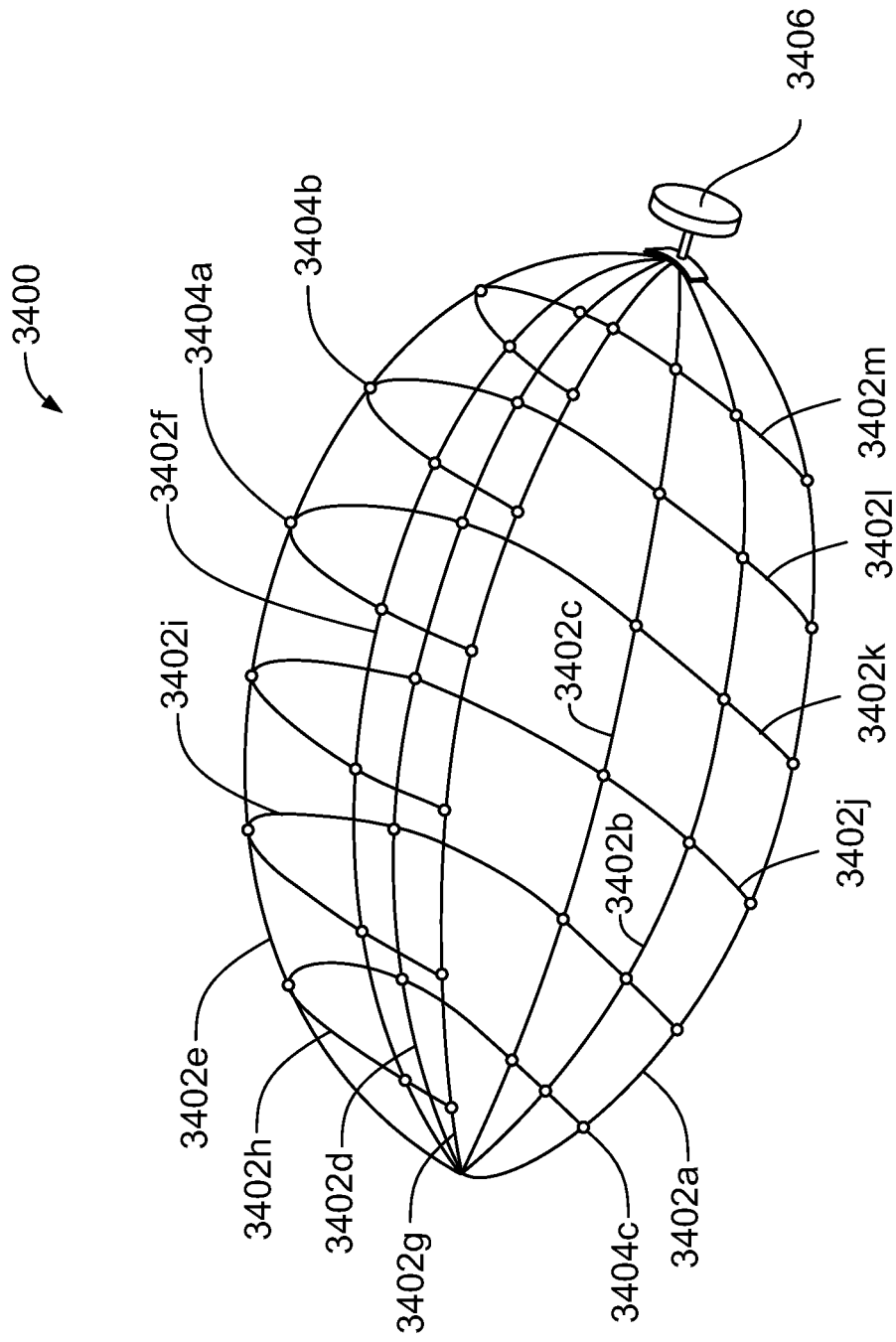
FIG. 34 is a perspective view of another example headset constructed in accordance with the teachings of this disclosure.
Figure 35:
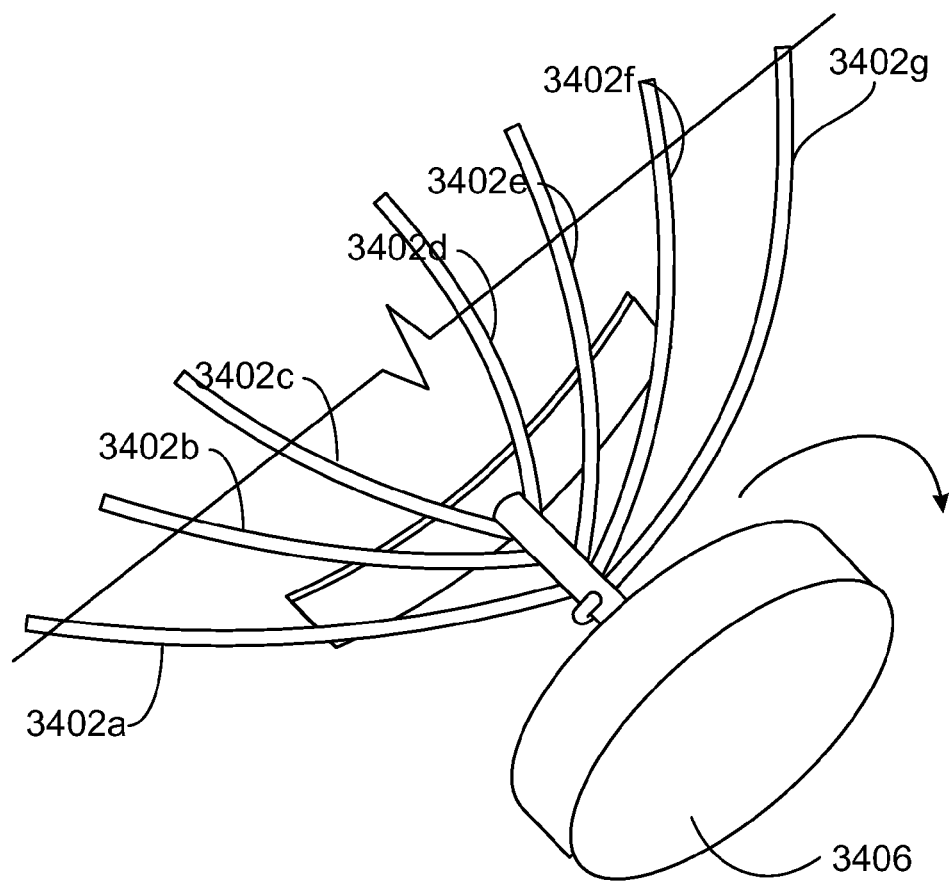
FIG. 35 is a perspective view of an adjustment knob for the example headset of FIG. 34.

FIG. 34 is a perspective view of an example net array headset 3400. The net array headset 3400 includes a plurality of elastic bands 3402a-3402m that forms a zig-zag or criss-cross pattern. An electrode 3404a-3404t is located at each intersection of the elastic bands 3402a-3402m. A plurality of the elastic bands 3402a-3402g converges in the back of the net array headset 3400 and is coupled to an adjustment knob 3406. As the adjustment knob 3406 is turned, the individual elastic bands 3402a-3402m (and others unnumbered) are pulled tight and the electrodes 3404a-3404c (and others unnumbered) are forced downward onto the scalp of a user. The adjustment knob 3406 allows the net array headset 3400 to be adjustably used on a range of differently sized heads. As shown in FIG. 35 the adjustment knob 3406 is rotatable to wind up the individual elastic bands 3402a-3402g and, thus, tighten the net array headset 3400 onto the head of a user. The net array headset 3400 enhances the fit of electrodes on differently shaped heads and produces a light and portable headset.

Figure 36:
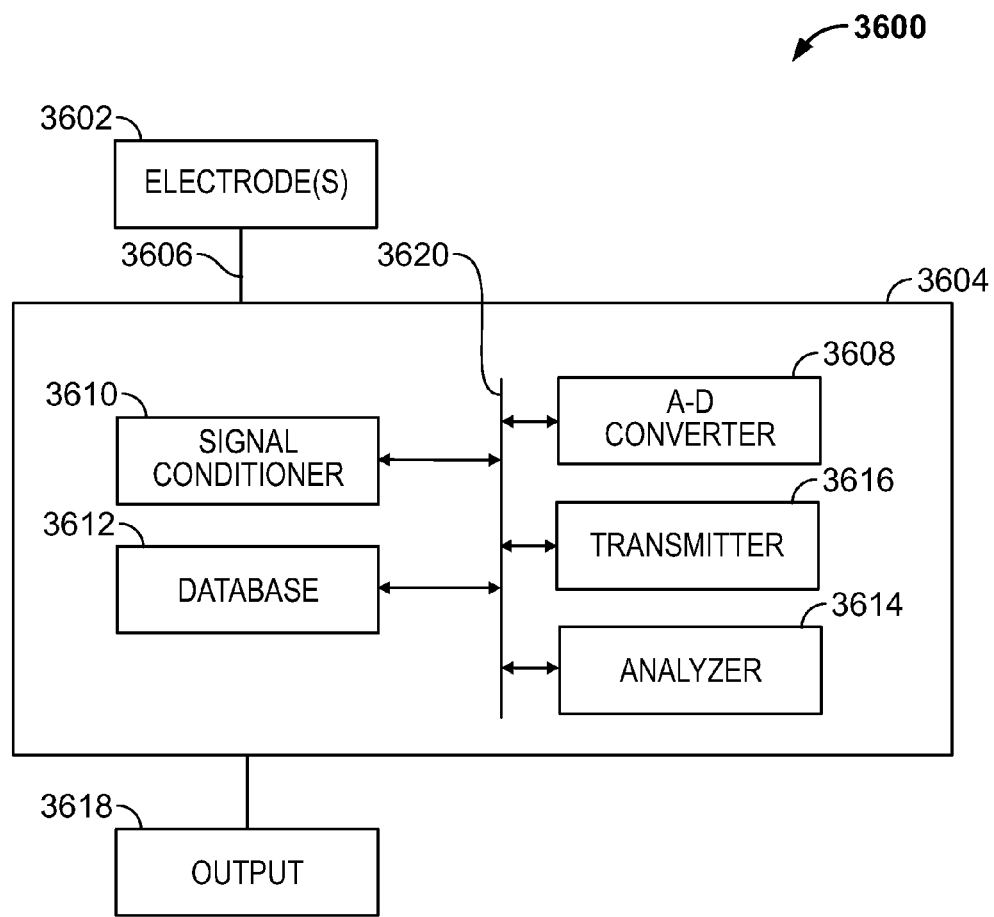
FIG. 36 is a block diagram of an example circuit from the headset in FIGS. 1, 23 and/or 34.

FIG. 36 is a block diagram of an example processing system 3600 for use with any of the headsets disclosed herein. The example system 3600 includes a plurality of electrodes 3602. The electrodes 3602 are coupled, for example, to a headset to be worn on a head of a subject. In some examples, the headset includes a plurality of elongated bands that extend between a first housing located near a first ear of a subject and a second housing located near a second ear of the subject. In some examples, one or more of the elongated bands is rotatably and/or removably coupled to each of the first and second housings such that the electrodes 3602 can be moved to different positions on the head and/or removed from the headset. The headset may include numerous channels of electrodes such that multiple (e.g., 2000 or more) electrodes are included in the example system 3600. In addition, in some examples, the pressure applied on the head by each electrode may be adjusted by adjusting an elastic band or strap associated with each of the elongated bands.

The electrodes may have any suitable shape such as, for example, at least a portion of a ring, a ball, a hook and/or an array. The electrodes 3602 may include one or more of the properties of any of the electrodes disclosed in this patent. In addition, different types of electrodes may be included in the system 3600. Also, in some examples, the electrodes 3602, and the elongated bands to which the electrodes 3602 are coupled, have a protective covering such as, for example, a nylon and/or a silver mesh. In some examples, the covering is a stretchable silver-coated nylon mesh. The covering provides additional shielding and protection. In addition, the electrodes 3602 including the covering may be machine washable.

The example electrodes 3602 may also be adjustably mechanically coupled, such as for example, via the elongated bands to a first housing where an adjustable locking mechanism is supported to releasably hold the elongated bands and, thus, the electrodes 3602 in one or multiple positions. An example locking mechanism includes the magnetic lock disclosed above.

The electrodes 3602 are also communicatively coupled to a second housing (e.g., the second housing 128 of the headset 100 shown in FIG. 1) that supports an electrical processing unit 3604 via a communication line 3606, which may be for example a wired or wireless communication link including, for example, the PCB communication channels disclosed above. The example processing unit 3604 includes an analog-to-digital converter 3608, a signal conditioner 3610, a database 3612, an analyzer 3614 and a transmitter 3616.

The analog-to-digital converter 3608 converts the analog signals received at the electrodes 3602 to digital signals. In some examples, the analog-to-digital converter 3608 is located in the processing unit 3604 at one of the housings of the headset. In other examples, the analog-to-digital converter 3608 comprises multiple A-D converters located to service individual or sets of the electrodes to convert the signals as close to the source as possible, which may further reduce interference.

The signal conditioner 3610 of the illustrated example prepares the gathered signals so that the data is in a more usable form. For example, the signal conditioner 3610 may include an amplifier to amplify the signal to a more detectable level. In addition, the signal conditioner 3610 may include a filter to remove noise from the signal. The filter may also be used as a bandpass filter to pass one or more frequency bands and/or manipulate select bands depending on the desired processing and/or analysis. For example, in analyses to study only the alpha waves, the signal conditioner may be programmed to present only those frequencies between about 7.5 and about 13 Hz. In some examples, each of the electrodes 3602 may include a signal conditioner at or near the electrode 3602. The example signal conditioner 3610 may include hardware and/or software to execute a signal conditioning method. In some examples, the signal conditioner includes a detrending unit to compensate for electrode polarization, in which there is slow movement of the voltage signal unrelated to brain wave activity due to polarization of the electrodes. The example processing unit 3604 also provides signal processing that may include hardware and/or software to execute Fast Fourier Transform (FFT) measurements, coherence measurements and/or custom adaptive filtering.

The analyzer 3614 is to analyze the data gathered from the electrodes 3602 and processed by the analog-to-digital converter 3608 and the signal conditioner 3610 in accordance with one or more analysis protocols depending on the desired study. For example, in accordance with some studies, the analyzer 3614 may process the data to determine one or more of a subject's mental state, physiological state, attention, resonance or memory, emotional engagement and/or other suitable characteristics of the subject.

The transmitter 3616 communicates the data at any stage of processing and/or the results of the analysis from the analyzer 3614 to an output 3618. The output 3618 could be a handheld device, an alarm, a display screen on the headset, a remote server, a remote computer and/or any other suitable output. Data transmission may be implemented by Bluetooth transmission, wi-fi transmission, ZiGBee transmission and/or proprietary encryption before transmission. In the illustrated example, the database 3612 stores all data gathered streams. The streams can be buffered for streaming or stored on-board (i.e., at the headset) for periodic or aperiodic uploads during, for example, low-activity periods.

The processing unit 3604 components 3608-3616 are communicatively coupled to other components of the example system 3600 via communication links 3620. The communication links 3620 may be any type of wired connection (e.g., a databus, a USB connection, etc.) or a wireless communication mechanism (e.g., radio frequency, infrared, etc.) using any past, present or future communication protocol (e.g., Bluetooth, USB 2.0, USB 3.0, etc.). Also, the components of the example system 3600 may be integrated in one device or distributed over two or more devices.

While example manner of implementing the system 3600 has been illustrated in FIG. 36, one or more of the elements, processes and/or devices illustrated in FIG. 36 may be combined, divided, re-arranged, omitted, eliminated and/or implemented in any other way. Further, the example signal conditioner 3610, the example A/D converter 3608, the example database 3612, the example transmitter 3616, the example analyzer 3614, the example output 3618 and/or, more generally, the example system 3600 of FIG. 36 may be implemented by hardware, software, firmware and/or any combination of hardware, software and/or firmware. Thus, for example, the example signal conditioner 3610, the example A/D converter 3608, the example database 3612, the example transmitter 3616, the example analyzer 3614, the example output 3618 and/or, more generally, the example system 3600 of FIG. 36 could be implemented by one or more circuit(s), programmable processor(s), application specific integrated circuit(s) (ASIC(s)), programmable logic device(s) (PLD(s)) and/or field programmable logic device(s) (FPLD(s)), etc. When any of the apparatus or system claims of this patent are read to cover a purely software and/or firmware implementation, at least one of the example signal conditioner 3610, the example A/D converter 3608 or the example database 3612 are hereby expressly defined to include hardware and/or a tangible computer readable medium such as a memory, DVD, CD, etc. storing the software and/or firmware. Further still, the example system 3600 of FIG. 36 may include one or more elements, processes and/or devices in addition to, or instead of, those illustrated in FIG. 36, and/or may include more than one of any or all of the illustrated elements, processes and devices.

Figure 37:
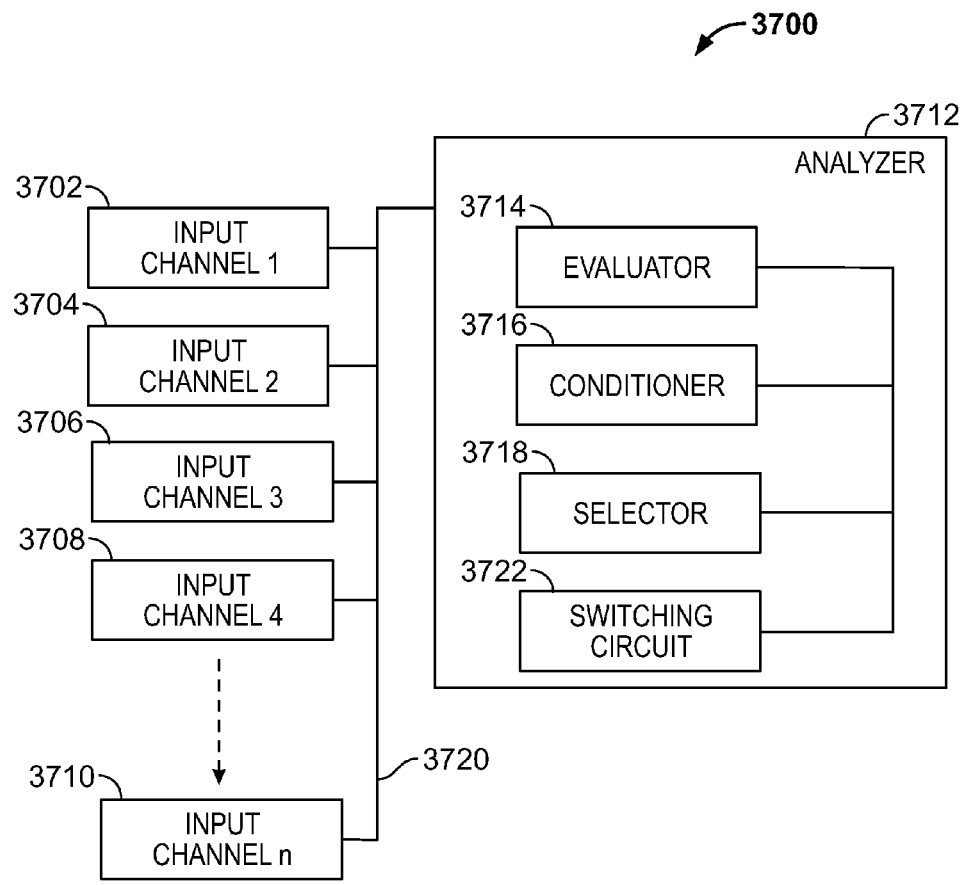
FIG. 37 is a block diagram of an example manner of implementing the processor and signal selector of FIGS. 1-7 and 12.

FIG. 37 illustrates another example system 3700 that may be implemented, for example, by one or more of the example headsets 100, 2300, 3400 shown in FIGS. 1, 23 and 34. The example system 3700 of FIG. 37 may be used to enhance signal strength by, for example, shorting out one or more electrodes to effectively increase a surface area of an electrode using, for example, the example circuit 300 of FIG. 12A. Increasing surface area lowers the impedance and improves the signal-to-noise ratio of the data gathered at the electrode. In addition, the example system 3700 may be used to virtually move an electrode by selecting one or more input channels to choose more effective electrode locations occupied by electrodes obtaining high quality and less noisy signals. These electrodes may be, for example, the electrodes that have optimum or near optimum contact with the scalp. The system 3700 enables a user or an operator to discard electrodes that are inoperable, mis-operating or insufficiently coupled to the scalp and/or the remainder of the headset.

The example system 3700 of FIG. 37 includes any number of input channels (e.g., a first input channel 3702, a second input channel 3704, a third input channel 3706, a fourth input channel 3708 . . . n input channels 3710). For example, as disclosed above, one or more of the headsets disclosed herein may include 2000 or more input channels. In this example, the input channels 3702-3710 are each associated with an electrode. In other examples, one or more of the input channels 3702-3710 may be associated with other type(s) of sensor(s) such as, for example, an eye tracker, a galvanic skin response sensor, a breath rate sensor, a thermometer, a sphygmomanometer to measure blood pressure, a functional magnetic resonance imaging sensor and/or other suitable types of sensors. Such sensor(s) may be freely added or removed. Some sensor(s) may be added to the headset itself, and other sensor(s) may be coupled to an arm, a chest or other body part and communicatively coupled to the headset.

The example system 3700 of FIG. 37 includes an analyzer 3712. In the illustrated example, the analyzer 3712 is implemented by a programmed processor. The example analyzer 1712 of FIG. 37 includes an evaluator 3714, a conditioner 3716 and a selector 3718. In some examples, one or more of the components 3714-3718 of the analyzer 3712 are incorporated into a housing such as, for example, the second housing 128 of the headset 100 shown in FIGS. 1-3. In other examples, one or more of the components 3714-3718 of the analyzer 3712 are incorporated into a handheld device, a local computer, a remote server or other suitable device. The evaluator 3714 evaluates the properties of the incoming signals, such as for example, strength, amplitude, signal-to-noise ratio, duration, stability and/or other suitable signal characteristics indicative of the integrity of the data and/or the quality of the connection between the headset and the scalp. Example methods to determine what signals are acceptable include, for example, comparing one or more aspects of a signal from a given electrode (e.g., its amplitude, frequency, etc.) to one or more of an absolute threshold, a spectral threshold, a ramp-rate threshold, a low-activity (flat) threshold and/or performing a neighborhood correlation between the signal of a given electrode and signals from one or more other electrodes near the given electrode.

The example conditioner 3716 of the illustrated example amplifies and/or filters the signal to improve signal quality. If the conditioner 3716 enhances the quality of a signal to acceptable levels such that the signal is usable, the evaluator 3714 of the illustrated example determines that the integrity of data from the associated electrode is acceptable and that the data does not need to be discarded and/or that the data from the electrode does need to be ignored or discarded.

The selector 3718 of the illustrated example selects which input channels to ignore, use, and/or merge (e.g., average) to improve (e.g., optimize) the overall input based on the determinations of the evaluator 3714. The plurality of input channels 3702-3710 are communicatively coupled to the analyzer 3712 and corresponding components 3714-3718 via communication links 3720 (e.g., any wired or wireless communication links).

In the example system 3700 shown in FIG. 37, the example evaluator 3714 determines which of the input channels 3702-3710 (e.g., electrodes) are collecting the best, most useful, and/or most accurate data. Based on this determination, the example selector 3718 identifies which electrodes/input channels are most effective (e.g. for the best EEG readings) and which electrodes/input channels should be ignored to improve the readings. Ignoring an electrode/communication may involve disabling the channel (e.g., via a switching circuit) and/or ignoring the data it collects. Disabling an electrode effectively increases the surface area contact between one or more electrodes adjacent the disabled electrode and the tissue on the scalp. Disabling one electrode/channel can be referred to as shorting out the electrode. By shorting out an input channel (e.g., effectively increasing the effective surface area of another electrode at an adjacent input channel), the overall impedance of the channels is lowered and signal quality is improved. Lower impedance and better signal-to-noise ratio enables the example system 3700 of FIG. 37 to read higher frequency bands. Selection of which electrode(s) are candidates for shorting is based on regional coverage and data quality. For example, if there is increased noise in multiple electrodes in a small neighborhood of electrodes, some or all of such electrodes can be shorted to improve the signal to noise ratio. Furthermore, with a large number of input channels, the selector 3718 may determine which electrodes are in best contact with the scalp and gathering the clearest signal. Other electrodes in the vicinity may be ignored and/or shorted out with a switching circuit 300 (FIG. 12A), 3722 (FIG. 37). In addition, if an input channel provides a relatively weak signal and an adjacent input channel provides a stronger signal, the selector 3718 emphasizes the input channel with the stronger signal by deselecting the channel with the weaker signal. Deselecting a signal (e.g., disabling it via the switching circuit 3722) and relying on the data collected by adjacent electrodes can be thought of as moving the function of the deselected electrode to the adjacent electrode. Thus, the example system 3700 of FIG. 37 can virtually move an electrode to a stronger signal gathering position without having to physically adjust any mechanical components (i.e., without physically moving the electrode over).

While example manner of implementing the system 3700 has been illustrated in FIG. 37, one or more of the elements, processes and/or devices illustrated in FIG. 37 may be combined, divided, re-arranged, omitted, eliminated and/or implemented in any other way. Further, the example analyzer 3712, the example evaluator 3714, the example conditioner 3716, the example selector 3718, the example switching circuit and/or, more generally, the example system 3700 of FIG. 37 may be implemented by hardware, software, firmware and/or any combination of hardware, software and/or firmware. Thus, for example, the example analyzer 3712, the example evaluator 3714, the example conditioner 3716, the example selector 3718, the example switching circuit 3720 and/or, more generally, the example system 3700 of FIG. 37 could be implemented by one or more circuit(s), programmable processor(s), application specific integrated circuit(s) (ASIC(s)), programmable logic device(s) (PLD(s)) and/or field programmable logic device (s) (FPLD(s)), etc. When any of the apparatus or system claims of this patent are read to cover a purely software and/or firmware implementation, at least one of the example analyzer 3712, the example evaluator 3714, the example conditioner 3716, the example selector 3718 or the example switching circuit 3720 are hereby expressly defined to include hardware and/or a tangible computer readable medium such as a memory, DVD, CD, etc. storing the software and/or firmware. Further still, the example system 3700 of FIG. 37 may include one or more elements, processes and/or devices in addition to, or instead of, those illustrated in FIG. 37 and/or may include more than one of any or all of the illustrated elements, processes and devices.

Figure 38:
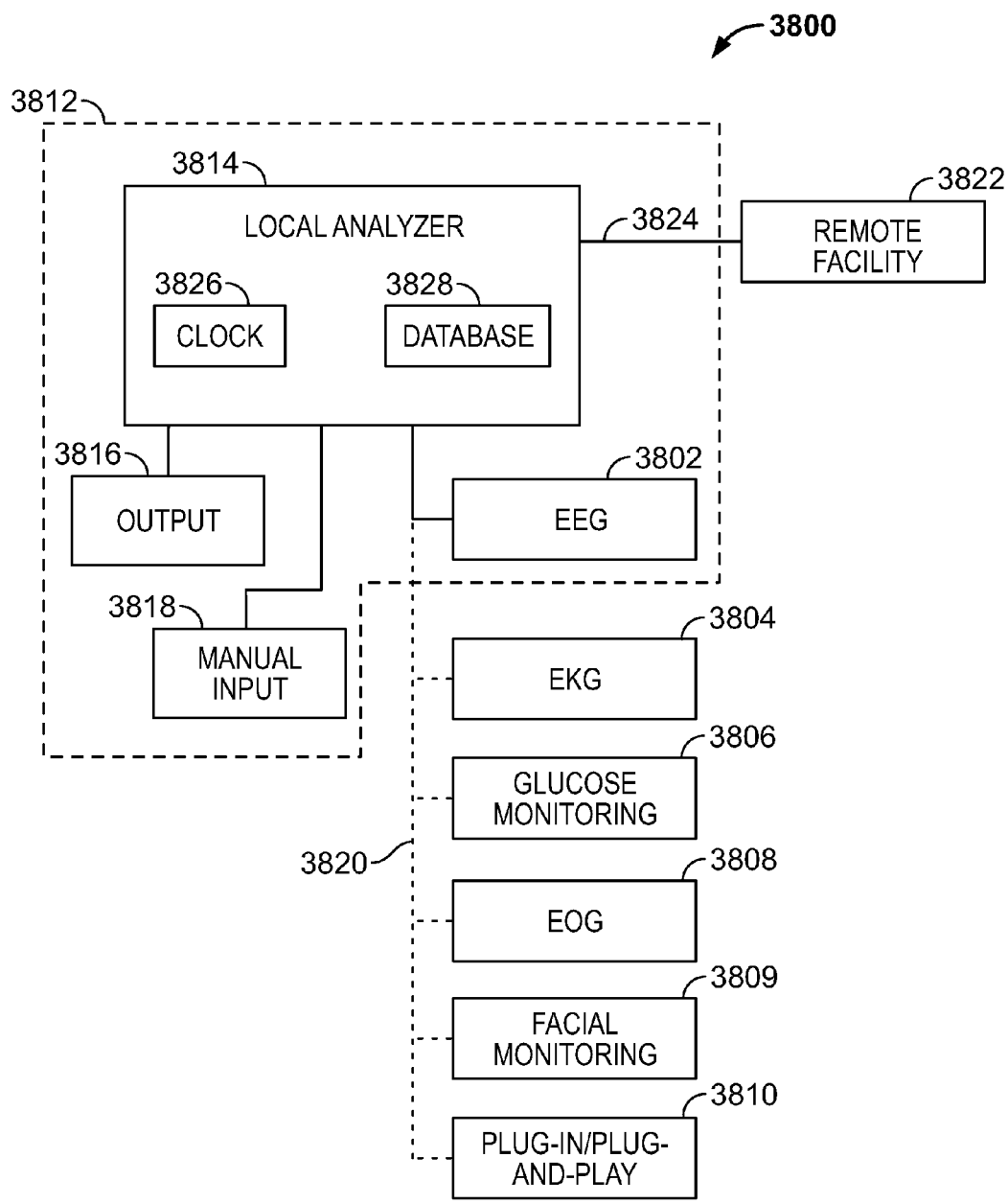
FIG. 38 is a block diagram of an example manner of implementing the headset(s) of FIGS. 1, 23 and/or 34 with additional physiological sensor systems.

FIG. 38 illustrates an example system 3800 that includes a headset 3812, which is representative of one or more of the example headsets and/or systems described herein, such as, for example, the headset 100 of FIG. 1, the headset 2300 of FIG. 23, the headset 3400 of FIG. 34, the system 3600 of FIG. 36, the system 3700 of FIG. 37 and/or the system 3900 of FIG. 39 (disclosed below) with additional physiological sensor(s). The example system 3800 may be used for in-home patient monitoring, treatment and/or diagnosis of medical conditions, to detect life-threatening situations, to ascertain patient compliance with a prescribed medical regime and/or other suitable applications. Currently patients need to go to the hospital for neurological monitoring. This entails increased risk of exposure to hospital pathogens (such as, e.g., acquired bacterial infections). However, in a hospital environment, there are skilled technicians to monitor the data, detect issues and alarm medical staff. Though there is no guarantee that data of interest defining neurological status will not be missed. In the home environment, the example headsets and/or systems disclosed herein automatically monitor the data, detect issues, and alarm the patient, an emergency call center, paramedics, a doctor and/or a local hospital if there are medical issues and/or emergencies. For example, a patient may have an aura (warning) of a seizure at home and not have time to get to the hospital for monitoring. A self-applied, home EEG monitoring system including the examples headsets disclosed herein enable the capture this information critical for appropriate care. In addition, the self-application systems disclosed herein enable a patient to transmit data, question (s), communication(s) and/or other information to a medical care professional when the patient feels there is something symptomatically wrong with their physiology including, for example, underperformance in the cognitive domain. Furthermore, hospitals have skilled technicians to monitor data quality and equipment function. Examples disclosed herein automatically perform those functions, thereby achieving cost savings and reducing the possibility of human error.

Also, the headsets and/or systems produce data that may be used with telecommunication and/or other information technologies to provide clinical health care from a remote location. For example, a patient may be examined and/or monitored by sending sensor data to a remote doctor or physician. In some examples, EKG data may be monitored such as, for example, 24 hour at home monitoring of cardiac arrhythmia patients. In such examples, an EKG sensor is attached to the in-home patient whereby the system is coupled to a phone line, the internet or other communication link. The EKG readings are transmitted directly to the patient's cardiologist (and/or a technician, nurse, etc.) over the communication link. The example system 3800 of FIG. 38 is usable for many type(s) of patients with many type(s) of conditions including cardiac arrhythmia, epileptic seizures, stroke, small vessel disease, dementia, memory loss, Alzheimer's, glucose monitoring, blood pressure, hypertonia, cognitive decline, depression and/or other conditions. Other physiological conditions, psychiatric conditions, disease progression, disease intervention effectiveness and/or developmental disorders are also monitorable with the system, 3800 such as, for example, bipolar disorder, schizophrenia, attention deficit hyperactivity disorder (ADHD) and/or autism.

With respect to EEG data and the headsets used to gather the data, traditional systems have been uncomfortable to wear, require messy gels, are costly to manufacture and/or require extensive training to use. Example headsets 100, 2300, 3400, 3812 disclosed herein are useful (e.g., optimal) for in-home patient monitoring because such disclosed headsets 100, 2300, 3400, 3812 are comfortable to wear, easy to operate, provide effective electrode-to-tissue contact, comprise a large number of electrodes and/or are adjustable to accommodate differently sized heads. In some examples, data from the example headsets 100, 2300, 3400, 3812 is processed at the headset and transmitted to an off-site monitoring station for analysis by medical personnel (e.g., a doctor or physician). In some examples, data storage occurs at the headset, at a remote data center or a combination thereof.

The example headsets 100, 2300, 3400, 3812 disclosed herein are combinable with additional biometric, neurological and/or physiological system(s) to monitor, examine, treat and/or diagnosis multiple medical conditions including physiological conditions and/or mental conditions. In the example system 3800, data from an EEG system 3802 is combined and aggregated with data from an EKG system 3804, a glucose monitoring system 3806, an EOG system 3808, a facial monitoring system 3809 and/or any other plug-in/play-and-play system 3810 (e.g., installable or couplable programs and/or devices to add additional functionality), such as for example, eye-tracking sensor(s) (e.g., the eye tracking sensor 3910 of FIG. 39), galvanic skin response (GSR) signal(s), EMG signal(s), camera(s), infrared sensor (s), interaction speed detector(s), touch sensor(s) and/or any other sensor capable of outputting physiological and/or neurological data to the headset 3812 or directly to the off-site monitoring station. In addition, in some examples, the example facial monitoring system 3809 includes to have a full facial and/or hemifacial coverage camera to enable facial affect coding (FACS), which allows categorization of facial expressions. In some examples, the example facial monitoring system 3809 includes a camera coupled to a telescopic boom.

In the illustrated example, the headset 3812 includes the EEG system 3802, a local analyzer 3814 (which, for example, may be incorporated into the second housing 128 of the headset 100 of FIG. 1), an output 3816 and a manual input 3818. In the illustrated example, the sub-systems 3802-3810 are communicatively coupled the headset 3812 and, thus, the local analyzer 3814 via communication link 3820, which may include hard wire and/or wireless technology. Also, in some examples, one or more the sub-systems 3802-3810 may be incorporated into the headset itself (e.g., the EOG system 3808 and/or the facial monitoring system 3809).

Each of the signals from the different sub-systems 3802-3810 represents an input. Each input may be filtered, conditioned and/or processed to formulate an output representing one or more properties or characteristics of the patient's condition. In the illustrated example, the EKG system 3804 is coupled to a patient's chest, and the EKG data is wirelessly sent to the EEG headset 3812. The EKG data is processed by the local analyzer 3814 and sent to a remote facility 3822 for treatment, diagnosis and/or monitoring of the patient. The remote location may be, for example, a doctor's office, a hospital, a clinic, a laboratory, an archive, a research facility and/or any other diagnostic facility. The local analyzer 3814 may be communicatively coupled to the remote facility via a communication channel 3824 such as common telephone line, landline, an internet connection, radio waves, and/or any other communication technology capable of sending signals. In the example shown in FIG. 38, the local analyzer 3814 includes a clock 3826 and a database 3828. The clock 3826 of the illustrated example time stamps the data for use, for example, in monitoring the progress of a condition or a treatment and/or generating medical records. The database 3828 of the illustrated example is used for local storage.

In the example shown in FIG. 38, the local analyzer 3814 creates the output 3816. The output 3816 may be, for example, a light, a sound, a display and/or any other output that may be used, for example, to alert a patient of a need to seek medical attention, to take a dosage of medicine, to start an activity, to stop an activity, to eat something and/or any other suitable warning and/or command. In some examples, the output 3816 is operatively coupled to an auto-delivery system for automatically delivering medicine to a patient in response to certain readings from the system 3800. Diabetic patients, for example, often require continuous glucose and blood pressure monitoring. The example system 3800 may monitor and deliver insulin automatically to a patient based on the measured physiological characteristics. In the example shown, the output 3816 (e.g., a light, a speaker, a display, an auto-delivery system) is incorporated into the headset 3812. In other examples, the output 3816 may be separate from the headset 3812, and the headset may communicate with the output 3816 via the wired or wireless communication links disclosed herein.

The example system 3800 maybe be used to detect and/or treat psychiatric conditions such as, for example, depression. For example, a patient's brain waves may be monitored by headset 3812 via the EEG sub-system 3802. If the local analyzer 3814 detects that the patient is becoming more depressed, then small doses of anti-depressants may be automatically injected and/or the output 3816 may sound an audible message or alarm that directs the patient to self-administer a dosage of medicine. Alternatively, the output signal 3816 may be communicatively coupled to a remote monitoring station such as a doctor's pager, such that when certain readings indicate that the patient has developed a dangerous condition, a doctor is paged to respond and/or an alarm is set to direct the patient to seek medical attention.

Another benefit to the at-home system 3800 is the volume and completeness of patient data due to the continual recording and measuring of patient vitals and/or other physiological and/or neurological condition(s). Commonly, people are asked what they were doing just before and after an occurrence of a medical event, such as for example, a seizure. Patients often experience difficulty tracking and/or recalling their day-to-day activities with such precision. However, with the example system 3800, the local analyzer 3814 records the patient's statistics and/or activities. The example self-application systems disclosed herein enable the development of daily logs or flow charts of brain activity, which is usable to identify relationships among and/or trends in behavior, medication and physiological performance. Also, in some examples, the headset is provided with geographic tracking technology (e.g., GPS, etc.) to identify where a patient is located (e.g., the kitchen, a neighbor's home, the living room, etc.) at certain times. In some examples, the local analyzer 3814 prompts the patient to enter his or her daily activity periodically or as specific medical events occur such as, for example, as spikes in one or more readings occur. The example system 3800 of FIG. 38 includes the manual input 3818 to facilitate patient entry of such information. In some examples, the manual input 3818 is carried by the headset 3812. For example, the manual input 3818 may be an interactive (e.g., touch) screen, a microphone and/or a keypad on a surface of the headset 3812. In other examples, the manual input 3818 could be a remote device such as, for example, a handheld device, a computer, a mobile phone, a tablet and/or a television that is communicatively coupled to the system 3800.

Thus, the examples disclosed herein enable the collection, recordation, charting and/or development of baseline activity and a comparison of patient activity to the baseline on an on-going basis. The baseline development is patient-specific based on the volume of gathered data. Therefore, the baseline is not based on societal norms or averages, but rather, is shiftable and adaptable to the individual patient. The example systems and headsets disclosed herein also include on-board storage, processor, time tracking and spectral tracking to enable continuous charting/status evaluation for patients, medication usage and/or feedback improvement applications to increase patient compliance and/or response. In some examples, the self-application systems disclosed herein also provide prompts on/in response to potential salient events. For example, the examples disclosed herein can prompt to a patient to go see a physician if needed. In some examples, the prompts are based on changes in mental states and/or activities and/or significant deviations from the individual patient's norms such that the response or action prompt is tailored to the specific individual.

The volume and completeness of data collected by the example system 3800 enable the development of real-time reports that provide effective data in diagnosing and treating medical conditions. For example, a patient with ADHD may have a reading that indicates he/she is having increased brain activity in certain regions of the brain associated with lack of concentration. In response, the local analyzer 3814 may prompt the user via the manual input 3818 to enter what he/she was recently doing (e.g., drinking a can of cola). In another example, a depressed patient may have a reading indicating he/she is cheerful and happy. The local analyzer 3814 will prompt the patient to record what he/she was doing just prior to the reading. Such activity may be incorporated into a treatment plan to assist the patient in maintaining a desired mental state (e.g., happiness). In another example, a person with high blood pressure may be monitored. If his/her blood pressure increased, the patient may be asked what he or she ate or drank just prior to the reading. Therefore, with the example system 3800, a patient can readily input data, and the physician can interpret the data and more accurately diagnosis health conditions and/or activities that affect such conditions.

While example manners of implementing the system 3800 have been illustrated in FIG. 38, one or more of the elements, processes and/or devices illustrated in FIG. 38 may be combined, divided, re-arranged, omitted, eliminated and/or implemented in any other way. Further, the example local analyzer 3814, the example clock 3826, the example database 3828, the example output 3816, the example manual input 3818, the example EEG sub-system 3802, the example EKG sub-system 3804, the example glucose monitoring sub-system 3806, the example EOG sub-system 3808, the example facial monitoring system 3809, the example plug-in/plug-and-play 3810 and/or, more generally, the example system 3800 of FIG. 38 may be implemented by hardware, software, firmware and/or any combination of hardware, software and/or firmware. Thus, for example, the example local analyzer 3814, the example clock 3826, the example database 3828, the example output 3816, the example manual input 3818, the example EEG sub-system 3802, the example EKG sub-system 3804, the example glucose monitoring sub-system 3806, the example EOG sub-system 3808, the example facial monitoring system 3809, the example plug-in/plug-and-play 3810 and/or, more generally, the example system 3800 of FIG. 38 could be implemented by one or more circuit(s), programmable processor(s), application specific integrated circuit(s) (ASIC (s)), programmable logic device(s) (PLD(s)) and/or field programmable logic device(s) (FPLD(s)), etc. When any of the apparatus or system claims of this patent are read to cover a purely software and/or firmware implementation, at least one of the example local analyzer 3814, the example clock 3826, the example database 3828, the example output 3816, the example manual input 3818, the example EEG sub-system 3802, the example EKG sub-system 3804, the example glucose monitoring sub-system 3806, the example EOG sub-system 3808, the example facial monitoring system 3809 or the example plug-in/plug-and-play 3810 are hereby expressly defined to include hardware and/or a tangible computer readable medium such as a memory, DVD, CD, etc. storing the software and/or firmware. Further still, the example system 3800 of FIG. 38 may include one or more elements, processes and/or devices in addition to, or instead of, those illustrated in FIG. 38, and/or may include more than one of any or all of the illustrated elements, processes and devices.

Figure 39:
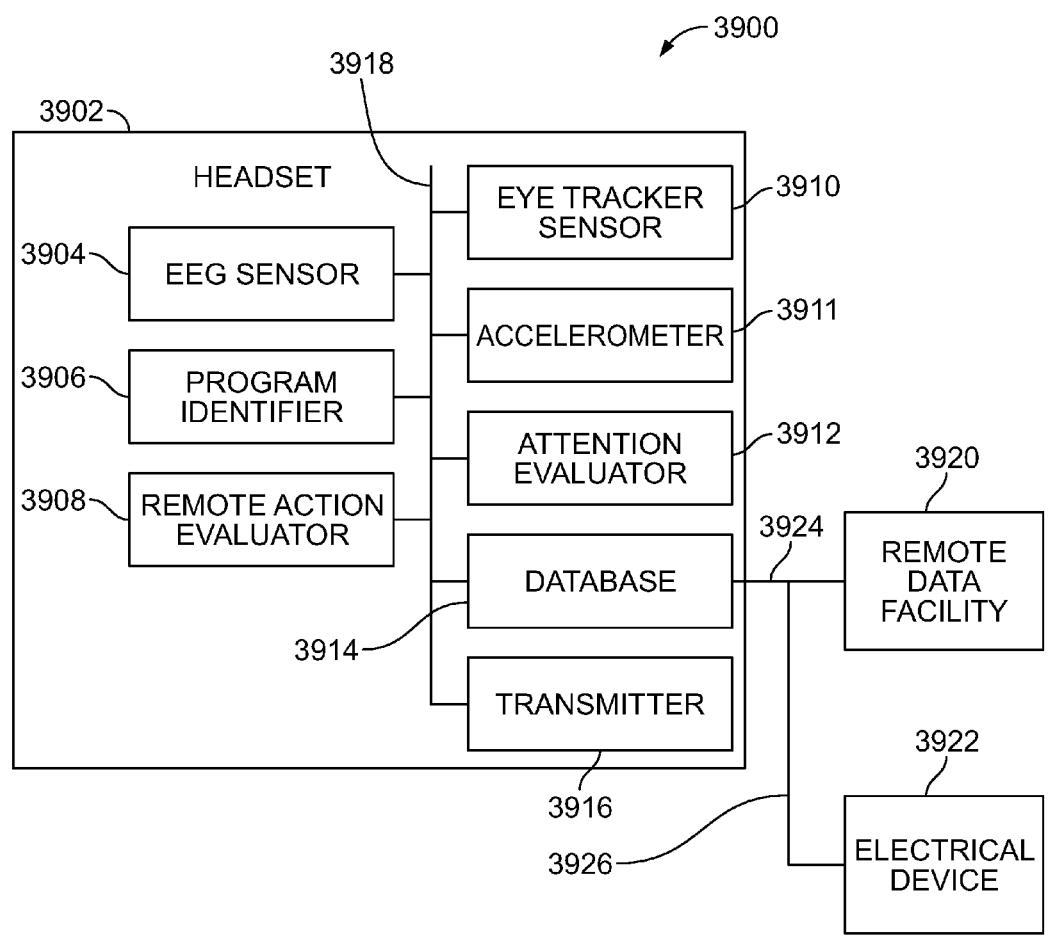
FIG. 39 is a block diagram of an example manner of implementing the processing and conditioning of FIGS. 1, 23 and 34.

FIG. 39 illustrates an example attention and control system 3900 that may be used for determining, processing and/or evaluating a user's attention to media and/or to manipulate an input on an external electrical device without physical movement, (e.g., by using only the user's mind).

The example system 3900 includes a headset 3902, which may be implemented for example, with the example headsets and/or systems disclosed herein such as, for example, the headset 100 of FIG. 1, the headset 2300 of FIG. 23, and/or the headset 3400 of FIG. 34. The headset 3902 processes EEG signals and/or other sensor data to develop a picture of a mental state of a user including, for example, an emotional state, a state of engagement, a state of attention and/or any other neurological state. As disclosed below, the example system 3900 of FIG. 39 may be used to determine if the user is paying attention to a media program, to determine where a users eyes are focused, to determine that the user wants to control a remote device and effect that control (e.g., change the volume on a television), and/or for other applications. In the illustrated example system 3900, the headset 3902 includes analyzer components including an EEG sensor 3904, a program identifier 3906, a remote action evaluator 3908, an eye tracker sensor 3910, an accelerometer 3911, an attention evaluator 3912, a database 3914 and a transmitter 3916. The analyzer components 3904-3914 are communicatively coupled via a communication link 3918 such as, for example, any communication described above. The analyzer components 3904-3914 may be, for example, incorporated into or otherwise supported by the headset 3902 such as the headset 100 shown in FIG. 1, the headset 2300 shown in FIG. 23 or the headset 3400 shown in FIG. 34. In some examples, the analyzer components 3904-3916 are housed in a compartment on a headset, such as, for example, the second housing 128 of the headset 100 shown in FIGS. 1-3.

As disclosed above example headsets 100, 2300, 3400 include a plurality of individual electrodes to detect electrical activity along the scalp of a user. This data may be used to determine attention, memory, focus and/or other neurological states. The EEG sensor 3904 of the example of FIG. 39 is implemented by the electrodes of the headsets disclosed above.

The example eye tracker sensor 3910 is used to track eye movement and/or the direction in which a user's eyes are directed. For example, the eye tracker sensor 3910 may be a camera or other sensor that is incorporated into an appendage that extends from the headset 3902 and is directed to one or both of the user's eyes. In other examples, the eye tracker sensor 3910 may be a camera or other sensor on or near a computer, a television, a mobile phone screen or other location to gather data related to the user's eye movement. The eye tracker sensor 3910 may continuously record what the subject is seeing. In some examples, the eye tracker sensor is placed around the middle of the subject's eyebrows. Also, in some examples, the eye tracker sensor includes a monocular or binocular (e.g., one eye or two eye coverage) infra-red (IR) camera to track the pupil and/or corneal reflection positions to aide in determining a point of regard of the subject's viewpoint. In some examples, the eye tracker sensor 3910 incorporates and/or is used in conjunction with an accelerometer/attitude measurement system 3911. Many mobile eye-tracking systems that are mounted to a subject's head are susceptible to erroneous measurements as the subject moves his or her head relative to the position he or she had during calibration of the system. The example accelerometer 3911 continuously tracks the relative eye position from calibration, which enhance the accuracy of the point-of-regard measurement from the eye-tracking sensor 3910.

The eye track data may be synchronized with and/or otherwise used to corroborate the EEG data or otherwise may be used in conjunction with the EEG to determine a neurological state of the user. Eye movements provide a target of a user's attention allocation. For example, if the user is looking in the direction of a television and his or her EEG data indicates that he or she is in a state of engagement or attention, the eye track data and EEG data together demonstrate that the attention was likely directed to the television.

The example system of FIG. 39 also includes a database 3914 for local storage of raw data, processed data, result data, history logs, programming data from a media source, and/or any other type of data. The transmitter 3916 of the illustrated example communicates the data at any stage of processing and/or the results of the analysis from the headset 3902 to a remote data facility 3920 and/or an electrical device 3922, as disclosed in more detail below.

In some example implementations, the system 3900 is used to collect audience measurement data. The example system 3900 determines if a user's neurological state indicates that the user is focused (e.g., engaged with the media) while watching a certain media. The program identifier 3906 identifies media to which the user is exposed. The program identification can be done with any technology, for example, the program can be identified by collecting audio codes and/or signatures using a microphone on the headset to collect audio signals as disclosed in Thomas, U.S. Pat. No. 5,481,294. The program identifier 3906 collects data concerning the media, such as, for example, a television show, an advertisement, a movie, a news clip, radio program, a web page, or any other media and identifies the media (e.g., content or advertisement) based on the collected data and/or forwards the collected data to another device to perform the identification.

In the collection of audience measurement data, the example system 3900 gathers EEG data from the EEG sensors 3904 of the headset 3902. The system gathers eye tracking data from the eye tracking sensor 3910 to determine which direction the user is gazing during the media broadcast. The attention evaluator 3912 uses data from the EEG sensor 3904 and the eye tracker sensor 3910 to determine if a user paying attention to the media. For example, if the EEG sensors 3904 detect brain waves (i.e., electrical activity) indicative of increased thought, and the eye tracking sensor 3910 determines that the user is looking at the TV, the attention evaluator 3912 will output a signal that the user is focused and immersed in that particular media program being broadcast. However, if the program identifier 3906 determines a certain program is being presented, and the EEG sensors 3904 indicate decreasing brain activity, or if the eye tracker sensor 3910 determines the user is not looking at the TV, then the attention evaluator 3912 will output a signal that the user is not focused or immersed on that particular media program.

Data reflected of the user paying attention, the user not paying attention, or the user in a state of semi-involvement with the program and the identity of the program are storable in the database 3914 and transmittable by the transmitter 3916 to an output including, for example, a remote data facility 3920. Raw data, processed data, a history log or an indicator of audience measurement also may be transmitted to the remote data facility 3920 for collection. The remote data facility 3920 may be, for example, a marketing company, a broadcast company, an entertainment studio, a television network and/or any other organization that might benefit from or otherwise desire to know when users are and/or are not focused on broadcast programs and what those programs are. In some examples, the headset 3902 is communicatively coupled to the remote data facility 3920 via a communication channel 3924 such as common telephone line, a landline, an internet connection, radio waves, and/or any other communication technology capable of sending signals. This example allows broadcasting companies and/or marketing personnel to analyze which programs people are watching, when they are watching the programs and/or when they are focused during the broadcast.

In another example implementation, the example system 3900 and headset 3902 operate as a direct neural interface or brain-machine interface (BMI) that is to generate an input for an electrical device 3922 such as, for example, a television, a radio, a computer mouse, a computer keyboard, a remote control, a microwave, an application interface and/or other devices. The input signal for the electrical device 3922 is based on data from the EEG sensor 3904 and/or the eye tracker sensor 3910 of the headset 3902. For example, the eye tracker sensor 3910 determines that the user is gazing at a certain area of his/her computer and the EEG sensors 3904 detect electrical activity indicative of focus. The system 3900 used to control the electrical device 3922 uses specific EEG signatures that trigger control including, for example, signatures in the somatosensory system that are focal over the sensorimotor cortex contralateral to movement and include changes in mu (e.g., 10-14 Hz) and beta (e.g., 15-30 Hz) rhythms. Based on the EEG and eye tracking data, the remote action evaluator 3908 of the headset 3902 determines that the user wants to move his or her cursor (i.e., mouse) to a different region of the computer screen. The remote action evaluator 3908 sends a signal via the transmitter 3916 to the electrical device 3922 to move the cursor on the screen. In another example, the remote action evaluator 3908 analyzes data from the EEG sensor 3904 and determines that a user wants to change a volume level on the television. The remote action evaluator 3908 transmits a signal via the transmitter 3916 to the electrical device 3922 (i.e., the television or cable receiver) to change the volume level. In the example shown, the headset 3902 is communicatively coupled to the electrical device 3922 via a communication line 3926, which may be a hard wire or wireless communication technology such as, for example, any of the communication links discussed herein. In some examples, the remote action evaluator develops signals to conduct a plurality of other functions, such as, for example, muting a television, changing a channel, powering a television, computer or other device on/off, opening a specific program on a computer, setting a microwave, making a musical selection, operating a remote control device, operating a stereo in an automobile, operating a light switch, answering a phone, operating a DVR (digital video recorder) and/or video-on-demand and/or any other function which typically involves the user pressing a button on a device or a remote control of the device. EEG signals including changes in somatosensory mu and beta rhythms are also used in other brain machine interface applications including, for example, driving a wheelchair, controlling a small robot, controlling exoskeletal devices on paralyzed limbs and/or other functions.

While example manner of implementing the system 3900 has been illustrated in FIG. 39, one or more of the elements, processes and/or devices illustrated in FIG. 39 may be combined, divided, re-arranged, omitted, eliminated and/or implemented in any other way. Further, the example program identifier 3906, the example remote action evaluator 3908, the example attention evaluator 3912, the example database 3914, the example transmitter 3916, the example remote data facility 3920, the example electrical device 3922 and/or, more generally, the example system 3900 of FIG. 39 may be implemented by hardware, software, firmware and/ or any combination of hardware, software and/or firmware. Thus, for example, the example program identifier 3906, the example remote action evaluator 3908, the example attention evaluator 3912, the example database 3914, the example transmitter 3916, the example remote data facility 3920, the example electrical device 3922 and/or, more generally, the example system 3900 of FIG. 39 could be implemented by one or more circuit(s), programmable processor(s), application specific integrated circuit(s) (ASIC (s)), programmable logic device(s) (PLD(s)) and/or field programmable logic device(s) (FPLD(s)), etc. When any of the apparatus or system claims of this patent are read to cover a purely software and/or firmware implementation, at least one of the example program identifier 3906, the example remote action evaluator 3908, the example attention evaluator 3912, the example database 3914, the example transmitter 3916, the example remote data facility 3920 or the example electrical device 3922 are hereby expressly defined to include hardware and/or a tangible computer readable medium such as a memory, DVD, CD, etc. storing the software and/or firmware. Further still, the example system 3900 of FIG. 39 may include one or more elements, processes and/or devices in addition to, or instead of, those illustrated in FIG. 39, and/or may include more than one of any or all of the illustrated elements, processes and devices.

FIGS. 40-44 are flowcharts representative, at least in part, of example machine readable instructions that may be executed to implement the example headsets 100, 2300, 3400, 3812, 3902 and/or example systems 3600, 3700, 3800, 3900. In the examples of FIGS. 40-44, the machine readable instructions include a program for execution by a processor such as the processor 4512 shown in the example processing platform 4500 discussed below in connection with FIG. 45. The program may be embodied in software stored on a tangible computer readable medium such as a CD-ROM, a floppy disk, a hard drive, a digital versatile disk (DVD), or a memory associated with the processor 4512, but the entire program and/or parts thereof could alternatively be executed by a device other than the processor 4512 and/or embodied in firmware or dedicated hardware. Further, although the example program is described with reference to the flowcharts illustrated in FIG. 40-44, many other methods of implementing the example headsets 100, 2300, 3400, 3812, 3902 and/or example systems 3600, 3700, 3800, 3900 may alternatively be used. For example, the order of execution of the blocks may be changed, and/or some of the blocks described may be changed, eliminated, or combined.

As mentioned above, the example processes of FIGS. 40-44 may be implemented, at least in part, using coded instructions (e.g., computer readable instructions) stored on a tangible computer readable medium such as a hard disk drive, a flash memory, a read-only memory (ROM), a compact disk (CD), a digital versatile disk (DVD), a cache, a random-access memory (RAM) and/or any other storage media in which information is stored for any duration (e.g., for extended time periods, permanently, brief instances, for temporarily buffering, and/or for caching of the information). As used herein, the term tangible computer readable medium is expressly defined to include any type of computer readable storage medium and to exclude propagating signals. Additionally or alternatively, the example processes of FIGS. 40-44 may be implemented, at least in part, using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Figure 40:
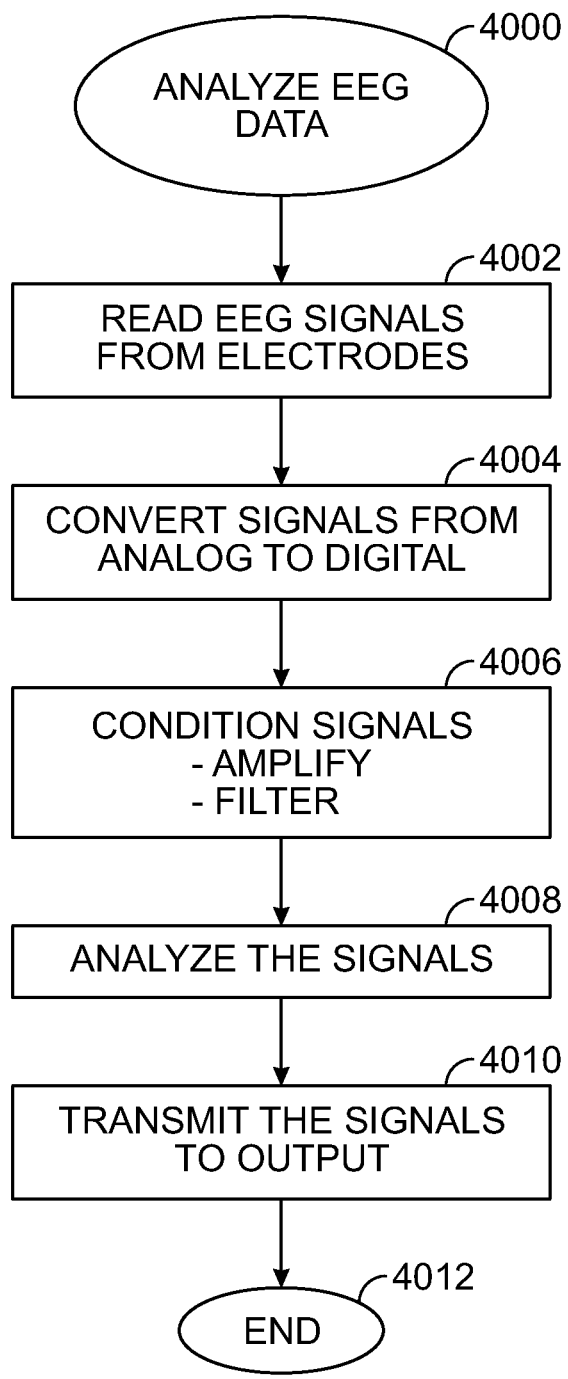
FIG. 40 is a flow chart representing an example method of analyzing EEG data in accordance with the teachings of this disclosure.

FIG. 40 is a flowchart illustrating an example process of analyzing EEG data (block 4000) collected from the example headsets 100, 2300, 3400, 3812, 3902 and implemented by the example system 3600 of FIG. 36. The example headsets 100, 2300, 3400, 3812, 3902 have a plurality of electrodes that contact the scalp of a subject to receive electrical signals from the subject's brain. The example process of analyzing EEG data (4000) includes reading the EEG signals from the electrodes (block 4002). In the illustrated example, the signals are converted from an analog signal to a digital signal (block 4004). In some examples, the analog-to-digital conversion takes place in a processing unit, such as, for example, the processing unit 3604 of the example system 3600. In other examples, the analog-to-digital conversion takes place adjacent the electrodes within the headset to convert the signal as close to the source as possible.

In the illustrated example, the signals are conditioned (block 4006) to improve the usefulness of the signals and the accessibility of the data contained therein. For example, as disclosed above, the conditioning may include amplifying the signals and/or filtering the signals (e.g., with a band pass filter). The signals are analyzed (block 4008) to, for example, determine a mental state of the subject, a health condition, an engagement with media as an audience member, an input desire for an electrical device and/or otherwise in accordance with the teachings of this disclosure.

In the illustrated example, the signals are transmitted to an output (block 4010), such as, for example, the output 3618 of the example system 3600. Example modes of output are detailed above including, for example, sounding an alarm, displaying a message and/or other alert on a screen, issuing a report to a local and/or remote computer and/or any other suitable output. In addition, the output may include the wired or wireless communications detailed herein. After the output (block 4010), the example process (4000) ends (block 4012).

Figure 41:
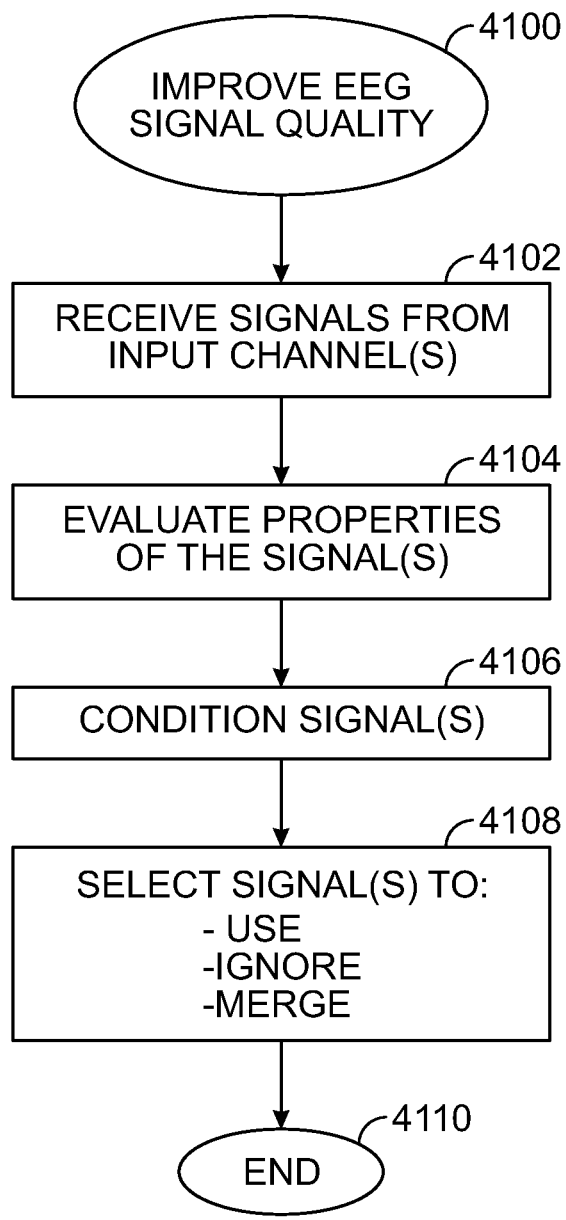
FIG. 41 is a flow chart representing an example method of improving EEG signal quality in accordance with the teachings of this disclosure.

FIG. 41 is a flowchart illustrating an example process of improving EEG signal quality (block 4100) collected, for example, from one or more of the example headsets 100, 2300, 3400, 3812, 3902 and implemented by the example system 3700 of FIG. 37. The example headsets 100, 2300, 3400, 3812, 3902 include a plurality of electrodes (i.e., input channels) in contact with a head of a subject to receive electrical signals from the subject's brain. In some examples, the example process of improving signal quality (4100) is implemented by a processor located at the headset, such as, for example, in the second housing 128 of the headset 100 shown in FIGS. 1-3. In other examples, the example process of improving signal quality (4100) occurs at a remote site, such as, for example, a handheld device, a local computer, a remote server and/or another suitable device.

The example process (4100) includes receiving signals from one or more input channel(s) (e.g., electrode(s)) (block 4102). In some examples, the analyzer 3712 of the system 3700 receives the signals from the input channels for analysis. One or more properties of one or more of the signals are evaluated (block 4104). For example, the signals are evaluated to determine signal strength, amplitude, signal-to-noise ratio, duration and/or other characteristics in accordance with the teachings of this disclosure.

In the illustrated example process (4100), one or more of the signals are conditioned (block 4106) to improve signal quality. In some examples, conditioning the signals enhances the quality of the signals to an acceptable level such that the signal is usable. In other examples, signal conditioning may not provide sufficient improvement to a signal. The example process (4100) also includes selecting one or more signals to use, one or more signals to ignore and two or more signals to merge (block 4108). As disclosed above, two or more signals may be merged by shorting one of the signals, coupling the electrodes providing the signals in parallel and/or averaging two or more signals, which lowers the impedance and improves signal quality as detailed above. The example process (4100) improves signal quality by selecting those signal(s) to use and by ignoring the signals of poor quality. After the selection of valuable and/or improved signals (block 4108), the example processes of improving signal quality (4100) ends (block 4110), and the signals and contained therein may be used in other processes such as, for example, the example analysis process (4000) of FIG. 40.

Figure 42:
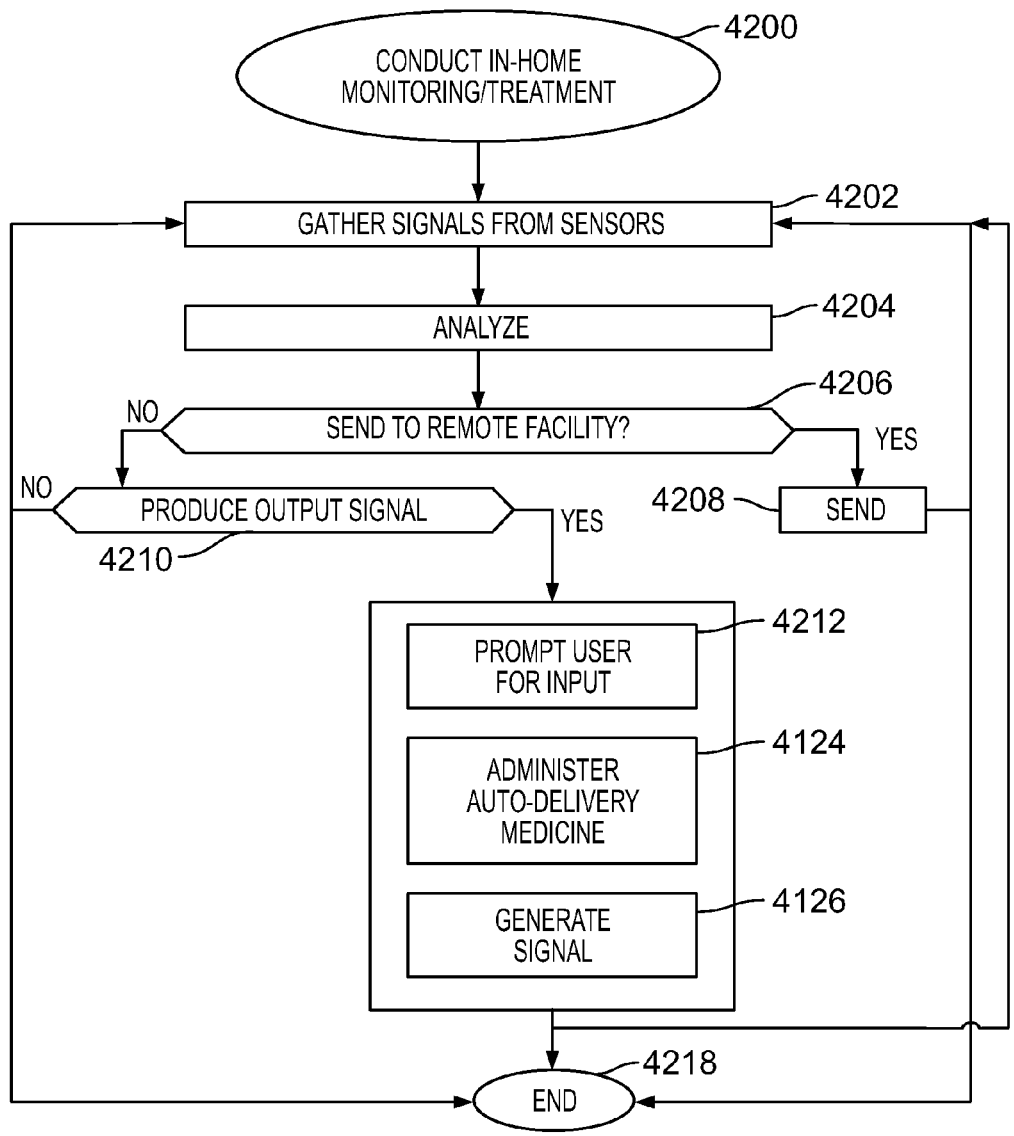
FIG. 42 is a flow chart representing an example method of conducting at-home patient monitoring/treatment in accordance with the teachings of this disclosure.

FIG. 42 is a flowchart illustrating an example process of conducting at-home patient monitoring and treatment (block 4200) using the example headsets 100, 2300, 3400, 3812, 3902 and implemented by the example system 3800 of FIG. 38. The example headsets 100, 2300, 3400, 3812, 3902, as disclosed above, have a plurality of electrodes that contact the scalp of a subject to receive electrical signals from the subject's brain. In some examples, the headsets 100, 2300, 3400, 3812, 3902 are worn by a subject for in-home monitoring, treatment and/or diagnosis of a medical condition, to detect a life-threatening situation, to ascertain patient compliance with a prescribed medical regime and/or other suitable applications in accordance with the teachings of this disclosure.

The example process (4200) includes gathering signals from the electrodes or other suitable sensors (block 4202). As discussed above, the in-home patient monitoring system may incorporate not only the EEG readings from the example headsets, but also other biometric, neurological and/or physiological systems to monitor, treat and/or diagnosis medical conditions of an in-home patient. One or more of the signals are analyzed (block 4204) to determine a mental/physical state of the in-home patient. The signals may be analyzed, for example, with an analyzer or a processor such as the processor 134 disclosed above in the second housing 128 of the headset 100 shown in FIGS. 1-3. One or more of the signals may be conditioned and filtered in accordance with the teachings of this disclosure such as, for example, as disclosed in the example process (4000) of FIG. 40 and/or the example process (4100) of FIG. 41.

The example process (4200) determines whether the signals, an analysis of the signals or a notice related to the signals (e.g., such as an alarm and/or other suitable communication) should be sent to a remote facility (block 4206). The remote facility may be, for example, a doctor's office, a hospital, a clinic, a laboratory, an archive, a research facility and/or any other diagnostic facility. For example, if the signals indicate the occurrence of or an imminent occurrence of a heart attack, a stroke, an epileptic seizure and/or a fall, the example process (4200) determines that the signals, analysis or a notice should be sent to the remote facility (block 4206), and the example process (4200) sends the signals and/or notice or alarm to the remote facility (block 4208). After sending a communication to the remote facility (block 4208), the example process (4200) may end (block 4218) or continue monitoring of the subject by gathering signals from the sensors (block 4202).

If the example process (4200) determines that the signals, analysis or notice is not to be sent to a remote facility (block 4206), the example process (4200) determines if an output signal is to be produced (block 4210) (such as, for example, to warn a patient of a condition or remind him or her of an activity as disclosed in this patent). If an output signal is not to be produced (block 4210) (such as, for example, the signals indicate that the patient's condition is normal and/or the data is otherwise benign), the example process may end (block 4218) or continue monitoring of the subject by gathering signals from the sensors (block 4202).

If the example process (4200) determines that an output signal should be produced (block 4210), multiple types of outputs may be produced including any suitable output disclosed herein such as, for example, prompting a user for input (block 4212). As discussed above, patients often experience difficulty tracking and/or recalling their day-to-day activities. If the analysis indicates a certain spike in the reading occurred, the output signal (block 4210) may prompt the user for input (block 4212) as to what he/she was doing just prior to the spike.

In another example, the output signal (block 4210) administers auto-delivery of medicine (block 4214). For example, if a patient is diabetic, he/she may require continuous glucose and blood pressure monitoring. The process may automatically deliver a dosage of medicine to the patient if his/her reading requires (e.g., the signals indicate that a medical dosage is needed).

In another example, the output signal (block 4210) generates a signal (block 4216) such as a light, a sound, a display and/or any other output is used, for example, to alert a patient of a need to seek medical attention, to take a dosage of medicine, to start an activity, to stop an activity, to eat something and/or any other suitable warning and/or command. After producing one or more output(s) (blocks 4212, 4214, 4216), the example process (4200) may end (block 4218) or continue monitoring of the subject by gathering signals from the sensors (block 4202).

Figure 43:
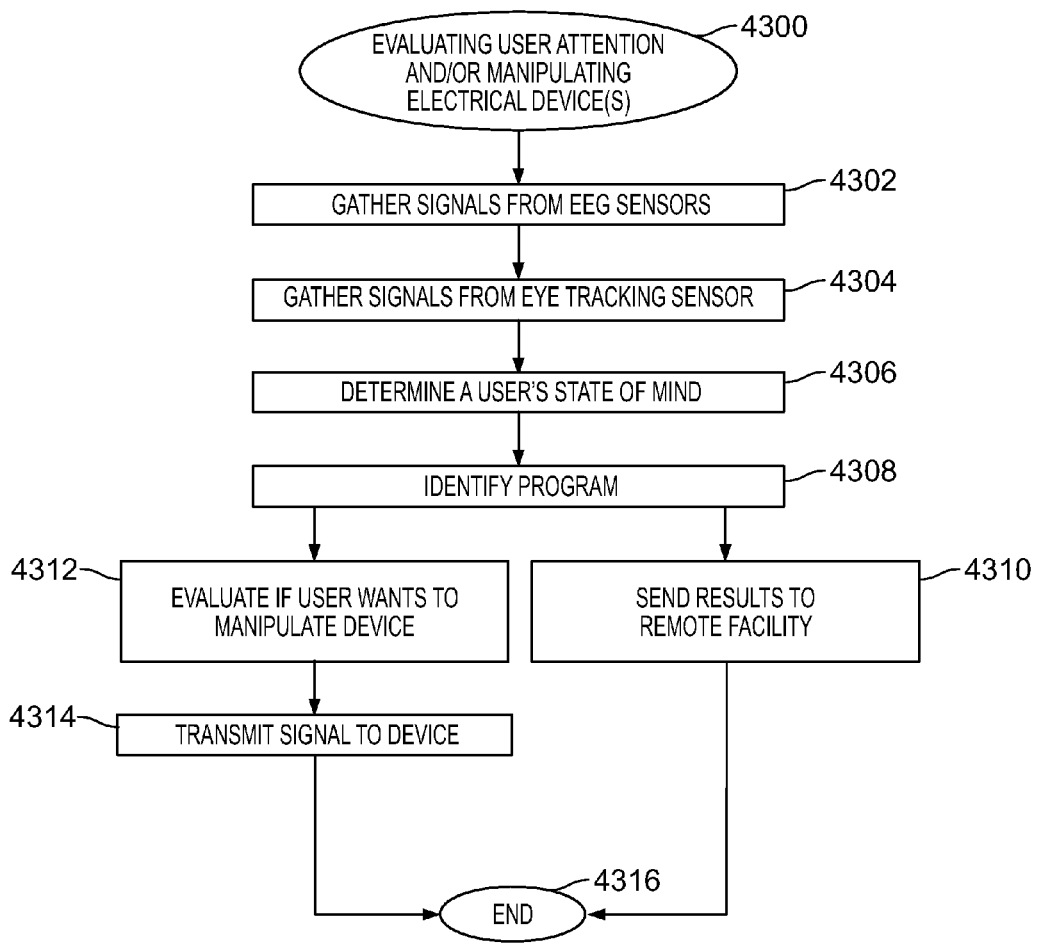
FIG. 43 is a flow chart representing an example method of processing a user's attention to a media and desire to control a device in accordance with the teachings of this disclosure.

FIG. 43 is a flowchart illustrating an example process of evaluating a user's attention to a program and/or manipulating one or more electrical device(s) (block 4300) using the example headsets 100, 2300, 3400, 3812, 3900 and implemented by the example system 3900 of FIG. 39. The example headsets 100, 2300, 3400, 3812, 3900 include a plurality of electrodes to receive electrical signals from the brain for processing in accordance with the example process (4300). The example process (4300) illustrates the utility of EEG data and other physiological data (e.g., eye tracking data) for multiple purposes.

The example process (4300) includes gathering the signals from the EEG sensors (e.g., electrodes and/or input channels) (block 4302). Data from these signals is used to determine attention, memory, focus and/or other neurological states. The example process (4300) also includes gathering signals from an eye tracking sensor (block 4304). As discussed above, the eye tracking data may be used to corroborate the EEG data and both sets of data (e.g., EEG and eye tracking) may be used to determine a neurological state of a user (block 4306).

In an example implementation, the neurological state of a user (block 4306) is useful for audience measurement. For example, if a user is looking in the direction of a television and his or her EEG data indicates that he or she is in a state of engagement or attention, the eye tracking data and EEG data together demonstrate that the user is paying attention to the program. The example process (4300) also identifies what media or program the user is exposed to (block 4308). For example, the process (4300) may collect audio codes and/or signatures using a microphone and/or using any other device in accordance with the teachings of this disclosure. Based on the collected data, the example process (4300) identifies the program or media to which the use is exposed (block 4308). In the illustrated example, data reflecting whether the user is paying attention and to what program the user is or is not paying attention to, is transmitted to a remote facility (block 4310). As discussed above, the remote facility may be a marketing company, a broadcast company or any other organization that might benefit from or otherwise desire to know when users are and/or are not focused on broadcast programs. After the results are sent (block 4310), the example process (4300) may end (block 4316).

In another example implementation, the neurological state of a user (block 4306) is useful for evaluating whether a user wishes to manipulate a device (block 4312) including, for example, an electrical device, as disclosed above. For example, the EEG data and eye tracking data may indicate a user is gazing at a certain area of his/her computer and/or that the user has an increased level of focus. The example process (4300) determines that the user wants to control the device (e.g., computer) by, for example, opening a new application and/or moving a cursor. If the example process (4300) determines that a user wants to control a device (block 4312), the example process (4300) transmits a signal to the device (block 4314) to effect the desired control of the device as disclosed above. After the control signal is transmitted (block 4314), the example process (4300) may end (block 4316).

Figure 44:
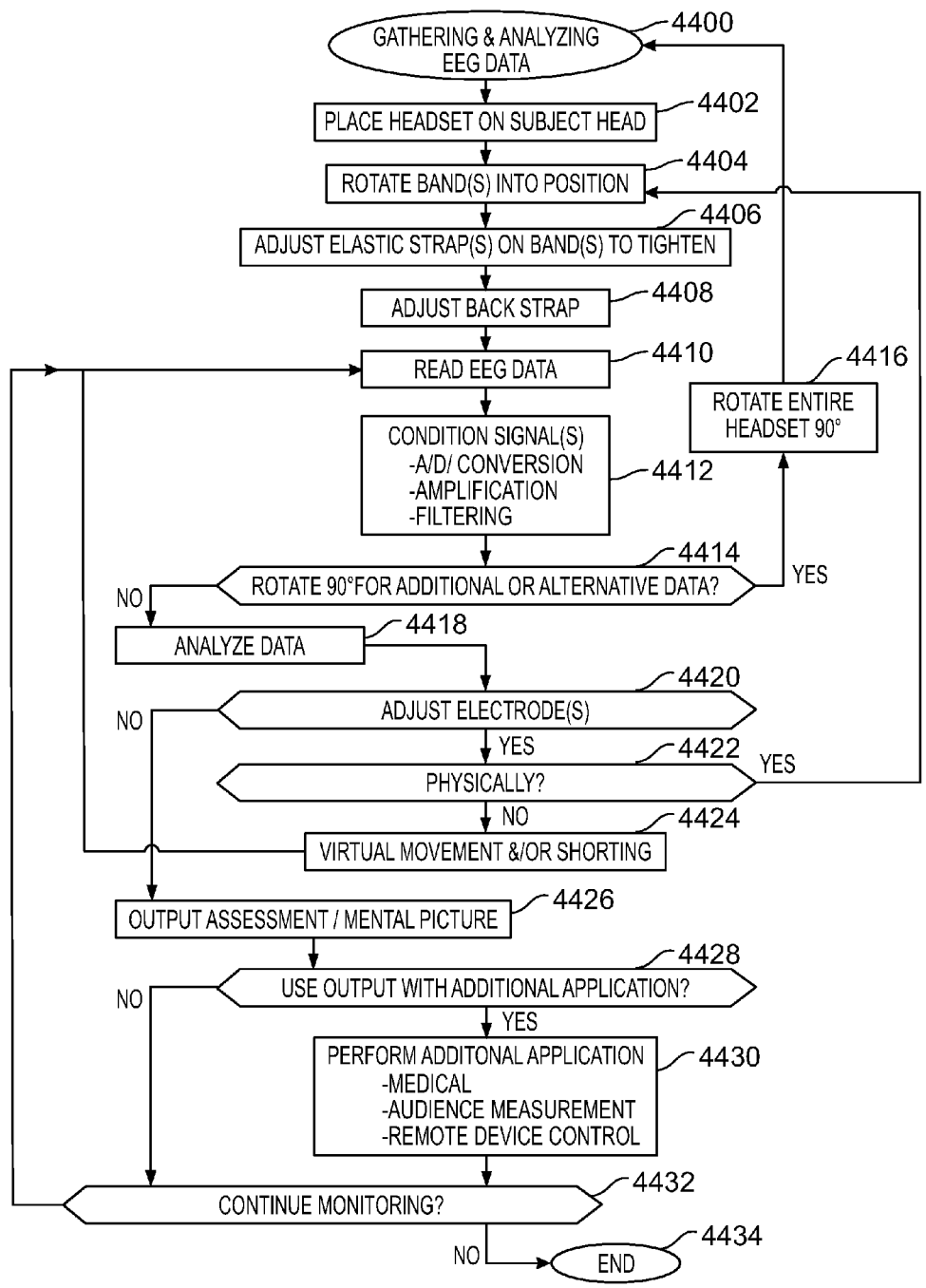
FIG. 44 is a flow chart representing an example method of gathering and analyzing electroencephalographic data in accordance with the teachings of this disclosure.

FIG. 44 is a flowchart illustrating an example process of gathering and analyzing EEG data (block 4400) that may be implemented, for example, with any of the headsets and/or systems disclosed herein. The example process (4400) begins with placing a headset on a subject's head (block 4402). The example headset, as disclosed above, has a plurality of adjustable bands that extend over the head of a user. The headset may include three, four, five, or ten or more individual bands. In some examples, the headset may include less bands such as, for example, one or two. The bands are removably and rotatably coupled on each end to a first housing and a second housing. Each of the bands includes a plurality of electrodes for reading electrical activity along the scalp of a user. The headset may be oriented such that the first housing is near a right ear of a user and the second housing is near a left ear of the user. The user can rotate the individual bands toward the inion (the projection of the occipital bone) or the nasion (the intersection of the frontal bone and two nasal bones) to position the electrodes in specific locations for measuring electrical activity (block 4404). Each of the bands also comprises an elastic strap. The user may adjust the elastic straps on the bands to tighten the bands and press the electrodes on the bands down toward and against the user's head (block 4406). The user may tighten a back strap to secure the headset on the user's head (block 4408).

The example process (4400) also includes reading EEG data such as, for example, from one of more of the electrode(s) disclosed above (block 4410). Raw signals from the electrodes may then be conditioned (block 4412) with hardware, firmware and/or software components, such as, an A/D converter, an amplifier and/or one or more filters as disclosed above. In some examples, one or more of the conditioning components may be incorporated into a housing on a headset, into the individual adjustable bands, at each individual electrode and/or at a remote processor. In some example implementations of the example process (4400), a user determines if it is desirable to rotate the headset 90° (or any other suitable angle) for additional or alternative EEG data (block 4414). With a rotated headset, the bands traverse from the forehead to the back of the head. Such an orientation may be desired, for example, to obtain midline readings. If the user wishes to acquire additional data in the orthogonal position (block 4414), he or she rotates the headset 90° (block 4416) and repositions and adjusts the bands as explained above (blocks 4402-4408). With the headset positioned for the desired reading (block 4414) the conditioned signals are analyzed (block 4418).

The example process (4400) also includes determining if one or more of the electrode(s) needs to be or should be adjusted (block 4420). An electrode should be adjusted, for example, to obtain a clearer signal. If one or more the electrode(s) are to be adjusted, the example process (4400) includes determining if the adjustment is to a physical adjustment or a non-physical adjustment (4422). If the adjustment is a physical adjustment (4422), control of the example process (4400) returns to block 4404, and the appropriate band(s) are rotated into position and/or the elongated strap(s) or straps are adjusted (blocks 4406-4408). If the electrode(s) are to be non-physically adjusted (4422), the example process (4400) includes virtually moving and/or shorting one or more of the electrode(s) (block 4424), as detailed above. With the adjusted electrode(s), the example process (4400) returns to continue to read the EEG signal (block 4410), and the example process (4400) continues.

If the electrode(s) do not need to be further adjusted (block 4424), then the signals are analyzed to produce an output assessment or mental picture (block 4426). As disclosed above, the output assessment or mental picture may determine, for example, the neurological state of the person. For example, as provided in examples disclosed above, the EEG data includes multiple frequency bands, which can be analyzed to determine, for example, if person has high concentration, is sleeping, is depressed, is happy, is calm and/or any other emotional and/or neurological state as disclosed above. The output assessment/mental picture provides insights into the thoughts, emotions and/or health of the person.

The example method 4400 also includes determining if the output is to be used with one or more additional application(s) (block 4428). If the output is to be used with one or more additional application(s) such as, for example, medical applications, audience measurements, remote device control and/or any other suitable application as disclosed herein, such applications are performed (block 4430). The example process (4400) also determines if monitoring of EEG data should continue (block 4432). If further monitoring is to be conducted, control of the method returns to block 4410, and EEG signal data is read. If further monitoring is not to be conducted, then the example method 4400 ends (block 4434).

Figure 45:
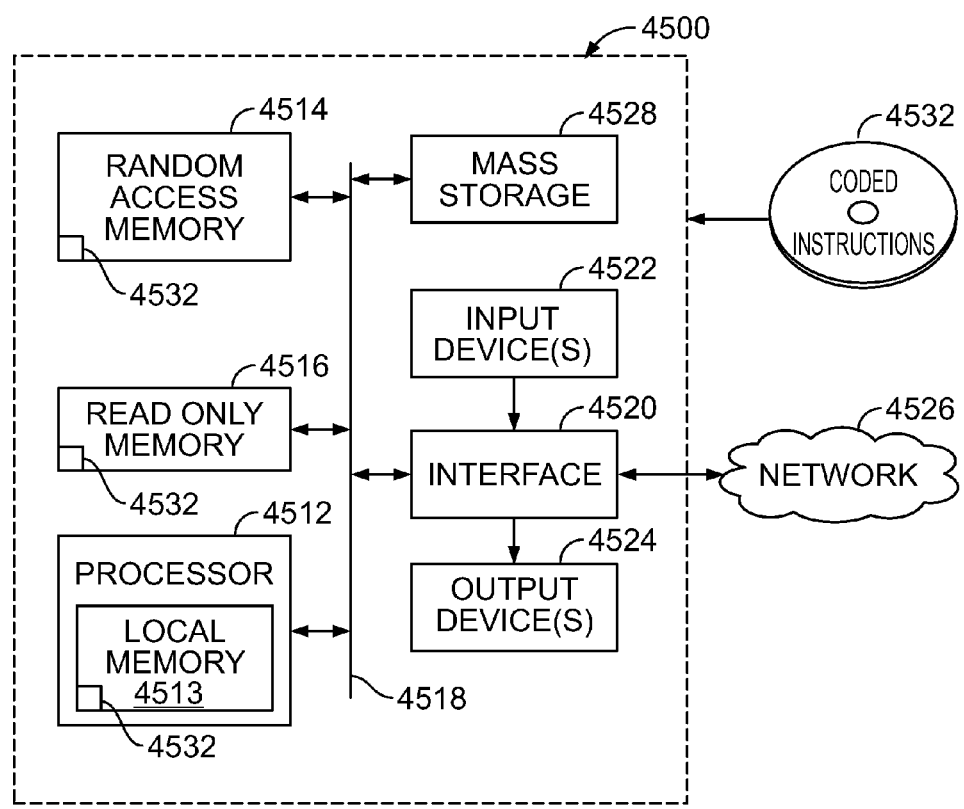
FIG. 45 illustrates an example processor platform that may execute one or more of the instructions of FIGS. 40-44 to implement any or all of the example methods, systems and/or apparatus disclosed herein.

FIG. 45 is a block diagram of an example processing platform 4500 capable of executing the one or more of the instructions of FIGS. 40-44 to implement one or more portions of the apparatus and/or systems of FIGS. 1, 23, 34 and 36-39. The processing platform 4500 can be, for example a processor in a headset, a server, a personal computer, and/or any other type of computing device.

The system 4500 of the instant example includes a processor 4512. For example, the processor 4512 can be implemented by one or more microprocessors or controllers from any desired family or manufacturer.

The processor 4512 includes a local memory 4513 (e.g., a cache) and is in communication with a main memory including a volatile memory 4514 and a non-volatile memory 4516 via a bus 4518. The volatile memory 4514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 4516 may be implemented by flash memory and/or any other desired type of memory device. Access to the main memory 4514, 4516 is controlled by a memory controller.

The processing platform 4500 also includes an interface circuit 4520. The interface circuit 4520 may be implemented by any type of interface standard, such as an Ethernet interface, a universal serial bus (USB), and/or a PCI express interface.

One or more input devices 4522 are connected to the interface circuit 4520. The input device(s) 4522 permit a user to enter data and commands into the processor 4512. The input device(s) can be implemented by, for example, an electrode, a physiological sensor, a keyboard, a mouse, a touchscreen, a track-pad, a trackball, isopoint and/or a voice recognition system.

One or more output devices 4524 are also connected to the interface circuit 4520. The output devices 4524 can be implemented, for example, by display devices (e.g., a liquid crystal display and/or speakers). The interface circuit 4520, thus, typically includes a graphics driver.

The interface circuit 4520 also includes a communication device (e.g., transmitter 3616, 3916) such as a modem or network interface card to facilitate exchange of data with external computers via a network 4526 (e.g., an Ethernet connection, a digital subscriber line (DSL), a telephone line, coaxial cable, a cellular telephone system, etc.).

The processing platform 4500 also includes one or more mass storage devices 4528 for storing software and data. Examples of such mass storage devices 4528 include floppy disk drives, hard drive disks, compact disk drives and digital versatile disk (DVD) drives. The mass storage device 4628 may implement the local storage device 3612, 3822, 3914.

The coded instructions 4532 of FIGS. 40-44 may be stored in the mass storage device 4528, in the volatile memory 4514, in the non-volatile memory 4516, and/or on a removable storage medium such as a CD or DVD.

Although certain example apparatus have been described herein, the scope of coverage of this patent is not limited thereto. On the contrary, this patent covers all methods, apparatus, and articles of manufacture fairly falling within the scope of the appended claims either literally or under the doctrine of equivalents.

What is claimed is:

1. A method comprising:
   obtaining first neuro-response data from a subject with a device oriented in a first direction relative to the subject, the device including:
   a first band including a first set of electrodes; and
   a second band including a second set of electrodes; and
   obtaining second neuro-response data from the subject with the device oriented in a second direction relative to the subject, the second direction substantially orthogonal to the first direction.

2. The method of claim 1, wherein the first band has a first end and a second end, the second band has a third end and a fourth end, the first end is coupled to the third end, and the second end is coupled to the fourth end.

3. The method of claim 2, wherein the first end is coupled to the third end through a first housing and the second end is coupled to the fourth end through a second housing.

4. The method of claim 3 further including analyzing, by executing an instruction with a processor disposed in the second housing, the first neuro-response data and the second neuro-response data.

5. The method of claim 4, wherein the first housing includes an adjustment mechanism to adjust a fit of the device on the subject.

6. The method of claim 4, further including determining, by executing instruction with the processor, a mental state of the subject.

7. The method of claim 6, further including transmitting, with a transmitter disposed in the second housing, at least one of the mental state, the first neuro-response data, or second neuro-response data.

8. The method of claim 4, further including amplifying, via an amplifier disposed in the second housing, at least one of the first neuro-response data or the second neuro-response data.

9. The method of claim 3, wherein, when the device is oriented in the first direction, the first housing is disposed near a first ear of the subject and the second housing is disposed near a second ear of the subject and, when the device is oriented in the second direction, the first housing is disposed on a forehead of the subject and the second housing is disposed on a back of a head of the subject.

10. The method of claim 3, wherein the first band and the second band are rotatably coupled to the first housing and the second housing.

11. The method of claim 3, wherein the first band and the second band are removably coupled to the first housing and the second housing.

12. The method of claim 1 further including gathering a midline reading from a brain of the subject with the device oriented in the second direction.

13. The method of claim 1, wherein the first direction is side-to-side and the second direction is front-to-back.

14. The method of claim 1, further including independently adjusting a position of the first band and the second band.

15. The method of claim 1, further including, after obtaining the first neuro-response data, rotating the device on a head of the subject.

16. The method of claim 1, wherein the first neuro-response data and the second neuro-response data include electroencephalographic data.

17. The method of claim 1, wherein the first band includes a first adjustable elastic band to a change a first distance between the first band and a head of the subject and the second band includes a second adjustable elastic band to change a second distance between the second band and the head of the subject.

18. The method of claim 1, wherein the first band includes a plurality of extensions and the electrodes of the first set are individually disposed at respective ends of the extensions.

19. The method of claim 18, wherein the extensions are flexible.

20. The method of claim 1, wherein at least one of the electrodes of the first set includes at least one of a portion of a ring, a ball, or a hook.

* * * * *